(12) United States Patent
Stoltz et al.

(10) Patent No.: US 8,822,679 B2
(45) Date of Patent: Sep. 2, 2014

(54) QUATERNARY HETEROATOM CONTAINING COMPOUNDS

(75) Inventors: Brian M Stoltz, San Marino, CA (US); Scott C. Virgil, Pasadena, CA (US); David E White, Wayne, PA (US); Taiga Yurino, Kyoto (JP); Yiyang Liu, Pasadena, CA (US); Douglas C Behenna, Laguna Niguel, CA (US); Douglas Duquette, Temple City, CA (US); Christian Eidamshaus, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 21 days.

(21) Appl. No.: 13/531,485

(22) Filed: Jun. 22, 2012

(65) Prior Publication Data

US 2013/0012701 A1    Jan. 10, 2013

Related U.S. Application Data

(60) Provisional application No. 61/501,054, filed on Jun. 24, 2011.

(51) Int. Cl.
| | | |
|---|---|---|
| C07D 211/78 | (2006.01) |
| C07C 229/00 | (2006.01) |
| C07D 207/277 | (2006.01) |
| C07D 207/36 | (2006.01) |
| C07D 223/04 | (2006.01) |
| C07D 223/10 | (2006.01) |
| C07D 241/08 | (2006.01) |
| C07D 265/32 | (2006.01) |
| C07D 309/08 | (2006.01) |
| C07D 309/30 | (2006.01) |
| C07F 7/18 | (2006.01) |

(52) U.S. Cl.
USPC ........... 540/529; 540/607; 544/172; 544/383; 546/14; 546/203; 546/205; 546/220; 546/222; 548/536; 549/291; 549/424; 560/41

(58) Field of Classification Search
None
See application file for complete search history.

(56) References Cited

U.S. PATENT DOCUMENTS 5,591,769 A    1/1997 Himmelsbach et al.
2010/0298293 A1   11/2010 Allerheiligen et al.

FOREIGN PATENT DOCUMENTS

WO    WO-2009013390 A1    1/2009
WO    WO-2009153178 A2    12/2009

OTHER PUBLICATIONS

Imao et al., Easy Access to Esters with a Benzylic Quaternary Carbon Center from Diallyl Malonates by Palladium-Catalyzed Decarboxylative Allylation, 72 J.O.C. 1652-1658 (2007).*

Amat et al., "Enantioselective Synthesis of 3,3-Disubstituted Piperidine Derivatives by Enolate Dialkylation of Phenylglycinol-derived oxazolopiperidone Lactams," J. Org. Chem., 72:4431-4439 (2007).
Badillo et al., "Enantioselective synthesis of substituted oxindoles and spirooxindoles with applications in drug discovery," Current Opinion in Drug Discovery & Development, 13(6):758-776 (2010).
Baussanne et al., "Diastereoselective Bis-Alkylation of Chiral Non-Racemic α, β-Unsaturated γ-Lactams," Tetrahedron Letters, 35(23):3931-3934 (1994).
Behenna and Stoltz, "The Enantioselective Tsuji Allylation," J. Am. Chem. Soc., 126(46):15044-15045 (2004).
Day et al., "The Catalytic Enantioselective Total Synthesis of (+)-Liphagal," Angew. Chem. Int. Ed., 50:6814-6818 (2011).
Desmaele et al., "Stereocontrolled Elaboration of Quaternary Carbon Centers through the Asymmetric Michael-Type Alkylation of Chiral Imines/Secondary Enamines: Enantioselective Synthesis of (+)-Vincamine," J. Org. Chem., 62:3890-3901 (1997).
Enders et al., "Asymmetric Electrophilic Substitutions at the α-Position of γ- and δ-Lactams," Eur. J. Org. Chem., pp. 4463-4477 (2001).
Enquist and Stolz, "The total synthesis of (−)-cyanthiwigin F by means of double catalytic enantioselective alkylation," Nature, 453:1228-1231 (2008).
Ezquerra et al., "Stereoselective Double Aklylation of Ethyl N-Boc-pyroglutamate," J. Org. Chem., 59(15):4327-4331 (1994).
Groaning and Meyers, "Chiral Non-Racemic Bicyclic Lactams. Auxiliary-Based Asymmetric Reactions," Tetrahedron, 56(549):9843-9873 (2000).

(Continued)

*Primary Examiner* — Janet L Andres
*Assistant Examiner* — Timothy R Rozof
(74) *Attorney, Agent, or Firm* — David P. Halstead; Foley Hoag LLP

(57) ABSTRACT

A compound useful as a building block for the manufacture of various compounds is represented by Formula A or D.

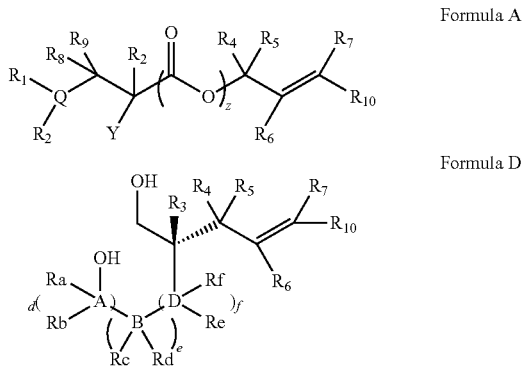

In Formula A and D, z is 0 or 1; Q is a heteroatom; R1 through R11 and Ra through Rf are each independently hydrogen, a substituted or unsubstituted hydrocarbyl group, a substituted or unsubstituted heteroatom containing hydrocarbyl group, or a functional group; d, e and f are each independently 0 or greater; each of A, B and D is independently a carbon atom or a heteroatom; and two or more of R1 though R11, Ra through Rf and Y optionally combine to form a ring. In some embodiments, R8 and R9 combine to form a carbonyl group. In some embodiments, R2 and Y combine to form a ring with the Q atom. In some embodiments, the ring includes at least one double bond.

16 Claims, 1 Drawing Sheet

(56) References Cited

OTHER PUBLICATIONS

Helmchen and Pfaltz, "Phosphinooxazolines—A New Class of Versatile, Modular P,N-Ligands for Asymmetric Catalysis," Acc. Chem. Res., 33(6):336-345 (2000).
International Search Report for PCT/US2012/043904 mailed Feb. 1, 2013.
Jakubec et al., "Enantio- and diastereoselective Michael additions of C-succinimidyl esters to nitro olefins using cinchonine-derived bifunctional organocatalysts," Tetrahedron: Asymmetry, 22:1147-1155 (2011).
Juaristi et al., Enantioselective synthesis of β-amino acids. Part 9: Preparation of enantiopure α, α-disubstituted β-amino acids from 1-benzoyl-2(S)-*tert*-butyl-3-methylperhydropyrimidin-4-one[1,2], Tetrahedron: Asymmetry, 9:3881-3888 (1998).
Kim et al., An Asymmetric Synthesis of (+)-Isonitramine by 'Triple Allylic Strain-Controlled' Intramolecular $S_N2$' Alkylation, Tetrahedron Letters, 37(9):1433-1434 (1996).
Lu and Ma, "Metal-Catalyzed Enantioselective Allylation in Asymmetric Synthesis," Angew. Chem. Int. Ed., 47:258-297 (2008).
McDougal et al., "High-Throughput Screening of the Asymmetric Decarboxylative Alkylation Reaction of Enolate-Stabilized Enol Carbonates," Snylett, 11:1712-1716 (2010).
McDougal et al., "Rapid synthesis of an electron-deficient *t*-BuPHOX ligand: cross-coupling of aryl bromides with secondary phosphine oxides," Tetrahedron Letters, 51:5550-5554 (2010).
McFadden and Stoltz, "The Catalytic Enantioselective, Protecting Group-Free Total Synthesis of (+)-Dichroanone," J. Am. Chem. Soc., 128:7738-7739 (2006).
Meyers et al., "Stereoselective Alkylations in Rigid Systems. Effect of Remote Substituents on π-Facial Additions to Lactam Enolates. Stereoelectronic and Steric Effects," J. Am. Chem. Soc., 120:7429-7438 (1998).
Mohr and Stoltz, "Enantioselective Tsuji Allylations," Chem. Asian J., 2:1476-1491 (2007).
Mohr et al., "Deracemization of Quaternary Stereocenters by Pd-Catalyzed Enantioconvergent Decarboxylative Allylation of Racemic β-Ketoesters," Angew.Chem. Int. Ed., 44:6924-6927 (2005).
Moss et al., "Catalytic Enantio- and Diastereoselective Alkylations with Cyclic Sulfamidates," Angew. Chem. Int. Ed., 49:568-571 (2010).
Ojima and Pei, "Asymmetric Synthesis with Chiral β-Lactams. Highly Stereoselective Alkylation and Aldol Reaction of a Chiral 3-Amino-4-Styryl-β-Lactam," Tetrahedrom Letters, 31(7):977-980 (1990).
Park et al., "Highly Enantioselective Phase-Transfer Catalytic α-Alkylation of α-*tert*-Butoxycarbonyllactams: Construction of β-Quaternary Chiral Pyrrolidine and Piperidine Systems," Adv. Synth. Catal., 353:3313-3318 (2011).
Schwarz and Meyers, "Tandem α-Cyano Enamine/Enolate Alkylations on Bicyclic Lactams: Asymmetric Carbocycle and Heterocycle Synthesis," J. Org. Chem., 63(5):1619-1629 (1998).
Seto et al., "Catalytic Enantioselective Alkylation of Substituted Dioxanone Enol Ethers: Ready Access to C(α)-Tetrasubstituted Hydroxyketones, Acids, and Esters," Angew. Chem. Int. Ed., 47:6873-6876 (2008).
Streuff et al., "A palladium-catalysed enolate alkylation cascade for the formation of adjacent quaternary and tertiary sterocentres," Nature Chemistry, 2:192-196 (2010).
Takahashi et al., "Atropisomeric lactam chemistry: catalytic enantioselective synthesis, application to asymmetric enolate chemistry and synthesis of key intermediates for NET inhibitors," Tetrahedron, 66:288-296 (2010).
Tani et al., "A Facile and Modular Synthesis of Phosphinooxazoline Ligands," Organic Letters, 9(13):2529-2531 (2007).
Tari et al., "Recoverable *Cinchona* ammonium salts as organocatalysts in the enantioselective Michael addition of β-Keto esters," Tetrahedron: Asymmetry, 21:2872-2878 (2010).
Trost and Brennan, "Asymmetric Synthesis of Oxindole and Indole Spirocyclic Alkaloid Natural Products," Synthesis, 18:3003-3025 (2009).
Trost, Barry M., "Asymmetric Allylic Alkylation, an Enabling Methodology," J. Org. Chem., 69(18):5813-5837 (2004).
Varea et al., "Asymmetric Synthesis. XXXV[1]. Synthesis of 2-Methyl 5-Substituted Piperidines from Chiral Non-racemic Lactams," Tetrahedron Letters, 36(7):1035-1038 (1995).
Vijn et al., "Highly Enantioselective Synthesis of a 2,3-Dihydroindole Mediated by *N*-Methylephedrine," Angew. Chem. Int. Ed. Engl., 23(2):165-166 (1984).
Weaver et al., "Transition Metal-Catalyzed Decarboxylatiave Allylation and Benzylation Reactions," Chem. Rev., 111:1846-1913 (2011).
White et al., "The Catalytic Asymmetric Total Synthesis of Elatol," J. Am. Chem. Soc., 130(3):810-811 (2008).
Zhou et al., "Catalytic Asymmetric Synthesis of Oxindoles Bearing a Tetrasubstituted Stereocenter at the C-3 Position," Adv. Synth. Catal., 352:1381-1407 (2010).
Bobranski et al., Hydration of Phenyldiallylacetamide, 7, Bulletin de l'Academie Polonaise de Sciences, Serie des Sciences, Chimiques, Geologiques et Geographiques, pp. 399-401 (1959) (CAS Abstract).
Mertes et al., "Glutarimides", J.Am.Pharma. Assoc. vol. 67, pp. 882-885, (1912-1977) (1958) (CAS Abstract).

\* cited by examiner

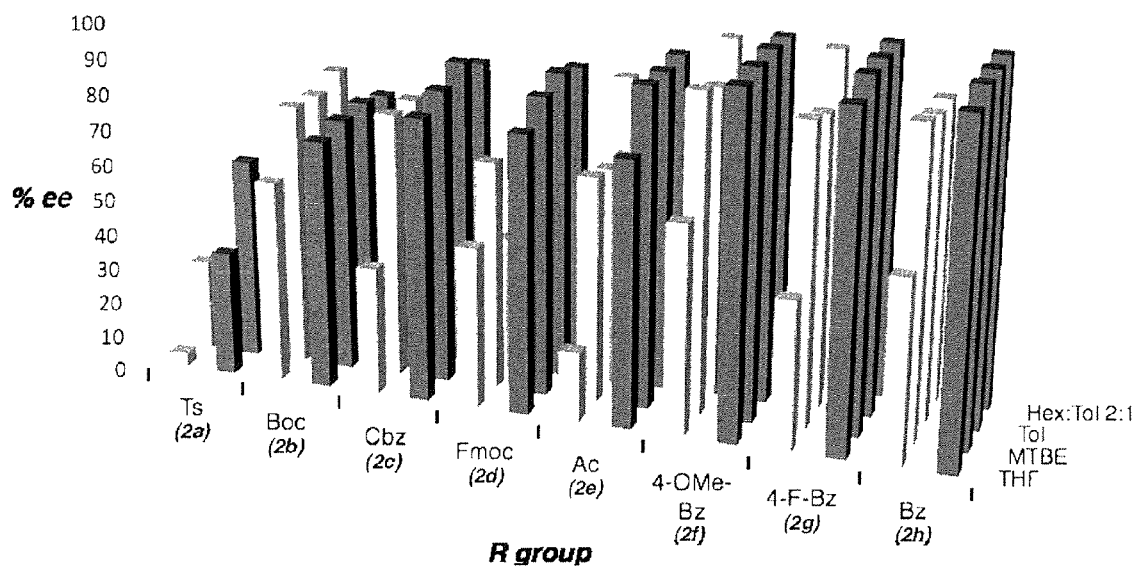
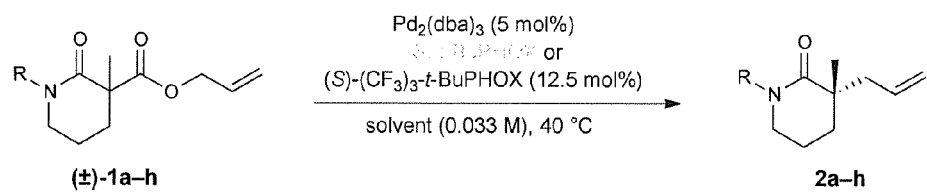
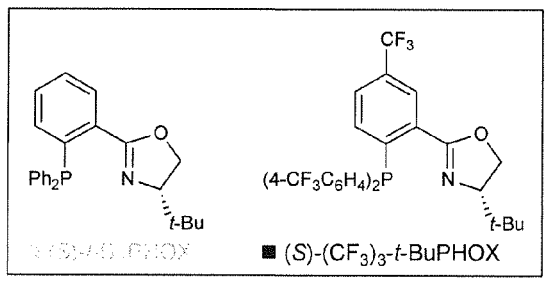

QUATERNARY HETEROATOM CONTAINING COMPOUNDS

CROSS REFERENCE TO RELATED APPLICATION

This application claims priority to and the benefit of U.S. Provisional Application Ser. No. 61/501,054, filed on Jun. 24, 2011, the entire content of which is incorporated herein by reference.

STATEMENT REGARDING FEDERALLY SPONSORED RESEARCH

This invention was made with government support under Grant No. GM080269 awarded by the National Institutes of Health. The government has certain rights in the invention.

TECHNICAL FIELD

The disclosure relates to quaternary nitrogen compounds useful as building blocks in the synthesis of pharmaceuticals and other compounds.

BACKGROUND

Nitrogen-containing heterocycles are prevalent in numerous biologically active products that are the bases and templates for countless pharmaceuticals and other compounds used in many disciplines, including medicinal chemistry. A small sampling of some these compounds include aspidospermidine, fawcettimine, vinblastine, manzamine A, ethosuximide, aminoglutethimide and doxapram, depicted below.

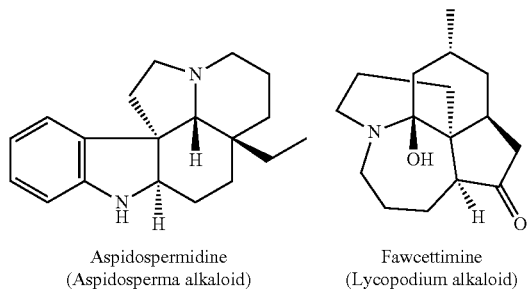

Aspidospermidine (Aspidosperma alkaloid)

Fawcettimine (Lycopodium alkaloid)

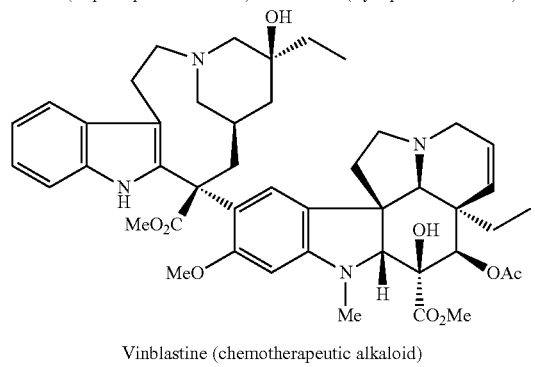

Vinblastine (chemotherapeutic alkaloid)

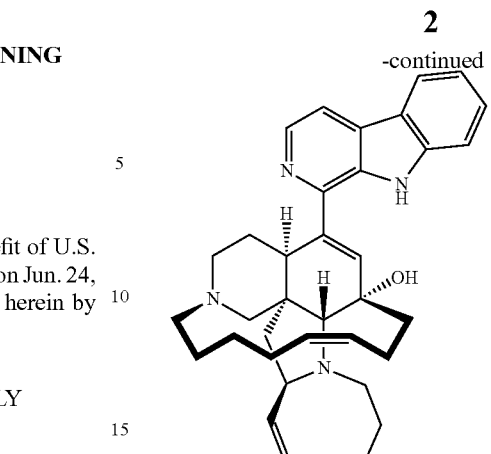

Manzamine A (marine alkaloid)

Ethosuximide (anticonvulsant)

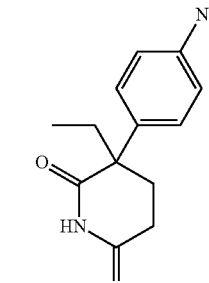

Aminoglutethimide (aromatase inhibitor)

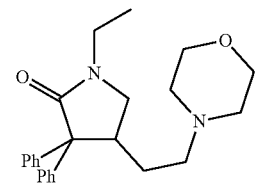

Doxapram (respiratory stimulant)

Typically only one enantiomer of a compound exhibits biological activity, while the other enantiomer generally exhibits no activity, or substantially reduced activity. In addition, different stereoisomers of a compound often exhibit differences in biological activity. As such, a stereoselective and enantioselective synthesis of the target compound could theoretically produce pharmaceuticals or compounds with greater biological activity, and therefore, greater medicinal value. However, stereoselective and enantioselective syntheses of these types of compounds have proven very difficult. Indeed, most syntheses reported to date yield racemic mixtures of the various compounds. While some stereoselective methods for the synthesis of certain nitrogen containing heterocycles and their cyclic amine derivatives are known, only a sparse number of enantioselective methods exist. Additionally, most of these stereoselective methods use chiral auxiliary chemistry specific to the oxindole lactam nucleus or cyclic imides, both of which require enolate stabilization, thereby limiting the scope of each transformation.

SUMMARY

In embodiments of the present invention, a compound is represented by Formula A, Formula A(ii), Formula D or Formula D(i).

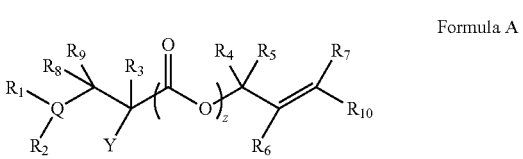

Formula A

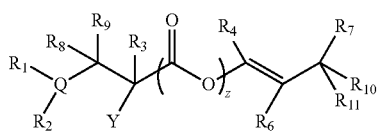

Formula A(ii)

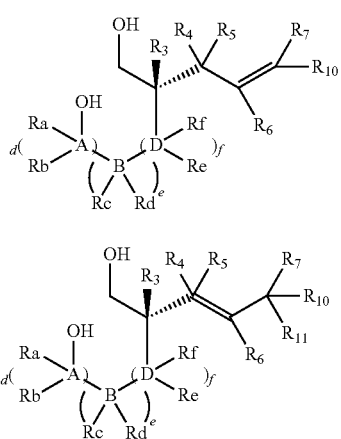

Formula D

Formula D(i)

In Formula A, A(ii), D and D(i), z is 0 or 1; Q is a heteroatom; each of R1 through R11 and Ra through Rf is independently hydrogen, a substituted or unsubstituted hydrocarbyl group, a substituted or unsubstituted heteroatom containing hydrocarbyl group, or a functional group; each of d, e and f is independently an integer of 0 or greater; each of A, B and D is independently a carbon atom or a heteroatom; and two or more groups selected from R1 though R11, Ra through Rf and Y optionally combine to form a ring. In some embodiments, R8 and R9 combine to form a carbonyl group. In some embodiments, R2 and Y combine to form a ring with Q, and the ring may be saturated or may include at least one double bond. In some embodiments, Q is N or O. When Q is N, R1 may be an amine protecting group. In some embodiments, however, R1 may be H or OH. For example, in some embodiments, z is 0 and R1 is either H or OH.

In some exemplary embodiments, the compound of Formula A may be a compound represented by Formula C.

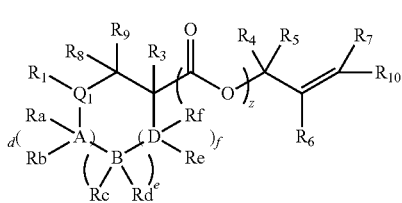

Formula C

In Formula C, z is 0 or 1; each of d, e and f is independently an integer of 0 or greater; Q1 is a heteroatom; and each of A, B and D is independently a heteroatom or a carbon atom. In some embodiments, R1 may be H or OH. For example, in some embodiments, z is 0 and R1 is either H or OH. In Formula C, R8 and R9 may optionally combine to form a carbonyl group such that the compound of Formula C is represented by Formula C(i).

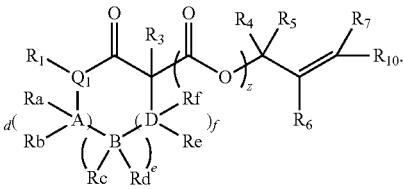

Formula C(i)

In Formulae C and C(i), R1 and one Ra may combine to form a double bond, or one Rb and one Rc may combine to form a double bond, or one Rd and one Re may combine to form a double bond. In some embodiments, in Formulae C and C(i), one Ra and one Rb may combine to form a carbonyl group, or one Rc and one Rd may combine to form a carbonyl group, or one Re and one Rf may combine to form a carbonyl group. Also, in some embodiments, R1 is H or OH.

In some embodiments, the compound of Formula A, A(ii), D or D(i) is racemic, i.e., the compound includes a generally equimolar mixture of the (+) and (−) enantiomers of the compound. For example, in some embodiments, e.g., those in which z is 1, the compound is racemic. However, in some other embodiments, the compound of Formula A, A(ii), D or D(i) is enantioenriched, i.e., the compound includes more of one enantiomer than the other. For example, in some embodiments, e.g., in which z is 0, the compound may be an enantioenriched compound in which the compound includes one of the (+) or the (−) enantiomer in an enantiomeric excess of greater than 50%, for example greater than 60%, or greater than 70%, or greater than 80%, or greater than 90%.

According to some embodiments of the present invention, a method of making an enantioenriched heteroatom containing compound includes subjecting the compound of claim 1 to palladium catalyzed decarboxylative alkylation using an electron poor ligand, a palladium-based catalyst, and a solvent. The electron poor ligand may be a ligand including an electron poor moiety selected from fluorine atoms, partially or fully fluorinated hydrocarbyl groups, partially or fully fluorinated heteroatom containing hydrocarbyl groups, $NO_2$ groups and $SO_2R$ groups, wherein R is hydrogen, a substituted or unsubstituted hydrocarbyl group, a substituted or unsubstituted heteroatom containing hydrocarbyl group, or a functional group. For example, the electron poor ligand may be a R'-PHOX ligand, where R' is selected from $(CF_3)_3$ groups, partially or fully fluorinated hydrocarbyl groups, partially or fully fluorinated heteroatom containing hydrocarbyl groups, $NO_2$ groups and $SO_2R$ groups, wherein R is hydrogen, a substituted or unsubstituted hydrocarbyl group, a substituted or unsubstituted heteroatom containing hydrocarbyl group, or a functional group.

BRIEF DESCRIPTION OF THE DRAWINGS

These and other features and advantages of the present invention will be better understood by reference to the following detailed description when considered in conjunction with the following drawing, in which:

FIG. 1 is a graph comparing the enantiomeric excess of different compounds prepared via a palladium catalyzed decarboxylative alkylation process according to embodiments of the present invention.

DETAILED DESCRIPTION

Nitrogen-containing heterocycles are ubiquitous in natural products, pharmaceuticals, and materials science. Given the abundance of these heterocycles in nature, pharmacology, and materials science, stereoselective methods for the synthesis of 3,3-disubstituted pyrrolidinones, piperidinones, and caprolactams, in addition to their corresponding amines, would, in theory, be valuable for the preparation of a wide array of important structures in these areas of research. The general formulae for such disubstituted pyrrolidinones, piperidinones, and caprolactams are depicted below.

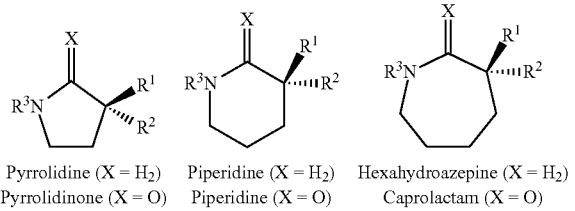

Pyrrolidine (X = H₂)   Piperidine (X = H₂)   Hexahydroazepine (X = H₂)
Pyrrolidinone (X = O)  Piperidine (X = O)    Caprolactam (X = O)

A small sample of the products these disubstituted pyrrolidinones, piperidinones and caprolactams could theoretically be used to prepare includes those depicted below.

Aspidospermidine
(Aspidosperma alkaloid)

Fawcettimine
(Lycopodium alkaloid)

Vinblastine (chemotherapeutic alkaloid)

Manzamine A
(marine alkaloid)

Ethosuximide
(anticonvulsant)

Aminoglutethimide
(aromatase inhibitor)

Doxapram
(respiratory stimulant)

However, as can be seen from the small sample depicted above, many of the target compounds include quaternary centers, e.g., C(α)-quaternary centers. Unfortunately, a paucity of enantioselective lactam syntheses leading to such C(α)-quaternary centers is known. Indeed, most known methods rely on chiral auxiliary chemistry, and although a few catalytic examples exist, they are specific to the oxindole lactam nucleus, α-carbonyl stabilized enolates, or cyclic imides. Importantly, enolate stabilization is critical for success in these catalytic systems, thereby limiting the scope of each transformation. To date, there are no examples of catalytic asymmetric alkylations of simple piperidinone, pyrrolidinone, and caprolactam scaffolds (or other nitrogen containing compounds, e.g., acyclic compounds) for the formation of C(α)-quaternary or C(α)-tetrasubstituted tertiary centers.

Transition metal-catalyzed allylic alkylation is a key method for the enantioselective preparation of chiral substances and ranks among the best general techniques for the catalytic alkylation of prochiral enolates. Given the importance of α-quaternary lactams (discussed above), embodiments of the present invention are directed to a general method for catalytic asymmetric α-alkylation of cyclic and acyclic quaternary heteroatom containing compounds (including nitrogen containing compounds, e.g., lactams, and their structurally analogous oxygen containing compounds, e.g., lactones). Over the past several years, methods for the synthesis of α-quaternary ketones have been reported, and the use of these methods has been demonstrated in a number of complex molecule syntheses. See Mohr, et al., "Deracemization of quaternary stereocenters by Pd-catalyzed enantioconvergent decarboxylative allylation of racemic β-ketoesters, "*Angew. Chem., Int. Ed.* 44, 6924-6927 (2005); Seto, et al., "Catalytic enantioselective alkylation of substituted dioxanone enol ethers: ready access to C(α)-tetrasubstituted hydroxyketones, acids, and esters," *Angew. Chem. Int. Ed.* 47, 6873-6876 (2008); Streuff, et al., "A Palladium-catalysed enolate alkylation cascade for the formation of adjacent quaternary and tertiary stereocenters," *Nature Chem.* 2, 192-196 (2010); McFadden, et al., The catalytic enantioselective, protecting group-free total synthesis of (+)-dichroanone," *J. Am. Chem. Soc.* 128, 7738-7739 (2006); White, et al., The catalytic asymmetric total synthesis of elatol," *J. Am. Chem. Soc.* 130, 810-811 (2008); Enquist, et al., The total synthesis of (−)-cyanthiwigin F via double catalytic enantioselective alkylation," *Nature* 453, 1228-1231 (2008); Day, et al., The catalytic enantioselective total synthesis of (+)-liphagal," *Angew. Chem. Int. Ed.* 50, in press (2011), the entire content of all of which are incorporated herein by reference. Related allylic alkylation methods have also been developed. See Trost, et al., "Regio- and Enantioselective Pd-Catalyzed Allylic Alkylation of Ketones through Allyl Enol Carbonates," *J. Am.*

Chem. Soc. 127, 2846-2847 (2005); Trost, et al., "Palladium-Catalyzed Asymmetric Allylic α-Alkylation of Acyclic Ketones," J. Am. Chem. Soc. 127, 17180-17181 (2005); Trost, et al., "Asymmetric Allylic Alkylation of Cyclic Vinylogous Esters and Thioesters by Pd-Catalyzed Decarboxylation of Enol Carbonate and β-Ketoester Substrates," Angew. Chem., Int. Ed. 45, 3109-3112 (2006); Trost, et al., "Enantioselective Synthesis of α-Tertiary Hydroxyaldehydes by Palladium-Catalyzed Asymmetric Allylic Alkylation of Enolates."J. Am. Chem. Soc. 129, 282-283 (2007); Trost, et al., "Palladium-Catalyzed Decarboxylative Asymmetric Allylic Alkylation of Enol Carbonates," J. Am. Chem. Soc. 131, 18343-18357 (2009); Nakamura, et al., "Synthesis of Chiral α-Fluoroketones through Catalytic Enantioselective Decarboxylation," Angew. Chem., Int. Ed. 44, 7248-7251 (2005); Burger, et al., "Catalytic Asymmetric Synthesis of Cyclic α-Allylated α-Fluoroketones," Synlett 2824-2826 (2006); Bélanger, et al., "Enantioselective Pd-Catalyzed Allylation Reaction of Fluorinated Silyl Enol Ethers," J. Am. Chem. Soc. 129, 1034-1035 (2007); Schulz, et al., "Palladium-Catalyzed Synthesis of Substituted Cycloheptane-1,4-diones by an Asymmetric Ring-Expanding Allylation (AREA)," Angew. Chem., Int. Ed. 46, 3966-3970 (2007), the entire content of all of which are incorporated herein by reference.

According to embodiments of the present invention, a wide range of structurally-diverse, functionalized heteroatom containing compounds (e.g., nitrogen containing lactams and oxygen containing lactones) are prepared by a stereoselective method including palladium-catalyzed enantioselective enolate alkylation. This chemistry is important to the synthesis of bioactive alkaloids, and the transformation is useful for the construction of novel building blocks for medicinal and polymer chemistry. Indeed, in some embodiments of the present invention, these novel building blocks include heteroatom containing compounds useful as precursors to (or reactants leading to the preparation of) numerous biologically active and important natural and pharmaceutical products. While embodiments of the present invention are directed to the novel building blocks achieved from the transition-metal catalyzed allylic alkylation reaction, other embodiments of the present invention are directed to novel heteroatom containing substrates used in the transition-metal catalyzed allylic alkylation reaction to form the building blocks.

Indeed, in some embodiments of the present invention, a method of making a building block compound comprises reacting a substrate compound with a ligand in the presence of a palladium-based catalyst and a solvent. The palladium-based catalysts, ligands and solvents useful in this reaction are described in more detail below in the section entitled "Palladium-Catalyzed Decarboxylative Alkylation. The substrates used in the reaction, and the building block compounds made from the reaction are described here, and in the below sections entitled "Heteroatom Containing Substrate Compounds" and "Heteroatom Containing Building Block Compounds."

According to embodiments of the present invention compounds useful as either substrates for the creation of building blocks leading to target compounds or as building blocks include compounds represented by the following Chemical Formula A. As discussed here, these compounds can be used as substrate compounds useful in the method noted above and described in detail below. Also, these compounds may be used as reactants in other methods and reaction schemes to make other compounds, e.g., some naturally occurring compounds that may be biologically active.

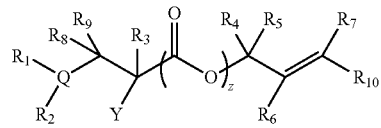

Chemical Formula A

In Chemical Formula A, z is either 0 or 1, and Q is a heteroatom, for example, N, O, P, S or a halogen such as Cl, I, Br or F. In some embodiments, for example, Q is N or O. Each of R1 through R10 is independently selected from hydrogen, substituted or unsubstituted hydrocarbyl groups, substituted or unsubstituted heteroatom containing hydrocarbyl groups, or functional groups. However, in some embodiments, R3 is not hydrogen. In some embodiments, in which z is 0 and R8 and R9 combine to form a carbonyl group (as discussed further below), R3 is also not phenyl or substituted phenyl. In yet other embodiments, in which z is 0 and R8 and R9 combine to form a carbonyl group (as discussed further below), R3 is not a simple carbonyl group. However, in some embodiments, R3 may be a substituted carbonyl group, e.g., a carbonyl group substituted hydrocarbyl group or heteroatom containing hydrocarbyl group or functional group. In some embodiments, though, R3 does not include any carbonyl groups, whether substituted or unsubstituted. In yet other embodiments, in which z is 0 and R8 and R9 combine to form a carbonyl group (as discussed further below), R3 is not an ethyl group. However, in some embodiments, R3 may be a substituted ethyl group, and R3 may be any other alkyl group (or other group as described above). In some embodiments, though, R3 is not an ethyl group or a substituted ethyl group. Also, in some embodiments, the carbon atom to which the R3 group is attached is a chiral, stereogenic center, i.e., R3 and Y are not the same.

Y may be selected from hydrogen, heteroatoms, substituted or unsubstituted hydrocarbyl groups, substituted or unsubstituted heteroatom containing hydrocarbyl groups, or functional groups. Additionally, any two or more adjacent R and Y groups can optionally combine to form a carbonyl group on the underlying atom. For example, in some embodiments, R8 and R9 combine to form a carbonyl group, as shown in the below Formula A(i).

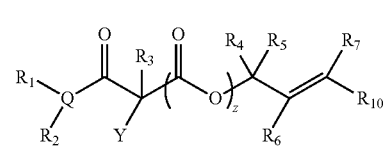

Formula A(i)

Also, any two or more adjacent R and Y groups can optionally combine to form a ring, e.g., a cyclic, heterocyclic, aryl or heteroaryl ring. Indeed, in some embodiments, although Formula 1 depicts an acyclic heteroatom containing compound, Formula 1 also encompasses cyclic, heterocyclic, aryl and heteroaryl compounds. Also, in some embodiments, while R6 and R10 may combine to form nearly any ring structure, R6 and R10 do not form a substituted or unsubstituted benzene ring. Similarly, in some embodiments, while R4 and R6 may combine to form nearly any ring structure, R4 and R6 do not form a substituted or unsubstituted benzene ring. In other embodiments, R6 and R10 do not form any aromatic ring, and R4 and R6 do not form any aromatic ring.

In embodiments in which R2 and Y combine to form a ring, in some embodiments, the atom in the ring directly adjacent the Q atom (i.e., the atom on the opposite side of the Q atom to the carbon atom carrying the R8 and R9 groups) is not a chiral center. More specifically, any substituents on that atom are the same as each other, and that atom does not include two different substituents.

For example, in some embodiments, the R2 group on the Q atom, and the Y group combine to form a ring with the Q atom, the carbon atom to which the Y group is attached, and the intervening carbon atom. The ring formed between the R2 group and the Y group can be any type of ring with any number of ring atoms. However, the ring formed from the combination of R2 and Y does not form a benzene ring or ortho-disubstituted benzene ring. In some embodiments, though, R2 and Y may form other substituted benzene rings. In other embodiments, however, R2 and Y do not form any kind of benzene ring.

In some exemplary embodiments, for example, the ring formed between the R2 group and the Y group may include one or more additional heteroatoms (i.e., additional to the Q atom depicted in Formula 1). In these embodiments, the compounds of Formula 1 may be represented by Formula B, below.

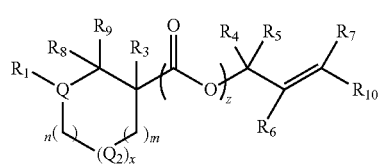

Formula B

In Formula B, z is 0 or 1, and R1 through R10 are the same as defined above with respect to Formula A. Each of Q1 and Q2 are as defined above with respect to Q1, and are each independently selected from heteroatoms, e.g., N, O, S, P or halogens, such as Cl, I, F or Br. In some embodiments, for example, each of Q1 and Q2 is independently selected from N or O. Additionally, similar to that described above with respect to Formulae 1 and 1(a), any two or more adjacent R groups can optionally combine to form a carbonyl group on the underlying atom. For example, in some embodiments, R8 and R9 combine to form a carbonyl group, as shown in the below Formula 2(a).

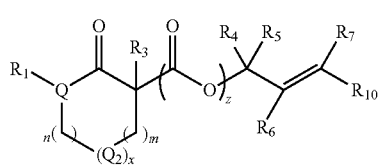

Formula B(i)

Also, in Formula B, each of x, n and m can be any integer of 0 or greater. When x is greater than 1, the plurality of Q2 heteroatoms may be the same as or different from each other. In some embodiments, for example, each of x, n and m is independently 0, 1, 2, 3 or 4. In some exemplary embodiments, when x and n are both 0, m may be 1, 2, 3 or 4. Conversely, when x and m are both 0, n may be 1, 2, 3 or 4. These configurations yield compounds having the Formulae B(ii) or B(iii) (where R8 and R9 combine to form a carbonyl group) below. Also, while m and n are defined here such that the ring depicted in Formula B has up to 7 ring atoms, it is understood that the size of the ring in Formula B is not particularly limited, and n and m can be any integers corresponding to any ring size. For example, in some embodiments, n and m are integers such that the resulting ring depicted in Formula B has from 3 to 12 ring atoms. In some embodiments for example, n and m are integers such that the resulting ring has from 3 to 10 ring atoms. In other embodiments, n and m are integers such that the resulting ring has from 5 to 7 ring atoms.

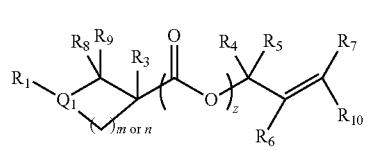

Formula B(ii)

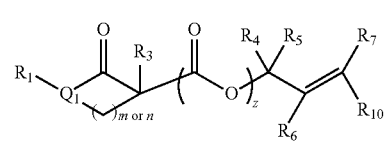

Formula B(iii)

Alternatively, in some embodiments, when x is 1, n and m may be any integer from 0 to 4 such that the sum of n and m may be 0, 1, 2 or 3. For example, in some embodiments, when x is 1, n may be 0 and m may be 0, 1, 2 or 3. In other embodiments, when x is 1, n may be 1 and m may be 0, 1 or 2. In still other embodiments, when x is 1, n may be 2 and m may be 0 or 1. In yet other embodiments, when x is 1, n may be 3 and m may be 0. Conversely, in some embodiments, when x is 1, m may be 0 and n may be 0, 1, 2 or 3. In other embodiments, when x is 1, m may be 1 and n may be 0, 1 or 2. In still other embodiments, when x is 1, m may be 2 and n may be 0 or 1. In yet other embodiments, when x is 1, m may be 3 and n may be 0. These configurations yield compounds of Formula B in which there are two heteroatoms, and include all configurations of the two heteroatoms on the ring. Specifically, these configurations cover every possible position of the second heteroatom (Q2) on the ring depicted in Formula B. Also, while m and n are defined here such that the ring depicted in Formula B has up to 7 ring atoms, it is understood that the size of the ring in Formula B is not particularly limited, and n and m can be any integers corresponding to any ring size, as discussed above. For example, in some embodiments, n and m are integers such that the resulting ring depicted in Formula B has from 3 to 12 ring atoms, for example 3 to 10 ring atoms or 5 to 7 ring atoms.

In some embodiments, the ring may include the Q atom depicted in Formulae A and B as the only heteroatom, and include any number of additional carbon atoms in the ring. Alternatively, however, the ring depicted in Formulae B and B(i) through B(iii) can have any number of heteroatoms positioned anywhere on the ring. For example, as shown in Formula B and B(i) above, the ring may include the heteroatom depicted in Formulae A and B separated from a group of one or more additional heteroatoms by one or more carbon atoms, or the ring may include two or more heteroatoms that are adjacent each other within the ring. However, according to other embodiments, the ring depicted in Formula B may include three or more heteroatoms which may be adjacent one another or separated from each other by at least one carbon atom. This configuration is depicted in Formulae B(iv) and B(v) (where R8 and R9 combine to form a carbonyl group) below.

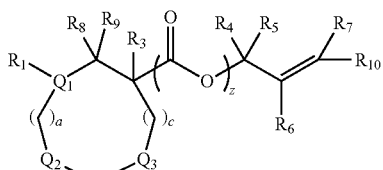

Formula B(iv)

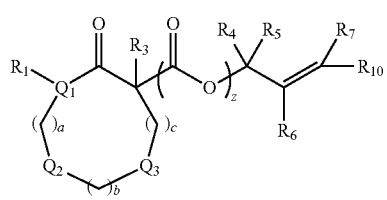

Formula B(v)

In Formula B(iv) and B(v), z is 0 or 1, each of Q1, Q2 and Q3 is as defined above with respect to Q1, and are each independently a heteroatom, for example, O, N, S, P, or a halogen such as Cl, I, Br or F. Each of R1 through R10 is also as described above with respect to Formulae A, B and B(i) through 2(iii). Each of a, b and c is independently an integer of 0 or greater. In some exemplary embodiments, each of a, b and c may be independently an integer of 0, 1 or 2. For example, in some embodiments, each of a, b and c is 0, yielding a five membered ring including three adjacent heteroatoms. In other embodiments, a is 1 and b and c are both 0, yielding a six membered ring in which Q2 and Q3 are adjacent one another and Q2 is separated from Q1 by a carbon atom. In still other embodiments, a is 2 and b and c are both 0, yielding a seven membered ring in which Q2 and Q3 are adjacent one another and Q2 is separated from Q1 by two carbon atoms.

According to other embodiments, b is 1 and a and c are both 0, yielding a six membered ring in which Q1 and Q2 are adjacent one another and Q2 is separated from Q3 by a carbon atom. In still other embodiments, b is 2 and a and c are both 0, yielding a seven membered ring in which Q1 and Q2 are adjacent one another and Q2 is separated from Q3 by two carbon atoms.

In other embodiments, c is 1 and a and b are both 0, yielding a six membered ring in which Q1, Q2 and Q3 are adjacent one another. In still other embodiments, c is 2 and a and b are both 0, yielding a seven membered ring in which Q1, Q2 and Q3 are adjacent one another. Also, while a, b and c are defined here such that the ring depicted in Formulae B, B(iv) and B(v) has up to 7 ring atoms, it is understood that the size of the ring in Formulae B, B(iv) and B(v) is not particularly limited, and a, b and c can be any integers corresponding to any ring size, as discussed above. For example, in some embodiments, a, b and c are integers such that the resulting ring depicted in Formulae B, B(iv) and B(v) has from 3 to 12 ring atoms, for example 3 to 10 ring atoms or 5 to 7 ring atoms.

In some exemplary embodiments, the ring depicted in Formula B may include four heteroatoms, and the four heteroatoms may be placed on the ring in any manner. For example, some of the heteroatoms may be spaced from each other by one or more ring carbon atoms while others are adjacent, or all heteroatoms may be adjacent each other, or all heteroatoms may be spaced from each other by one or more ring carbon atoms.

Additionally, although the rings discussed above are depicted and described as fully saturated, according to some embodiments of the present invention, any of the rings may be unsaturated (i.e., mono- or poly-unsaturated). To account for these compounds, the heteroatom containing substrate of Formula A may be represented by Formulae C or C(i) (where R8 and R9 combine to form a carbonyl group) below.

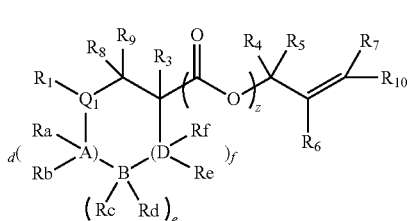

Formula C

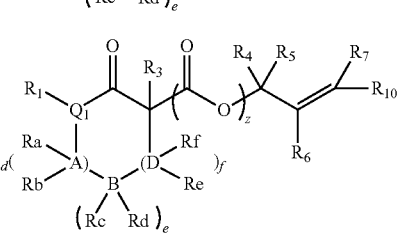

Formula C(i)

In Formulae C and C(i), z is 0 or 1, and Q1 and R1 through R10 are as defined above with respect to Formulae A, B and B(i) through B(v). Each of A, B and D is independently a carbon atom or a heteroatom. However, in some embodiments, in which d is 1 or greater, the A atom located directly adjacent the Q1 atom is not a chiral center. More specifically, the Ra and Rb substituents on that atom are the same as each other, and are not two different substituents. Also, the ring formed from Q1, A, B and D is not a benzene ring or an ortho-disubstituted benzene ring. In some embodiments, though, the ring may be any other substituted benzene ring. In other embodiments, however, the ring is not any kind of benzene ring.

Each of Ra, Rb, R, Rd, Re and Rf may be independently selected from hydrogen atoms, substituted or unsubstituted hydrocarbyl groups, substituted or unsubstituted heteroatom containing hydrocarbyl groups, halogens or functional groups. However, as discussed above, in some embodiments, in which d is 1 or greater, the A atom located directly adjacent the Q1 atom is not a chiral center, and the Ra and Rb substituents on that atom are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond. For example, R1 and one of the Ra groups may combine to form a double bond, or one of the Rb groups and one of the Rc groups may combine to form a double bond within the ring, or one of the Rd groups and one of the Re groups may combine to form a double bond within the ring. Any number of double bonds may be formed within the ring structure, and the ring structure may be heteroaryl in nature. Alternatively or additionally, two adjacent R groups on the same ring atom (e.g., Ra and Rb, or Rc and Rd, or Re and Rf) can combine to form a carbonyl group on the ring atom.

Each of d, e and f is independently an integer of 0 or greater, for example, an integer of 0, 1, 2, 3, or 4. When d, e or f is greater than 1, the plurality of A, B or D atoms, and the plurality of Ra, Rb, Rc, Rd, Re or Rf groups may be the same as or different from each other. Also, although Formulae C and C(i) above depict a six membered ring, it is understood from the definitions of d, e and f that the ring is not limited to six members, and can have any number of ring atoms, as discussed above with respect to Formulae A, B and B(i) through B(v). Indeed, in some embodiments, the ring has from 3 to 12 ring atoms, for example 3 to 10 ring atoms or 5 to 7 ring atoms.

Also, in the rings discussed above, any of the ring atoms, whether carbon or heteroatom, can be substituted with a substituted or unsubstituted hydrocarbyl group, substituted or unsubstituted heteroatom containing hydrocarbyl group, a halogen or a functional group. Indeed, although the rings depicted in Formulae B and B(i) through B(v) above are depicted with hydrogen atoms on each of the ring atoms, any or all of the hydrogen atoms on any or all of the ring atoms may be substituted with the substituents described above. As shown in Formula C, for example, each of the ring atoms (Q1, A, B and/or D) may include R groups that can be hydrogen, a substituted or unsubstituted hydrocarbyl group, a substituted or unsubstituted heteroatom containing hydrocarbyl group, a halogen or a functional group.

In some embodiments of the present invention, building block compounds created from substrate compounds of Formula A are represented by the below Formula D. The compounds of Formula D include compounds created by the palladium catalyzed decarboxylative alkylation of substrate compounds represented by Formula A in which z is 1, Q (or Q1) is O and R8 and R9 combine to form a carbonyl group.

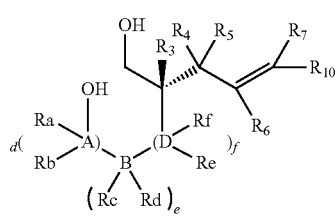

Formula D

As noted above, compounds of Formula D can be made through the palladium catalyzed decarboxylative alkylation of a lactone satisfying one of Formulae A, B or C above. Specifically, the compound of Formula D will result when a compound of Formula C (in which z is 1, Q1 is O and R8 and R9 combine to form a carbonyl group) is subjected to palladium catalyzed decarboxylative alkylation. In Formula D, A, B, D, Ra, Rb, Rc, Rd, Re, Rf, R3, R4, R5, R6, R7 and R10 are as described above with respect to A through C. Each of Ra, Rb, R, Rd, Re and Rf may be independently selected from hydrogen atoms, substituted or unsubstituted hydrocarbyl groups, substituted or unsubstituted heteroatom containing hydrocarbyl groups, halogens or functional groups. However, similar to that discussed above with respect to Formulae A through C, in some embodiments, in which d is 1 or greater, the A atom that is directly adjacent the OH group is not a chiral center. More specifically, the Ra and Rb groups on the A atom that is directly adjacent the OH group are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond.

In Formulae A, A(i), B, B(i) through B(v), C, C(i), and D above, the heteroatom containing compounds are depicted and described as including a terminal alkenyl group. This position of the alkenyl group may be important in the palladium catalyzed decarboxylative alkylation reaction. However, for other uses of the heteroatom containing compounds described here (e.g., as reactants in other reactions), the alkenyl group need not be positioned at the terminal end of the compound. Instead, the alkenyl group can be positioned elsewhere in the compound. Also, the position of the alkenyl group can be modified after the completion of the palladium catalyzed decarboxylative alkylation reaction. For example, in compounds of Formula A through C in which z is 0, the alkenyl group can be positioned as shown in the below Formulae A(ii) and A(iii) (where R8 and R9 combine to form a carbonyl group) in which z is 0.

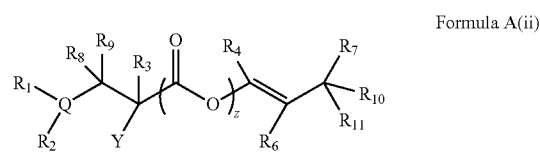

Formula A(ii)

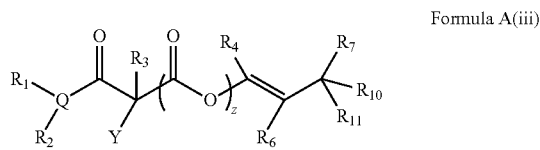

Formula A(iii)

In Formula A(ii) and A(iii), Q, Y and R1 through R10 are as described above with respect to Formulae 1, 2, 2(a), 2(b) and 3. However, in Formulae A(ii) and A(iii), z is 0. Also, R11 is selected from the same substituents described above for R1 through R10. Specifically, each of R1 through R11 may be independently selected from hydrogen, substituted or unsubstituted hydrocarbyl groups, substituted or unsubstituted heteroatom containing hydrocarbyl groups, halogens or functional groups.

In other embodiments, in which the compound is analogous to the compound represented by Formula D, the alkenyl group can be positioned as shown in the below Formula D(i).

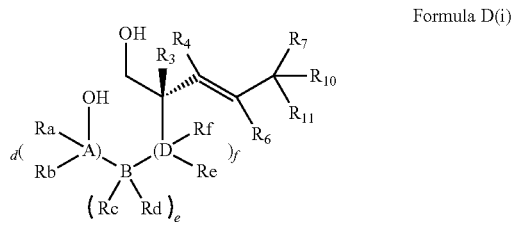

Formula D(i)

In Formula D(i), A, B, D, Ra through Rf, d, e, f, and R3 through R10 are as described above. Also, R11 is selected from the same substituents described above for R1 through R10. Specifically, each of R1 through R11 may be independently selected from hydrogen, substituted or unsubstituted hydrocarbyl groups, substituted or unsubstituted heteroatom containing hydrocarbyl groups, halogens or functional groups. Each of Ra, Rb, Rc, Rd, Re and Rf may be independently selected from hydrogen atoms, substituted or unsubstituted hydrocarbyl groups, substituted or unsubstituted heteroatom containing hydrocarbyl groups, halogens or functional groups. However, similar to that discussed above with respect to Formulae A through C, in some embodiments, in which d is 1 or greater, the A atom that is directly adjacent the OH group is not a chiral center. More specifically, the Ra and Rb groups on the A atom that is directly adjacent the OH group are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond.

In Formulae A, A(i), B, B(i) through B(v), C, C(i), and D above, the terminal alkenyl group can be reacted (e.g., hydrogenated) to make a corresponding alkyl derivative having the below Formula A(iv) and A(v) (in which the R8 and R9 groups combine to form a carbonyl group, and in which z is 0.

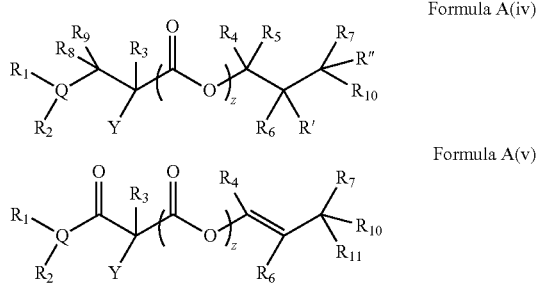

Formula A(iv)

Formula A(v)

In Formula A(iv) and A(v), Q, Y and R1 through R11 are as described above with respect to Formulae A through C. Also, R' and R" are independently selected from the same substituents described above for R1 through R11. Specifically, each of R1 through R11 and R' and R" may be independently selected from hydrogen, substituted or unsubstituted hydrocarbyl groups, substituted or unsubstituted heteroatom containing hydrocarbyl groups, halogens or functional groups. Also, it is understood that although Formula A through C are discussed and depicted above as including the terminal alkenyl group, any of those formulae may instead include the terminal alkyl discussed here and depicted in Formulae A(iv) and A(v).

In some embodiments of the present invention in which the heteroatom is a nitrogen atom, the R group on the heteroatom (i.e., Q, Q1, Q2, Q3, or other heteroatoms in the substrates of Formulae A through C) can be an amine protecting group. Those of ordinary skill in the art would readily understand what is meant by "amine protecting group." However, some nonlimiting examples of suitable amine protecting groups include carboxybenzyl (Cbz) groups, p-methoxybenzyl carbonyl (Moz or MeOZ) groups, tert-butyloxycarbonyl (BOC) groups, fluorenylmethyloxycarbonyl (FMOC) groups, acetyl (Ac) groups, benzoyl (Bz) groups, benzyl (Bn) groups, carbamate groups, p-methoxybenzyl (PMB) groups, dimethoxybenzyl (DMPM) groups, p-methoxyphenyl (PMP) groups, tosyl (Ts) groups, sulfonamide (Nosyl & Nps) groups, methoxybenzoyl groups (OMe-Bz), and fluorobenzoyl groups (F-Bz). For example, in some embodiments, the amine protecting group is selected from tosyl groups (Ts), butyloxycarbonyl groups (BOC), carbobenzyloxy groups (Cbz), fluorenylmethyloxycarbonyl groups (FMOC), acetyl groups (Ac), methoxybenzoyl groups (OMe-Bz), fluorobenzoyl groups (F-Bz), and benzoyl groups (Bz).

In some alternate embodiments, however, the R group(s) on the N can be hydrogen, a substituted or unsubstituted hydrocarbyl group, a substituted or unsubstituted heteroatom containing hydrocarbyl group, or a functional group. For example, in some embodiments, the R group(s) on the N atom may be H or OH. In some exemplary embodiments, for example, z is 0 and R1 is H or OH.

As used herein, the term "hydrocarbyl groups" refers to univalent hydrocarbon radicals containing from 1 to 30 carbon atoms, for example, from 1 to 24 carbon atoms or 1 to 12 carbon atoms. The term "hydrocarbyl groups" includes linear, branched, cyclic, saturated and unsaturated species, for example, alkyl groups, alkenyl groups, alkynyl groups, aryl groups, and the like. Also, as used herein, the term "substituted," as in "substituted hydrocarbyl groups," refers to a hydrocarbyl group in which one or more hydrogen atoms (bonded to a carbon atom) is replaced with one or more non-hydrogen functional groups.

The term "functional groups" would be readily understood to those of ordinary skill in the art. However, some nonlimiting examples of suitable functional groups for use in the Formulae and substrates described above include halogens, hydroxyl groups, sulfhydryl groups, alkoxy groups (e.g., having from 1 to 24 carbon atoms), alkenyloxy groups (e.g., having from 2 to 24 carbon atoms), alkynyloxy groups (e.g., having from 2 to 24 carbon atoms), aryloxy groups (e.g., having from 5 to 24 carbon atoms), acyl groups including alkylcarbonyl groups of the formula —CO-alkyl (e.g., having from 2 to 24 carbon atoms) and arylcarbonyl groups of the formula —CO-aryl (e.g., having from 6 to 24 carbon atoms), acyloxy groups having the formula —O-acyl, alkoxycarbonyl groups having the formula —(CO)—O-alkyl (e.g., having from 2 to 24 carbon atoms), carbonyl groups (including aldehyde moieties having the formula —(CO)—H) and ketone moieties having the formula —(CO)—R where R is any hydrocarbyl group), aryloxycarbonyl groups having the formula —(CO)—O-aryl (e.g., having from 6 to 24 carbon atoms), halocarbonyl groups having the formula —CO—X (where X is a halogen), alkylcarbonato groups having the formula —O—(CO)—O-alkyl (e.g., having from 2 to 24 carbon atoms), arylcarbonato groups having the formula —O—(CO)—O-aryl (e.g., having from 6 to 24 carbon atoms), carboxyl groups having the formula —COOH, carboxylato groups having the formula —COO⁻, carbamoyl groups having the formula —(CO)—NH, mono-alkyl substituted carbamoyl groups having the formula —(CO)—NH-alkyl (e.g., the alkyl group having from 1 to 24 carbon atoms), di-alkyl substituted carbamoyl groups having the formula —(CO)—N-alkyl$_2$ (e.g., each alkyl group having from 1 to 24 carbon atoms), mono-aryl substituted carbamoyl groups having the formula —(CO)—NH-aryl (e.g., the aryl group having from 6 to 24 carbon atoms), di-aryl substituted carbamoyl groups having the formula —(CO)—N-aryl$_2$ (e.g., each aryl group having from 6 to 24 carbon atoms), di-N(alkyl)-N(aryl) substituted carbamoyl groups having the formula —(CO)—N-(alkyl)(aryl), thiocarbamoyl groups having the formula —(CS)—NH$_2$, carbamido groups having the formula —NH—(CO)—NH$_2$, cyano groups, isocyano groups, cyanato groups, isocyanato groups, isothiocyanato groups, azido groups, formyl groups, thioformyl groups, amino groups, mono-alkyl substituted amino groups (e.g., the alkyl group having from 1 to 24 carbon atoms), di-alkyl substituted amino groups (e.g., the alkyl group having from 1 to 24 carbon atoms), mono-aryl substituted amino groups (e.g., the aryl group having from 6 to 24 carbon atoms), di-aryl substituted amino groups (e.g., each aryl group having from 6 to 24 carbon atoms), alkylamido groups having the formula —NH—(CO)-alkyl (e.g., having from 2 to 24 carbon atoms), arylamido groups having the formula —NH—(CO)-aryl (e.g., having from 6 to 24 carbon atoms), imino groups having the formula —CR═NH (where R is hydrogen, alkyl, aryl, alkaryl, aralkyl, etc.), alkyl imino groups having the formula —CR═N-alkyl (where R is hydrogen, alkyl, aryl, aralkyl, alkaryl, etc.), aryl imino groups having the formula —CR═N-aryl (where R is hydrogen, alkyl, aryl, aralkyl, alkaryl, etc.), nitro groups, nitroso groups having the formula —NO, sulfo groups having the formula —SO$_2$—OH, sulfonato groups having the formula —SO$_2$—O$^-$, alkylsulfanyl groups having the formula —S-alkyl (also called, interchangeably, alkylthio groups), arylsulfanyl groups having the formula —S-aryl (also called, interchangeably arylthio groups), alkylsulfinyl groups having the formula —(SO)-alkyl, arylsulfinyl groups having the formula —(SO)-aryl, alkylsulfonyl groups having the formula —SO$_2$-alkyl, arylsulfonyl groups having the formula —SO$_2$-aryl, boryl groups having the formula —BH$_2$, borono groups having the formula —B(OH)$_2$, boronato groups having the formula —B(OR)$_2$ (where R is alkyl or another hydrocarbyl group), phosphono groups having the formula —P(O)(OH)$_2$, phosphonato groups having the formula —P(O)(O$^-$)$_2$, phosphinato groups having the formula —P(O)(O$^-$), phospho groups having the formula —PO$_2$, and phosphino groups having the formula —PH$_2$.

In addition to, or instead of, being substituted with a functional group, the substituted species may be substituted with hydrocarbyl groups, for example, alkyl groups (e.g., having from 1 to 24 carbon atoms, or from 1 to 12 carbon atoms, or from 1 to 6 carbon atoms), alkenyl groups (e.g., having from 2 to 24 carbon atoms, or from 2 to 13 carbon atoms, or from 2 to 6 carbon atoms), alkynyl groups (e.g., having from 2 to 24 carbon atoms, or from 2 to 12 carbon atoms, or from 2 to 6 carbon atoms), aryl groups (e.g., having from 5 to 24 carbon atoms, or from 5 to 14 carbon atoms), alkaryl groups (i.e., aryl with an alkyl substituent, e.g., having from 6 to 24 carbon atoms, or from 6 to 16 carbon atoms), and/or aralkyl groups (i.e., alkyl with an aryl substituent, e.g., having from 6 to 24 carbon atoms, or from 6 to 16 carbon atoms). Also, any of the functional groups or hydrocarbyl group substituents may be further substituted (if the group permits) with one or more additional functional groups or hydrocarbyl groups.

Nonlimiting examples of compounds satisfying the above formulae include heteroatom containing substrates, and heteroatom containing building blocks, both of which are described in more detail below.

Heteroatom Containing Substrates

As discussed above, transition metal-catalyzed allylic alkylation can be used for the enantioselective preparation of chiral substances. According to embodiments of the present invention, heteroatom containing substrates useful in the transition metal-catalyzed allylic alkylation reaction include cyclic and acyclic heteroatom containing compounds represented by Formula 1.

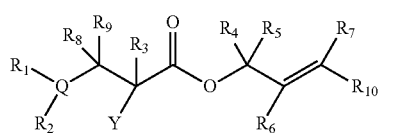

Formula 1

In Formula 1, Q is a heteroatom, for example, N, O, P, S or a halogen such as Cl, I, Br or F. In some embodiments, for example, Q is N or O. Each of R1 through R10 is independently selected from hydrogen, substituted or unsubstituted hydrocarbyl groups, substituted or unsubstituted heteroatom containing hydrocarbyl groups, or functional groups. However, in some embodiments, R3 is not hydrogen. In some embodiments, in which R8 and R9 combine to form a carbonyl group (as discussed below), R3 is also not phenyl or substituted phenyl. In yet other embodiments, in which R8 and R9 combine to form a carbonyl group (as discussed below), R3 is not a simple carbonyl group. However, in some embodiments, in which R8 and R9 combine to form a carbonyl group (as discussed below), R3 may be a substituted carbonyl group, e.g., a carbonyl group substituted hydrocarbyl group or heteroatom containing hydrocarbyl group or functional group. In some embodiments, though, R3 does not include any carbonyl groups, whether substituted or unsubstituted. In yet other embodiments, in which R8 and R9 combine to form a carbonyl group (as discussed below), R3 is not an ethyl group. However, in some embodiments, R3 may be a substituted ethyl group, and R3 may be any other alkyl group (or other group as described above). In some embodiments, though, R3 is not an ethyl group or a substituted ethyl group. Also, in some embodiments, the carbon atom to which the R3 group is attached is a chiral, stereogenic center, i.e., R3 and Y are not the same.

Y may be selected from hydrogen, heteroatoms, substituted or unsubstituted hydrocarbyl groups, substituted or unsubstituted heteroatom containing hydrocarbyl groups, or functional groups. Additionally, any two or more adjacent R and Y groups can optionally combine to form a carbonyl group on the underlying atom. For example, in some embodiments, R8 and R9 combine to form a carbonyl group, as shown in the below Formula 1(a).

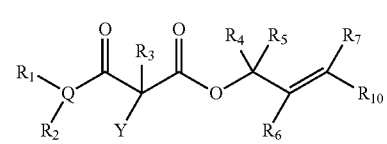

Formula 1(a)

Also, any two or more adjacent R and Y groups can optionally combine to form a ring, e.g., a cyclic, heterocyclic, aryl or heteroaryl ring. Indeed, in some embodiments, although Formula 1 depicts an acyclic heteroatom containing compound, Formula 1 also encompasses cyclic, heterocyclic, aryl and heteroaryl compounds. Also, in some embodiments, while R6 and R10 may combine to form nearly any ring structure, R6 and R10 do not form a substituted or unsubstituted benzene ring. In some embodiments, R6 and R10 do not form any aromatic ring. Similarly, in some embodiments, while R4 and R6 may combine to form nearly any ring structure, R4 and R6 do not form a substituted or unsubstituted benzene ring. In some embodiments, R4 and R6 do not form any aromatic ring.

In embodiments in which R2 and Y combine to form a ring, in some embodiments, the atom in the ring directly adjacent the Q atom (i.e., the atom on the opposite side of the Q atom to the carbon atom carrying the R8 and R9 groups) is not a chiral center. More specifically, any substituents on that atom are the same as each other, and that atom does not include two different substituents.

For example, in some embodiments, the R2 group on the Q atom, and the Y group combine to form a ring with the Q atom, the carbon atom to which the Y group is attached, and the intervening carbon atom. The ring formed between the R$_2$ group and the Y group can be any type of ring with any number of ring atoms. However, the ring formed from the combination of R2 and Y does not form a benzene ring or ortho-disubstituted benzene ring. In some embodiments, though, R2 and Y may form other substituted benzene rings. In other embodiments, however, R2 and Y do not form any kind of benzene ring.

In some exemplary embodiments, for example, the ring formed between the R2 group and the Y group may include one or more additional heteroatoms (i.e., additional to the Q atom depicted in Formula 1). In these embodiments, the compounds of Formula 1 may be represented by Formula 2, below.

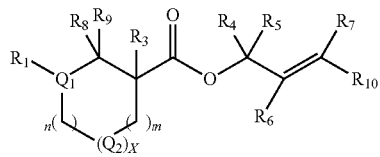

Formula 2

In Formula 2, R1 through R10 are the same as defined above with respect to Formula 1. Each of Q1 and Q2 are as defined above with respect to Q1, and are each independently selected from heteroatoms, e.g., N, O, S, P or halogens, such as Cl, I, F or Br. In some embodiments, for example, each of Q1 and Q2 is independently selected from N or O. Additionally, similar to that described above with respect to Formulae 1 and 1(a), any two or more adjacent R groups can optionally combine to form a carbonyl group on the underlying atom. For example, in some embodiments, R8 and R9 combine to form a carbonyl group, as shown in the below Formula 2(a).

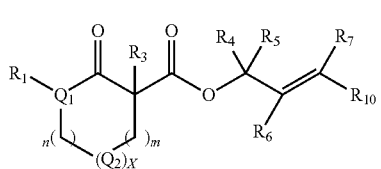

Formula 2(a)

Also, in Formula 2, each of x, n and m can be any integer of 0 or greater. When x is greater than 1, the plurality of Q2 heteroatoms may be the same as or different from each other. In some embodiments, for example, each of x, n and m is independently 0, 1, 2, 3 or 4. In some exemplary embodiments, when x and n are both 0, m may be 1, 2, 3 or 4. Conversely, when x and m are both 0, n may be 1, 2, 3 or 4. These configurations yield compounds having the Formulae 2(b) or 2(c) (where R8 and R9 combine to form a carbonyl group) below. Also, while m and n are defined here such that the ring depicted in Formula 2 has up to 7 ring atoms, it is understood that the size of the ring in Formula 2 is not particularly limited, and n and m can be any integers corresponding to any ring size. For example, in some embodiments, n and m are integers such that the resulting ring depicted in Formula 2 has from 3 to 12 ring atoms. In some embodiments for example, n and m are integers such that the resulting ring has from 3 to 10 ring atoms. In other embodiments, n and m are integers such that the resulting ring has from 5 to 7 ring atoms.

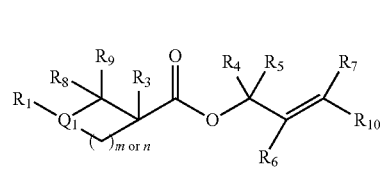

Formula 2(b)

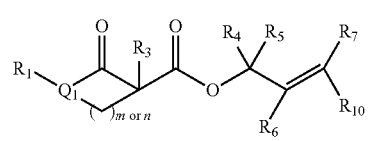

Formula 2(c)

Alternatively, in some embodiments, when x is 1, n and m may be any integer from 0 to 4 such that the sum of n and m may be 0, 1, 2 or 3. For example, in some embodiments, when x is 1, n may be 0 and m may be 0, 1, 2 or 3. In other embodiments, when x is 1, n may be 1 and m may be 0, 1 or 2. In still other embodiments, when x is 1, n may be 2 and m may be 0 or 1. In yet other embodiments, when x is 1, n may be 3 and m may be 0. Conversely, in some embodiments, when x is 1, m may be 0 and n may be 0, 1, 2 or 3. In other embodiments, when x is 1, m may be 1 and n may be 0, 1 or 2. In still other embodiments, when x is 1, m may be 2 and n may be 0 or 1. In yet other embodiments, when x is 1, m may be 3 and n may be 0. These configurations yield compounds of Formula 2 in which there are two heteroatoms, and cover all configurations of the two heteroatoms. Specifically, these configurations cover every possible position of the second heteroatom (Q2) on the ring depicted in Formula 2. Also, while m and n are defined here such that the ring depicted in Formula 2 has up to 7 ring atoms, it is understood that the size of the ring in Formula 2 is not particularly limited, and n and m can be any integers corresponding to any ring size, as discussed above. For example, in some embodiments, n and m are integers such that the resulting ring depicted in Formula 2 has from 3 to 12 ring atoms, for example 3 to 10 ring atoms or 5 to 7 ring atoms.

In some embodiments, the ring may include the Q atom depicted in Formulae 1 and 2 as the only heteroatom, and include any number of additional carbon atoms in the ring. Alternatively, however, the ring depicted in Formulae 2 and 2(a) through 2(c) can have any number of heteroatoms positioned anywhere on the ring. For example, as shown in Formula 2 and 2(a) above, the ring may include the heteroatom depicted in Formulae 1 and 2 separated from a group of one or more additional heteroatoms by one or more carbon atoms, or the ring may include two or more heteroatoms that are adjacent each other within the ring. However, according to other embodiments, the ring depicted in Formula 2 may include three or more heteroatoms which may be adjacent one another or separated from each other by at least one carbon atom. This configuration is depicted in Formulae 2(d) and 2(e) (where R8 and R9 combine to form a carbonyl group) below.

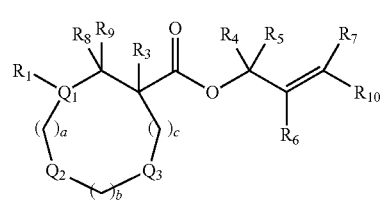

Formula 2(d)

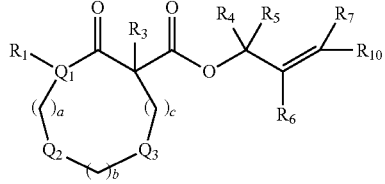

Formula 2(e)

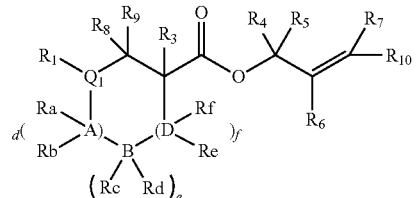

Formula 3

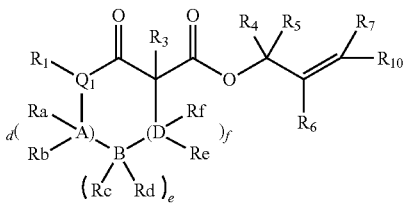

Formula 3(a)

In Formula 2(d) and 2(e), each of Q1, Q2 and Q3 is as defined above with respect to Q1, and are each independently a heteroatom, for example, O, N, S, P, or a halogen such as Cl, I, Br or F. Each of R1 through R10 is also as described above with respect to Formulae 1, 2 and 2(a) through 2(c). Each of a, b and c is independently an integer of 0 or greater. In some exemplary embodiments, each of a, b and c may be independently an integer of 0, 1 or 2. For example, in some embodiments, each of a, b and c is 0, yielding a five membered ring including three adjacent heteroatoms. In other embodiments, a is 1 and b and c are both 0, yielding a six membered ring in which Q2 and Q3 are adjacent one another and Q2 is separated from Q1 by a carbon atom. In still other embodiments, a is 2 and b and c are both 0, yielding a seven membered ring in which Q2 and Q3 are adjacent one another and Q2 is separated from Q1 by two carbon atoms.

According to other embodiments, b is 1 and a and c are both 0, yielding a six membered ring in which Q1 and Q2 are adjacent one another and Q2 is separated from Q3 by a carbon atom. In still other embodiments, b is 2 and a and c are both 0, yielding a seven membered ring in which Q1 and Q2 are adjacent one another and Q2 is separated from Q3 by two carbon atoms.

In other embodiments, c is 1 and a and b are both 0, yielding a six membered ring in which Q1, Q2 and Q3 are adjacent one another. In still other embodiments, c is 2 and a and b are both 0, yielding a seven membered ring in which Q1, Q2 and Q3 are adjacent one another. Also, while a, b and c are defined here such that the ring depicted in Formulae 2, 2(d) and 2(e) has up to 7 ring atoms, it is understood that the size of the ring in Formulae 2, 2(d) and 2(e) is not particularly limited, and a, b and c can be any integers corresponding to any ring size, as discussed above. For example, in some embodiments, a, b and c are integers such that the resulting ring depicted in Formulae 2, 2(d) and 2(e) has from 3 to 12 ring atoms, for example 3 to 10 ring atoms or 5 to 7 ring atoms.

In some exemplary embodiments, the ring depicted in Formula 2 may include four heteroatoms, and the four heteroatoms may be placed on the ring in any manner. For example, some of the heteroatoms may be spaced from each other by one or more ring carbon atoms while others are adjacent, or all heteroatoms may be adjacent each other, or all heteroatoms may be spaced from each other by one or more ring carbon atoms.

Additionally, although the rings discussed above are depicted and described as fully saturated, according to some embodiments of the present invention, any of the rings may be unsaturated (i.e., mono- or poly-unsaturated). To account for these compounds, the heteroatom containing substrate of Formula 1 may be represented by Formulae 3 or 3(a) (where R8 and R9 combine to form a carbonyl group) below.

In Formulae 3 and 3(a), Q1 and R1 through R10 are as defined above with respect to Formulae 1, 2 and 2(a) through 2(e). Each of A, B and D is independently a carbon atom or a heteroatom. However, in some embodiments, in which d is 1 or greater, the A atom located directly adjacent the Q1 atom is not a chiral center. More specifically, the Ra and Rb substituents on that atom are the same as each other, and are not two different substituents. Also, the ring formed from Q1, A, B and D is not a benzene ring or an ortho-disubstituted benzene ring. In some embodiments, though, the ring may be any other substituted benzene ring. In other embodiments, however, the ring is not any kind of benzene ring.

Each of Ra, Rb, R, Rd, Re and Rf may be independently selected from hydrogen atoms, substituted or unsubstituted hydrocarbyl groups, substituted or unsubstituted heteroatom containing hydrocarbyl groups, halogens or functional groups. However, as discussed above, in some embodiments, in which d is greater than 1, the A atom located directly adjacent the Q1 atom is not a chiral center, and the Ra and Rb substituents on that atom are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond. For example, R1 and one of the Ra groups may combine to form a double bond, one of the Rb groups and one of the Rc groups may combine to form a double bond within the ring, or one of the Rd groups and one of the Re groups may combine to form a double bond within the ring. Any number of double bonds may be formed within the ring structure, and the ring structure may be heteroaryl in nature. Alternatively or additionally, two adjacent R groups on the same ring atom (e.g., Ra and Rb, or Rc and Rd, or Re and Rf) can combine to form a carbonyl group on the ring atom. Each of d, e and f is independently an integer of 0 or greater, for example, an integer of 0, 1, 2, 3, or 4. When d, e or f is greater than 1, the plurality of A, B or D atoms, and the plurality of Ra, Rb, Rc, Rd, Re or Rf groups may be the same as or different from each other. Also, although Formulae 3 and 3(a) above depict a six membered ring, it is understood from the definitions of d, e and f that the ring is not limited to six members, and can have any number of ring atoms, as discussed above with respect to Formulae 1, 2 and 2(a) through 2(e). Indeed, in some embodiments, the ring has from 3 to 12 ring atoms, for example 3 to 10 ring atoms or 5 to 7 ring atoms.

Also, in the rings discussed above, any of the ring atoms, whether carbon or heteroatom, can be substituted with a substituted or unsubstituted hydrocarbyl group, substituted or unsubstituted heteroatom containing hydrocarbyl group, a halogen or a functional group. Indeed, although the rings depicted in Formulae 2 and 2(a) through 2(e) above are depicted with hydrogen atoms on each of the ring atoms, any or all of the hydrogen atoms on any or all of the ring atoms may be substituted with the substituents described above. As shown in Formula 3, for example, each of the ring atoms (Q1, A, B and/or D) may include R groups that can be hydrogen, a substituted or unsubstituted hydrocarbyl group, a substituted or unsubstituted heteroatom containing hydrocarbyl group, a halogen or a functional group.

In Formulae 1, 1(a), 2, 2(a) through 2(b), 3 and 3(a) above, the heteroatom containing substrates are depicted and described as including a terminal alkenyl group. This position of the alkenyl group may be important for the palladium catalyzed decarboxylative alkylation reaction used to create the building blocks described below. However, for other uses of the heteroatom containing substrates described here (e.g., as reactants in other reactions), the alkenyl group need not be positioned at the terminal end of the compound. Instead, the alkenyl group can be positioned elsewhere in the compound. For example, the alkenyl group can be positioned as shown in the below Formulae 1(b) and 1(c) (where R8 and R9 combine to form a carbonyl group).

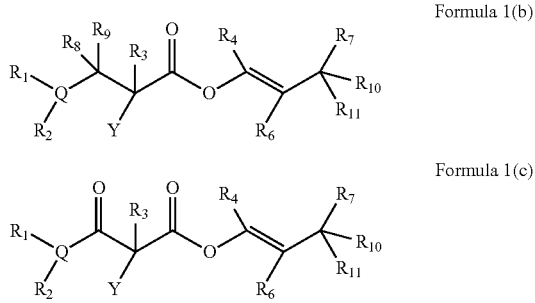

Formula 1(b)

Formula 1(c)

In Formula 1(a), Q, Y and R1 through R10 are as described above with respect to Formulae 1, 2, 2(a), 2(b) and 3. Also, R11 is selected from the same substituents described above for R1 through R9. Specifically, each of R1 through R10 may be independently selected from hydrogen, substituted or unsubstituted hydrocarbyl groups, substituted or unsubstituted heteroatom containing hydrocarbyl groups, halogens or functional groups.

In Formulae 1 through 3 above, the terminal alkenyl group can be reacted (e.g., hydrogenated) to make a corresponding alkyl derivative having the below Formula 1(d) and 1(e) (in which the R8 and R9 groups combine to form a carbonyl group, and in which z is 0.

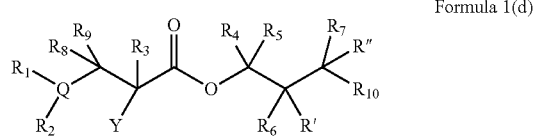

Formula 1(d)

-continued

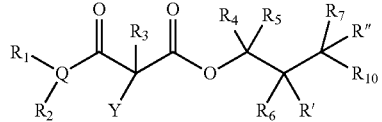

Formula 1(e)

In Formula 1(d) and 1(e), Q, Y and R1 through R11 are as described above with respect to Formulae A through C. Also, R' and R" are independently selected from the same substituents described above for R1 through R11. Specifically, each of R1 through R11 and R' and R" may be independently selected from hydrogen, substituted or unsubstituted hydrocarbyl groups, substituted or unsubstituted heteroatom containing hydrocarbyl groups, halogens or functional groups. Also, it is understood that although Formula 1 through 3 are discussed and depicted above as including the terminal alkenyl group, any of those formulae may instead include the terminal alkyl discussed here and depicted in Formulae 1(d) and 1(e).

In some embodiments of the present invention in which the heteroatom is a nitrogen atom, the R group on the heteroatom (i.e., Q, Q1, Q2, Q3, or other heteroatoms in the substrates of Formulae 1 through 3) can be an amine protecting group. Those of ordinary skill in the art would readily understand what is meant by "amine protecting group." However, some nonlimiting examples of suitable amine protecting groups include carbobenzyloxy (Cbz) groups, p-methoxybenzyl carbonyl (Moz or MeOZ) groups, tert-butyloxycarbonyl (BOC) groups, fluorenylmethyloxycarbonyl (FMOC) groups, acetyl (Ac) groups, benzoyl (Bz) groups, benzyl (Bn) groups, carbamate groups, p-methoxybenzyl (PMB) groups, dimethoxybenzyl (DMPM) groups, p-methoxyphenyl (PMP) groups, tosyl (Ts) groups, sulfonamide (Nosyl & Nps) groups, methoxybenzoyl groups (OMe-Bz), and fluorobenzoyl groups (F-Bz). For example, in some embodiments, the amine protecting group is selected from tosyl groups (Ts), butyloxycarbonyl groups (BOC), carbobenzyloxy groups (Cbz), fluorenylmethyloxycarbonyl groups (FMOC), acetyl groups (Ac), methoxybenzoyl groups (OMe-Bz), fluorobenzoyl groups (F-Bz), and benzoyl groups (Bz).

Also, the substrate compounds are generally racemic, i.e., an equimolar mixture of the (+) and (−) enantiomers of the compound. However, in some embodiments, the substrates may be enantioenriched compounds in which one of the (+) or (−) enantiomers is present in an enantiomeric excess. Indeed, as used herein, the term "enantionriched" refers to an enantiomeric excess of the particular enantiomer of the compound. Specifically, the substrate compounds according to some embodiments of the present invention include on eof (+) or (−) enantiomers in an enantiomeric excess, thus creating an "enantioenriched" substrate compound. In some embodiments, for example, the enantioenriched substrate compound may include one of the (+) or (−) enantiomers in an enantiomeric excess of greater than 50%, for example, about 60% or greater, or about 70% or greater, or about 80% or greater According to some embodiments, the enantioenriched substrate compound may include one of the (+) or (−) enantiomers in an enantiomeric excess of about 90% or greater. In other embodiments, the enantioenriched substrate compound may include one of the (+) or (−) enantiomers in an enantiomeric excess of about 90% to about 99%.

Some nonlimiting examples of substrates satisfying the above formulae, according to embodiments of the present invention, include the compounds depicted below. It is understood that although some of the nitrogen atoms in some of the nitrogen containing-compounds listed below include protecting groups, the nitrogen atoms do not necessarily include a protecting group. Indeed, in some embodiments of the present invention, a hydrogen atom is attached to the nitrogen atom. In each of the examples listed below, the protecting group on any of the nitrogen atoms can be replaced with a hydrogen atom.

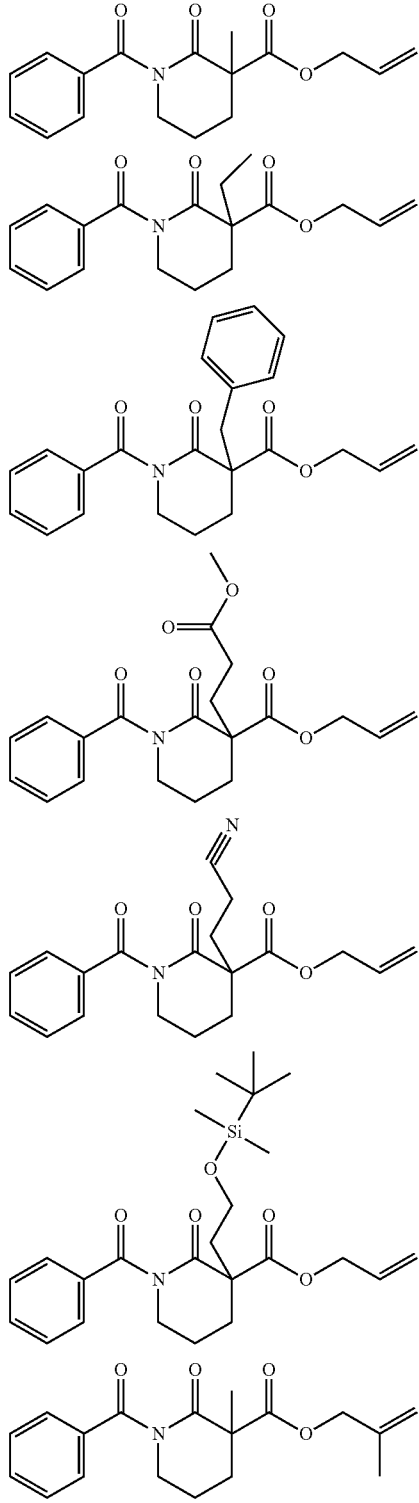

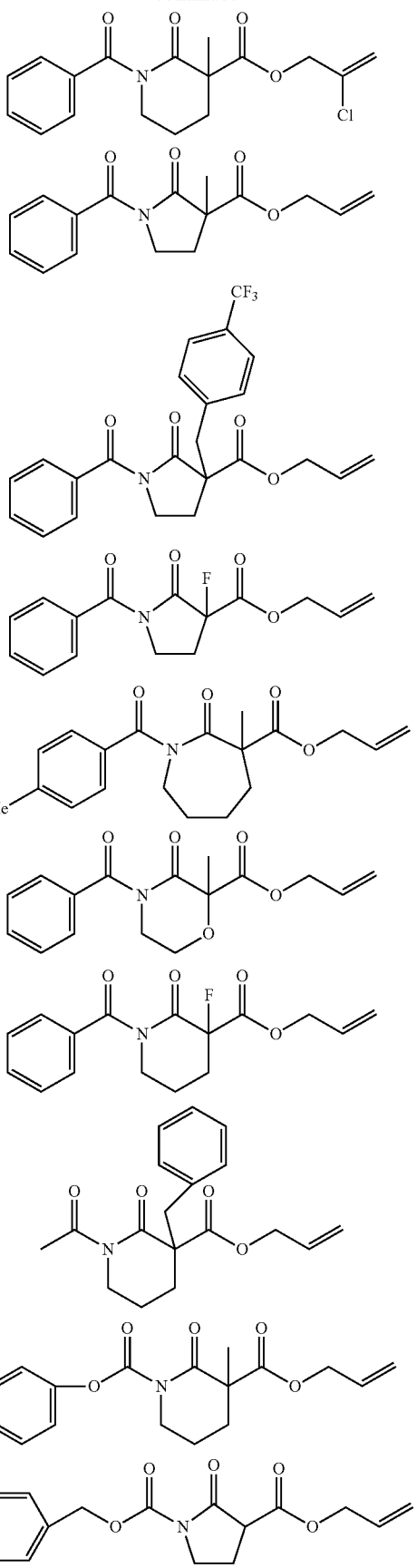

27
-continued
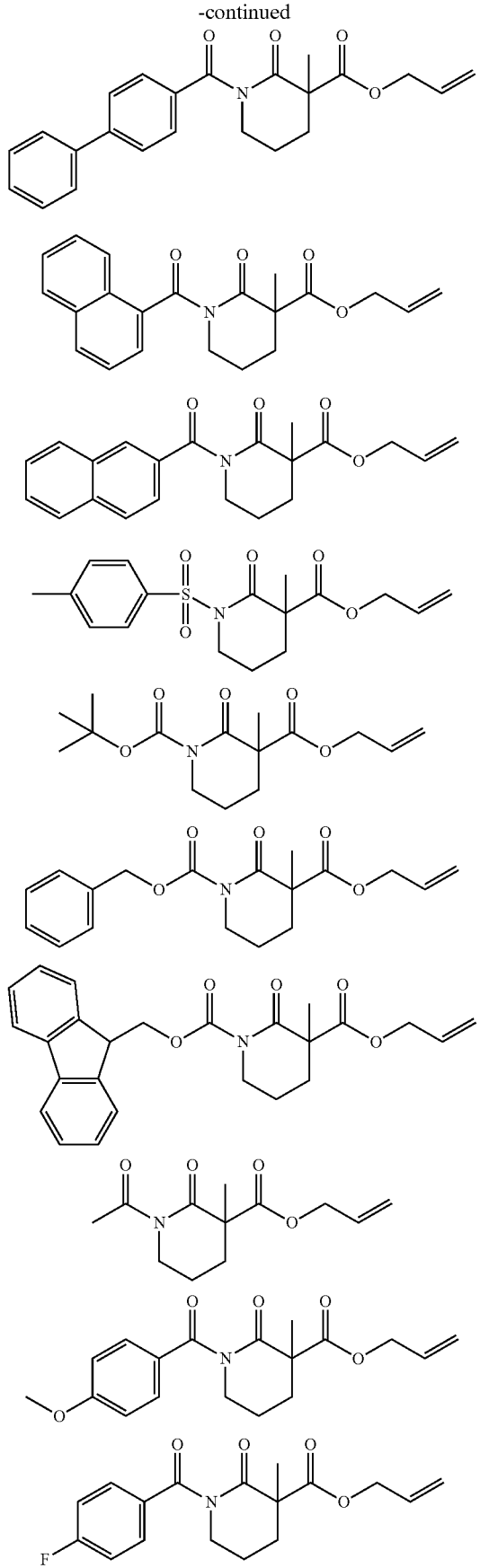
28
-continued
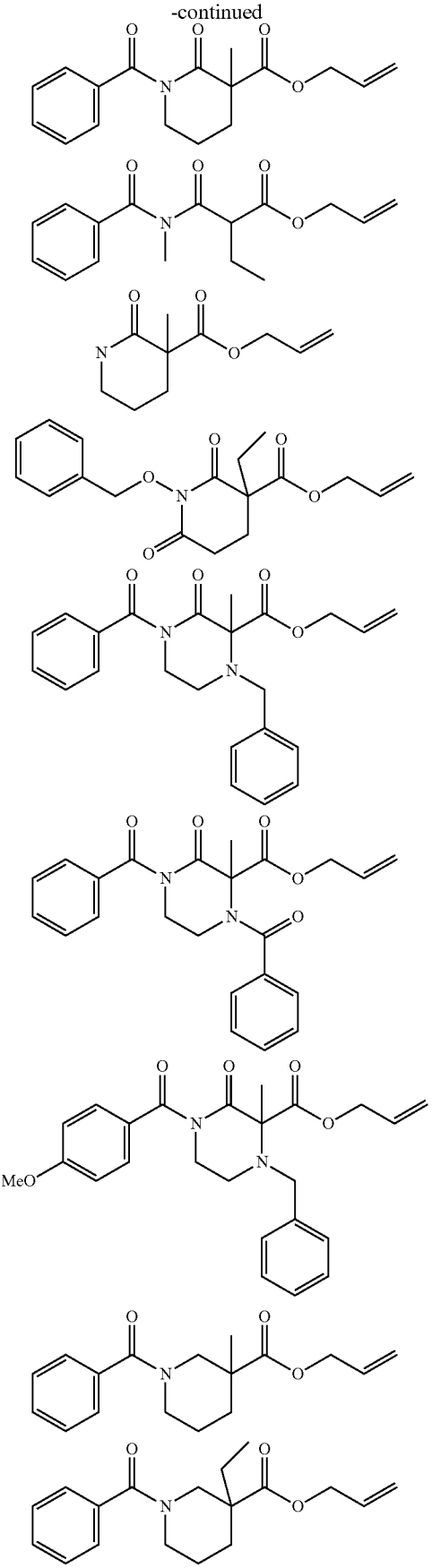

-continued
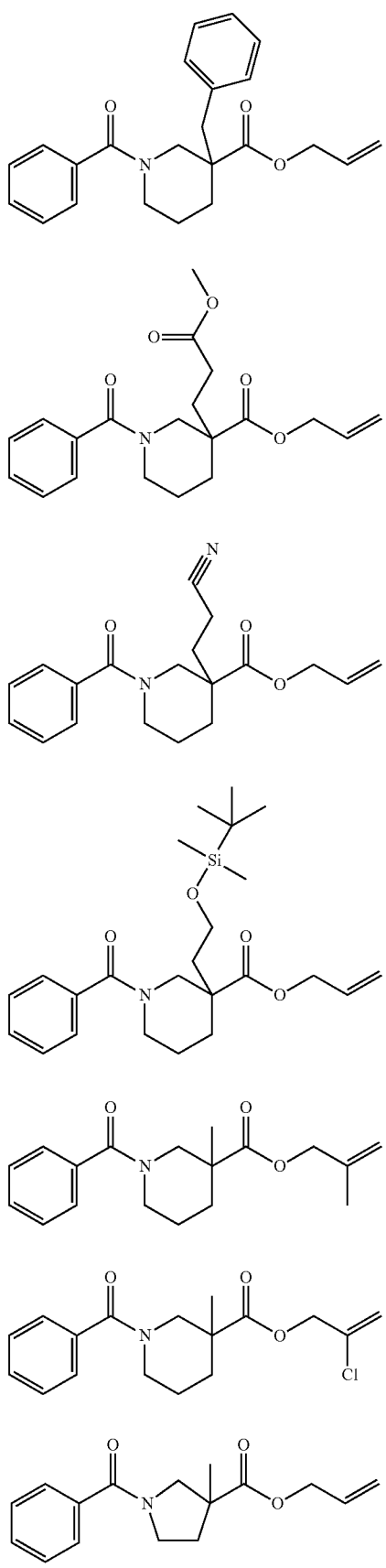
-continued
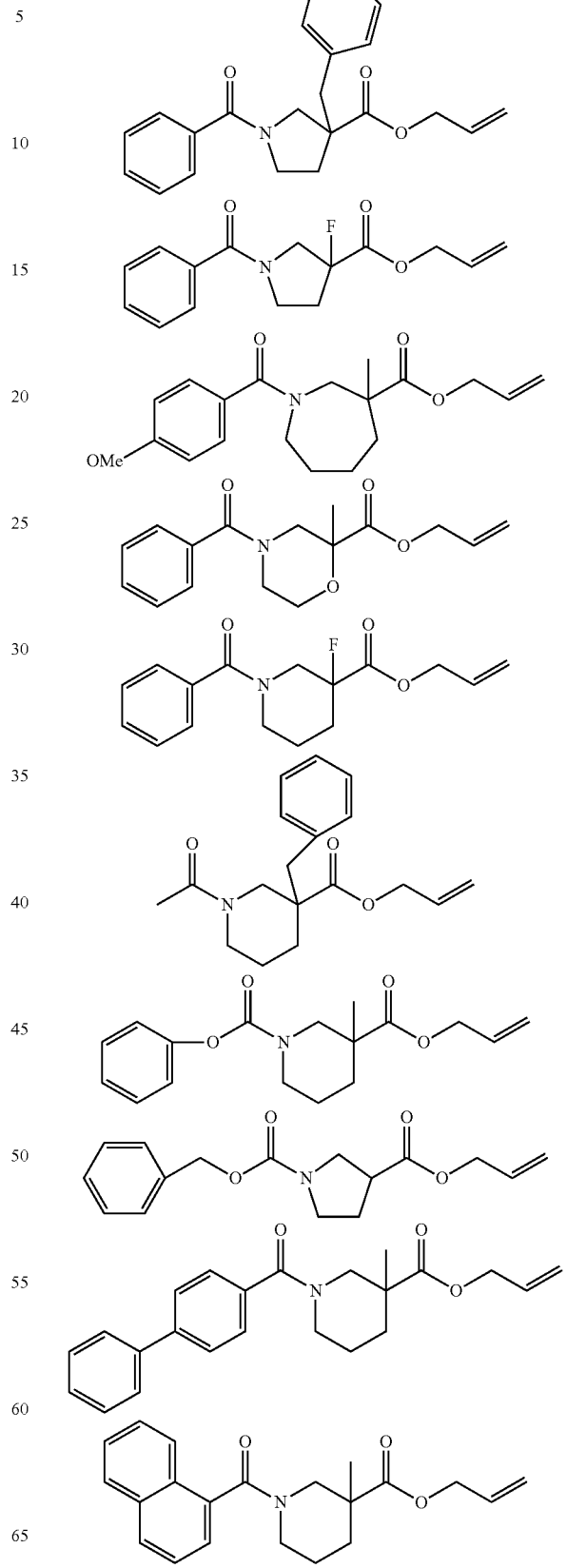

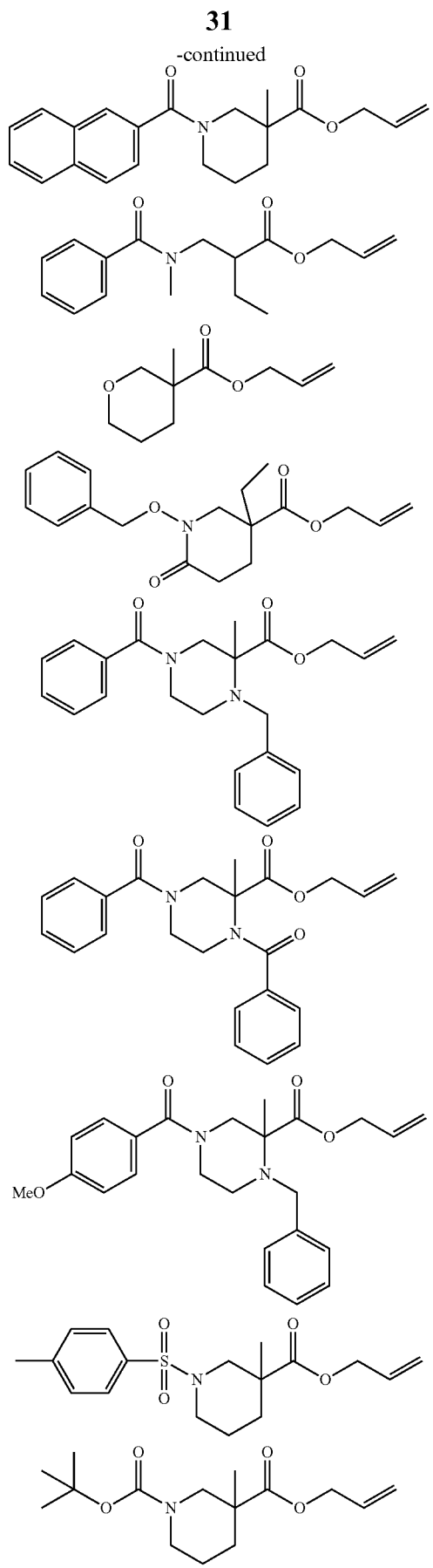

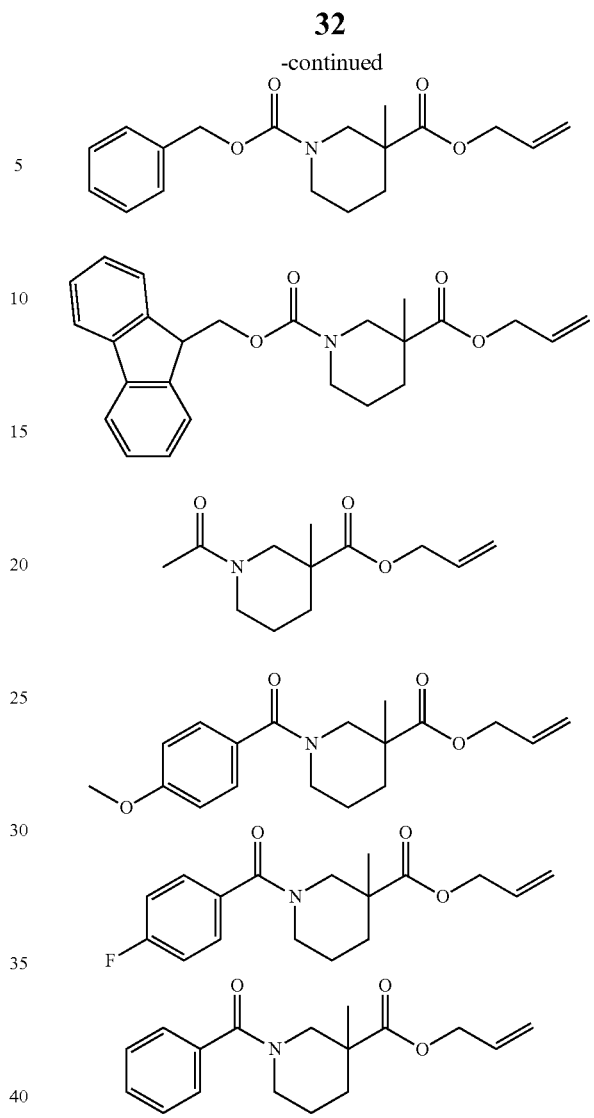

Heteroatom Containing Building Blocks

The heteroatom containing substrates described above may be used to create novel building block compounds useful in the formation of numerous other chemical and pharmaceutical compounds. Indeed, the novel substrates discussed above are designed to create the novel building blocks discussed here via palladium-catalyzed decarboxylative alkylation reactions. These reactions, when performed on racemic compositions of the substrates described above yield enantioenriched compositions of the building block compounds. As the building blocks discussed here are the result of palladium-catalyzed decarboxylative alkylation of the substrates discussed above, the structures of these compounds are similar in many respects to their corresponding substrates. However, as would be recognized by those of ordinary skill in the art based on the differences in the structures, the stereochemistry, enantioselectivity and chemical and physical properties of the building blocks can be significantly different from those of their corresponding substrates.

According to embodiments of the present invention, heteroatom containing building blocks useful in the creation of target compounds include cyclic and acyclic heteroatom containing building blocks represented by Formula 4.

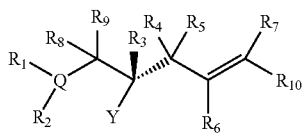

Formula 4

In Formula 4, as in Formula 1 (of the counterpart heteroatom containing substrates), Q is a heteroatom, for example, N, O, P, S or a halogen such as Cl, I, Br or F. In some embodiments, for example, Q is N or O. Each of R1 through R10 is independently selected from hydrogen, substituted or unsubstituted hydrocarbyl groups, substituted or unsubstituted heteroatom containing hydrocarbyl groups, or functional groups. However, in some embodiments, R3 is not hydrogen. In some embodiments, in which z is 0 and R8 and R9 combine to form a carbonyl group, R3 is also not phenyl or substituted phenyl. In yet other embodiments, in which z is 0 and R8 and R9 combine to form a carbonyl group, R3 is not a simple carbonyl group. However, in some embodiments, R3 may be a substituted carbonyl group, e.g., a carbonyl group substituted hydrocarbyl group or heteroatom containing hydrocarbyl group or functional group. In some embodiments, though, R3 does not include any carbonyl groups, whether substituted or unsubstituted. In yet other embodiments, in which z is 0 and R8 and R9 combine to form a carbonyl group, R3 is not an ethyl group. However, in some embodiments, R3 may be a substituted ethyl group, and R3 may be any other alkyl group (or other group as described above). In some embodiments, though, R3 is not an ethyl group or a substituted ethyl group. Also, in some embodiments, the carbon atom to which the R3 group is attached is a chiral, stereogenic center, i.e., R3 and Y are not the same.

Y may be selected from hydrogen, heteroatoms, substituted or unsubstituted hydrocarbyl groups, substituted or unsubstituted heteroatom containing hydrocarbyl groups, or functional groups. Additionally, any two or more adjacent R and Y groups can optionally combine to form a carbonyl group on the underlying atom. For example, in some embodiments, R8 and R9 combine to form a carbonyl group, as shown in the below Formula 4(a).

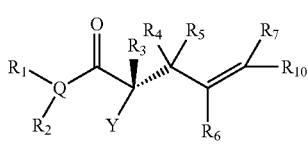

Formula 4(a)

Also, any two or more adjacent R and Y groups can optionally combine to form a ring, e.g., a cyclic, heterocyclic, aryl or heteroaryl ring. Indeed, in some embodiments, although Formula 4 depicts an acyclic heteroatom containing compound, Formula 4 also encompass cyclic, heterocyclic, aryl and heteroaryl compounds. Also, in some embodiments, while R6 and R10 may combine to form nearly any ring structure, R6 and R10 do not form a substituted or unsubstituted benzene ring. In some embodiments, R6 and R10 do not form any aromatic ring. Similarly, in some embodiments, while R4 and R6 may combine to form nearly any ring structure, R4 and R6 do not form a substituted or unsubstituted benzene ring. In some embodiments, R4 and R6 do not form any aromatic ring.

In embodiments in which R2 and Y combine to form a ring, in some embodiments, the atom in the ring directly adjacent the Q atom (i.e., the atom on the opposite side of the Q atom to the carbon atom carrying the R8 and R9 groups) is not a chiral center. More specifically, any substituents on that atom are the same as each other, and that atom does not include two different substituents.

For example, in some embodiments, the R2 group on the Q atom, and the Y group combine to form a ring with the Q atom, the carbon atom to which the Y group is attached, and the intervening carbon atom. The ring formed between the R2 group and the Y group can be any type of ring with any number of ring atoms. However, the ring formed from the combination of R2 and Y does not form a benzene ring or ortho-disubstituted benzene ring. In some embodiments, though, R2 and Y may form other substituted benzene rings. In other embodiments, however, R2 and Y do not form any kind of benzene ring.

In some exemplary embodiments, for example, the ring formed between the $R_2$ group and the Y group may include one or more additional heteroatoms (i.e., additional to the Q atom depicted in Formula 4). In these embodiments, the compounds of Formula 4 may be represented by Formula 5, below.

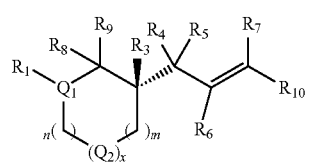

Formula 5

In Formula 5, R1 through R10 are the same as defined above with respect to Formula 4. Each of Q1 and Q2 are as defined above with respect to Q1, and are each independently selected from heteroatoms, e.g., N, O, S, P or halogens, such as Cl, I, F or Br. In some embodiments, for example, each of Q1 and Q2 is independently selected from N or O. Additionally, similar to that described above with respect to Formulae 4 and 4(a), any two or more adjacent R groups can optionally combine to form a carbonyl group on the underlying atom. For example, in some embodiments, R8 and R9 combine to form a carbonyl group, as shown in the below Formula 5(a).

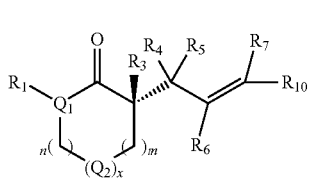

Formula 5(a)

Also, in Formula 5, each of x, n and m can be any integer of 0 or greater. When x is greater than 1, the plurality of Q2 heteroatoms may be the same as or different from each other. In some embodiments, for example, each of x, n and m is independently 0, 1, 2, 3 or 4. In some exemplary embodiments, when x and n are both 0, m may be 1, 2, 3 or 4. Conversely, when x and m are both 0, n may be 1, 2, 3 or 4. These configurations yield compounds having the Formulae 5(b) or 5(c) (where R8 and R9 combine to form a carbonyl group) below. Also, while m and n are defined here such that the ring depicted in Formula 5 has up to 7 ring atoms, it is understood that the size of the ring in Formula 5 is not particularly limited, and n and m can be any integers corresponding to any ring size. For example, in some embodiments, n and m are integers such that the resulting ring depicted in Formula 5 has from 3 to 12 ring atoms. In some embodiments for example, n and m are integers such that the resulting ring has from 3 to 10 ring atoms. In other embodiments, n and m are integers such that the resulting ring has from 5 to 7 ring atoms.

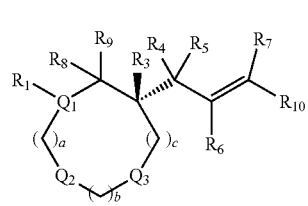

Formula 5(b)

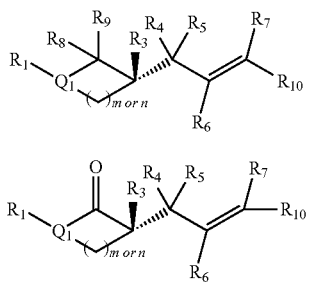

Formula 5(c)

Alternatively, in some embodiments, when x is 1, n and m may be any integer from 0 to 4 such that the sum of n and m may be 0, 1, 2 or 3. For example, in some embodiments, when x is 1, n may be 0 and m may be 0, 1, 2 or 3. In other embodiments, when x is 1, n may be 1 and m may be 0, 1 or 2. In still other embodiments, when x is 1, n may be 2 and m may be 0 or 1. In yet other embodiments, when x is 1, n may be 3 and m may be 0. Conversely, in some embodiments, when x is 1, m may be 0 and n may be 0, 1, 2 or 3. In other embodiments, when x is 1, m may be 1 and n may be 0, 1 or 2. In still other embodiments, when x is 1, m may be 2 and n may be 0 or 1. In yet other embodiments, when x is 1, m may be 3 and n may be 0. These configurations yield compounds of Formula 5 in which there are two heteroatoms, and cover all configurations of the two heteroatoms. Specifically, these configurations cover every possible position of the second heteroatom (Q2) on the ring depicted in Formula 5. Also, while m and n are defined here such that the ring depicted in Formula 5 has up to 7 ring atoms, it is understood that the size of the ring in Formula 5 is not particularly limited, and n and m can be any integers corresponding to any ring size, as discussed above. For example, in some embodiments, n and m are integers such that the resulting ring depicted in Formula 5 has from 3 to 12 ring atoms, for example 3 to 10 ring atoms or 5 to 7 ring atoms.

In some embodiments, the ring may include the Q atom depicted in Formulae 4 and 5 as the only heteroatom, and include any number of additional carbon atoms in the ring. Alternatively, however, the ring depicted in Formulae 5 and 5(a) through 5(c) can have any number of heteroatoms positioned anywhere on the ring. For example, as shown in Formula 5 and 5(a) above, the ring may include the heteroatom depicted in Formulae 4 and 5 separated from a group of one or more additional heteroatoms by one or more carbon atoms, or the ring may include two or more heteroatoms that are adjacent each other within the ring. However, according to other embodiments, the ring depicted in Formula 5 may include three or more heteroatoms which may be adjacent one another or separated from each other by at least one carbon atom. This configuration is depicted in Formulae 5(d) and 5(e) (where R8 and R9 combine to form a carbonyl group) below.

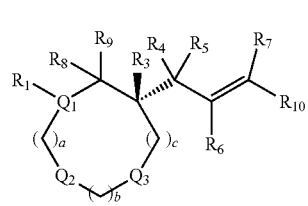

Formula 5(d)

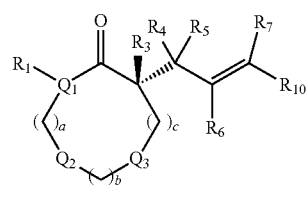

Formula 5(e)

In Formula 5(d) and 5(e), each of Q1, Q2 and Q3 is as defined above with respect to Q1, and each is independently a heteroatom, for example, O, N, S, P, or a halogen such as Cl, I, Br or F. Each of R1 through R10 is also as described above with respect to Formulae 4, 5 and 5(a) through 5(c). Each of a, b and c is independently an integer of 0 or greater. In some exemplary embodiments, each of a, b and c may be independently an integer of 0, 1 or 2. For example, in some embodiments, each of a, b and c is 0, yielding a five membered ring including three adjacent heteroatoms. In other embodiments, a is 1 and b and c are both 0, yielding a six membered ring in which Q2 and Q3 are adjacent one another and Q2 is separated from Q1 by a carbon atom. In still other embodiments, a is 2 and b and c are both 0, yielding a seven membered ring in which Q2 and Q3 are adjacent one another and Q2 is separated from Q1 by two carbon atoms.

According to other embodiments, b is 1 and a and c are both 0, yielding a six membered ring in which Q1 and Q2 are adjacent one another and Q2 is separated from Q3 by a carbon atom. In still other embodiments, b is 2 and a and c are both 0, yielding a seven membered ring in which Q1 and Q2 are adjacent one another and Q2 is separated from Q3 by two carbon atoms.

In other embodiments, c is 1 and a and b are both 0, yielding a six membered ring in which Q1, Q2 and Q3 are adjacent one another. In still other embodiments, c is 2 and a and b are both 0, yielding a seven membered ring in which Q1, Q2 and Q3 are adjacent one another. Also, while a, b and c are defined here such that the ring depicted in Formulae 5, 5(d) and 5(e) has up to 7 ring atoms, it is understood that the size of the ring in Formulae 5, 5(d) and 5(e) is not particularly limited, and a, b and c can be any integers corresponding to any ring size, as discussed above. For example, in some embodiments, a, b and c are integers such that the resulting ring depicted in Formulae 5, 5(d) and 5(e) has from 3 to 12 ring atoms, for example 3 to 10 ring atoms or 5 to 7 ring atoms.

In some exemplary embodiments, the ring depicted in Formula 5 may include four heteroatoms, and the four heteroatoms may be placed on the ring in any manner. For example, some of the heteroatoms may be spaced from each other by one or more ring carbon atoms while others are adjacent, or all heteroatoms may be adjacent each other, or all heteroatoms may be spaced from each other by one or more ring carbon atoms.

Additionally, although the rings discussed above may be depicted and described as fully saturated, according to some embodiments of the present invention, any of the rings may be unsaturated (i.e., mono- or poly-unsaturated). To account for these compounds, the heteroatom containing substrate of Formula 4 may be represented by Formulae 6 or 6(a) (where R8 and R9 combine to form a carbonyl group) below.

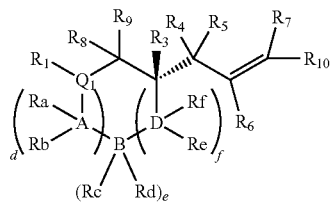

Formula 6

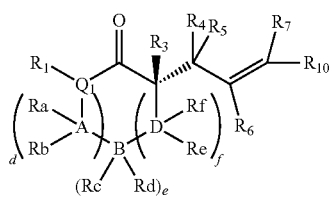

Formula 6(a)

In Formulae 6 and 6(a), Q1 and R1 through R10 are as defined above with respect to Formulae 4, 5 and 5(a) through 5(e). Each of A, B and D is independently a carbon atom or a heteroatom. However, in some embodiments, in which d is 1 or greater, the A atom located directly adjacent the Q1 atom is not a chiral center. More specifically, the Ra and Rb substituents on that atom are the same as each other, and are not two different substituents. Also, the ring formed from Q1, A, B and D is not a benzene ring or an ortho-disubstituted benzene ring. In some embodiments, though, the ring may be any other substituted benzene ring. In other embodiments, however, the ring is not any kind of benzene ring.

Each of Ra, Rb, Rc, Rd, Re and Rf may be independently selected from hydrogen atoms, substituted or unsubstituted hydrocarbyl groups, substituted or unsubstituted heteroatom containing hydrocarbyl groups, halogens or functional groups. However, as discussed above, in some embodiments, in which d is greater than 1, the A atom located directly adjacent the Q1 atom is not a chiral center, and the Ra and Rb substituents on that atom are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond. For example, R1 and one of the Ra groups may combine to form a double bond, one of the Rb groups and one of the Rc groups may combine to form a double bond within the ring, or one of the Rd groups and one of the Re groups may combine to form a double bond within the ring. Any number of double bonds may be formed within the ring structure, and the ring structure may be heteroaryl in nature. Alternatively or additionally, two adjacent R groups on the same ring atom (e.g., Ra and Rb, or Rc and Rd, or Re and Rf) can combine to form a carbonyl group on the ring atom. Each of d, e and f is independently an integer of 0 or greater, for example, an integer of 0, 1, 2, 3, or 4. When d, e or f is greater than 1, the plurality of A, B or D atoms, and the plurality of Ra, Rb, Rc, Rd, Re or Rf groups may be the same as or different from each other. Also, although Formulae 6 and 6(a) above depict a six membered ring, it is understood from the definitions of d, e and f that the ring is not limited to six members, and can have any number of ring atoms, as discussed above with respect to Formulae 4, 4 and 4(a) through 4(e). Indeed, in some embodiments, the ring has from 3 to 12 ring atoms, for example 3 to 10 ring atoms or 5 to 7 ring atoms.

Also, in the rings discussed above, any of the ring atoms, whether carbon or heteroatom, can be substituted with a substituted or unsubstituted hydrocarbyl group, substituted or unsubstituted heteroatom containing hydrocarbyl group, a halogen or a functional group. Indeed, although the rings depicted in Formulae 5 and 5(a) through 5(e) above are depicted with hydrogen atoms on each of the ring atoms, any or all of the hydrogen atoms on any or all of the ring atoms may be substituted with the substituents described above. As shown in Formula 6, for example, each of the ring atoms (Q1, A, B and/or D) may include R groups that can be hydrogen, a substituted or unsubstituted hydrocarbyl group, a substituted or unsubstituted heteroatom containing hydrocarbyl group, a halogen or a functional group.

In some embodiments of the present invention, the building block compounds can have an alternate structure represented by the below Formulae D. The compounds of Formula D include compounds created by the palladium catalyzed decarboxylative alkylation of substrate compounds represented by Formula 1(a), 2(a) or 3(a) in which Q (or Q1) is O.

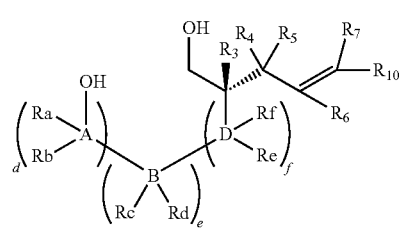

Formula D

As noted above, compounds of Formula D can be made through the palladium catalyzed decarboxylative alkylation of a lactone satisfying one of Formulae 1(a), 2(a) or 3(a) above. Specifically, the compound of Formula D will result when a compound of Formula 3(a) (in which Q1 is O) is subjected to palladium catalyzed decarboxylative alkylation. In Formula D, A, B, D, Ra, Rb, Rc, Rd, Re, Rf, R3, R4, R5, R6, R7 and R10 are as described above with respect to Formulae 1 through 3. For example, each of Ra, Rb, R, Rd, Re and Rf may be independently selected from hydrogen atoms, substituted or unsubstituted hydrocarbyl groups, substituted or unsubstituted heteroatom containing hydrocarbyl groups, halogens or functional groups. However, similar to that discussed above with respect to Formulae A through C and 4 through 6, in some embodiments, in which d is 1 or greater, the A atom that is directly adjacent the OH group is not a chiral center. More specifically, the Ra and Rb groups on the A atom that is directly adjacent the OH group are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond.

In Formulae 4, 4(a), 5, 5(a) through 5(b), 6 and 6(a) above, the heteroatom containing building blocks are depicted and described as including a terminal alkenyl group. This position of the alkenyl group may be imparted by the palladium catalyzed decarboxylative alkylation reaction used to create the building blocks. However, after creation via the palladium catalyzed decarboxylative alkylation reaction, the building blocks can be further modified to move the alkenyl group to a position other than the terminal end of the compound. For example, the alkenyl group can be positioned as shown in the below Formulae 4(b) and 4(c) (where R8 and R9 combine to form a carbonyl group).

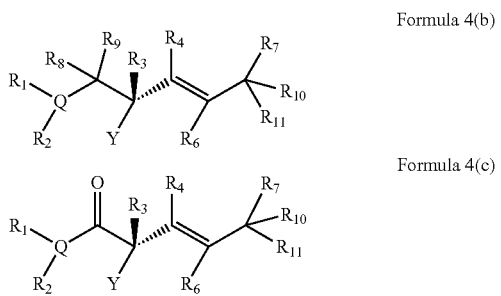

Formula 4(b)

Formula 4(c)

In Formula 4(a), Q, Y and R1 through R10 are as described above with respect to Formulae 4, 5, 5(a) through 5(e), 6 and 6(a). Also, R11 is selected from the same substituents described above for R1 through R9. Specifically, each of R1 through R11 may be independently selected from hydrogen, substituted or unsubstituted hydrocarbyl groups, substituted or unsubstituted heteroatom containing hydrocarbyl groups, halogens or functional groups.

In other embodiments, in which the compound is analogous to the compound represented by Formula D, the alkenyl group can be positioned as shown in the below Formula D(i)

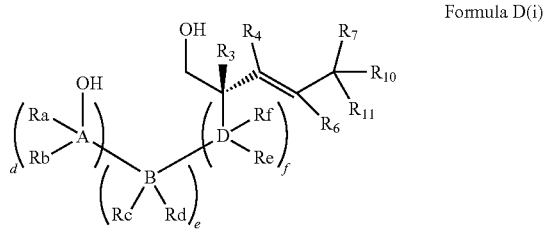

Formula D(i)

In Formula D(i), A, B, D, Ra through Rf, d, e, f, and R3 through R10 are as described above. Also, R11 is selected from the same substituents described above for R1 through R10. Specifically, each of R1 through R11 may be independently selected from hydrogen, substituted or unsubstituted hydrocarbyl groups, substituted or unsubstituted heteroatom containing hydrocarbyl groups, halogens or functional groups. However, similar to that discussed above with respect to Formulae A through C and 4 through 6, in some embodiments, in which d is 1 or greater, the A atom that is directly adjacent the OH group is not a chiral center. More specifically, the Ra and Rb groups on the A atom that is directly adjacent the OH group are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond.

Additionally, in Formulae 4, 4(a), 5, 5(a) through 5(b), 6 and 6(a) above, the heteroatom containing building blocks are depicted and described as potentially including non-hydrogen R groups (R7 and or R10) on the terminal alkenyl group. In embodiments in which the building blocks include such a non-hydrogen R group on the terminal alkenyl group, the R group is added via a reaction occurring after the palladium catalyzed decarboxylative alkylation reaction used to create the building block. Specifically, while the palladium catalyzed decarboxylative alkylation reaction may result in building blocks including only hydrogen on the terminal alkenyl, if desired, the building block furnished by the palladium catalyzed decarboxylative alkylation reaction can be further modified to substitute one or both of the hydrogen atoms on the terminal alkenyl group with a substituted or unsubstituted hydrocarbyl, a substituted or unsubstituted heteroatom containing hydrocarbyl, a halogen or a functional group.

In Formulae 4 through 6 above, the terminal alkenyl group can be reacted (e.g., hydrogenated) to make a corresponding alkyl derivative having the below Formula 4(d) and 4(e) (in which the R8 and R9 groups combine to form a carbonyl group) in which z is 0.

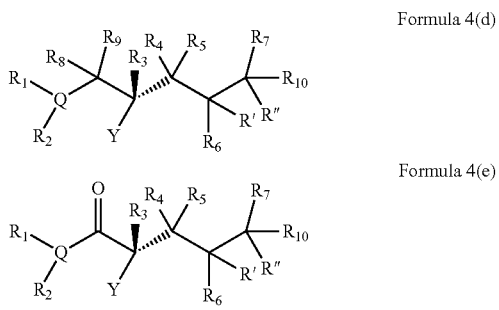

Formula 4(d)

Formula 4(e)

In Formula 4(d) and 4(e), Q, Y and R1 through R11 are as described above with respect to Formulae A through C. Also, R' and R" are independently selected from the same substituents described above for R1 through R11. Specifically, each of R1 through R11 and R' and R" may be independently selected from hydrogen, substituted or unsubstituted hydrocarbyl groups, substituted or unsubstituted heteroatom containing hydrocarbyl groups, halogens or functional groups. Also, it is understood that although Formula 4 through 6 are discussed and depicted above as including the terminal alkenyl group, any of those formulae may instead include the terminal alkyl discussed here and depicted in Formulae 4(d) and 4(e).

In some embodiments of the present invention in which the heteroatom is a nitrogen atom, the R group on the heteroatom (i.e., Q, Q1, Q2, Q3, or other heteroatoms in the building blocks of Formulae 4 through 6) can be an amine protecting group. Those of ordinary skill in the art would readily understand what is meant by "amine protecting group." However, some nonlimiting examples of suitable amine protecting groups include carbobenzyloxy (Cbz) groups, p-methoxybenzyl carbonyl (Moz or MeOZ) groups, tert-butyloxycarbonyl (BOC) groups, fluorenylmethyloxycarbonyl (FMOC) groups, acetyl (Ac) groups, benzoyl (Bz) groups, benzyl (Bn) groups, carbamate groups, p-methoxybenzyl (PMB) groups, dimethoxybenzyl (DMPM) groups, p-methoxyphenyl (PMP) groups, tosyl (Ts) groups, sulfonamide (Nosyl & Nps) groups, methoxybenzoyl groups (OMe-Bz), and fluorobenzoyl groups (F-Bz). For example, in some embodiments, the amine protecting group is selected from tosyl groups (Ts), butyloxycarbonyl groups (BOC), carbobenzyloxy groups (Cbz), fluoreneylmethyloxycarbonyl groups (FMOC), acetyl groups (Ac), methoxybenzoyl groups (OMe-Bz), fluorobenzoyl groups (F-Bz), and benzoyl groups (Bz).

In some alternate embodiments, however, the R group(s) on the N can be hydrogen, a substituted or unsubstituted hydrocarbyl group, a substituted or unsubstituted heteroatom containing hydrocarbyl group, or a functional group. For example, in some embodiments, the R group(s) on the N atom may be H or OH.

Also, the building blocks described above are generally formed from the racemic form of the corresponding substrate compound. The resulting building block compounds may also be racemic, however, in some embodiments, the palladium catalyzed decarboxylative alkylation procedures result in enantioenriched building block compounds. As used herein, the term "enantionriched" refers to an enantiomeric excess of the particular enantiomer of the compound. Specifically, the building block compounds according to embodiments of the present invention include on eof (+) or (−) enantiomers in an enantiomeric excess, thus creating an "enantioenriched" building block compound. In some embodiments, for example, the enantioenriched building block compound may include one of the (+) or (−) enantiomers in an enantiomeric excess of greater than 50%, for example, about 60% or greater, or about 70% or greater, or about 80% or greater According to some embodiments, the enantioenriched building block compound may include one of the (+) or (−) enantiomers in an enantiomeric excess of about 90% or greater. In other embodiments, the enantioenriched building block compound may include one of the (+) or (−) enantiomers in an enantiomeric excess of about 90% to about 99%.

Some nonlimiting examples of building blocks satisfying the above formula, according to embodiments of the present invention, include the compounds depicted below. It is understood that although some of the nitrogen atoms in some of the nitrogen containing-compounds listed below include protecting groups, the nitrogen atoms do not necessarily include protecting groups. Indeed, in some embodiments of the present invention, hydrogen atoms are attached to the nitrogen atoms. In each of the examples listed below, the protecting group on any of the nitrogen atoms can be replaced with a hydrogen atom.

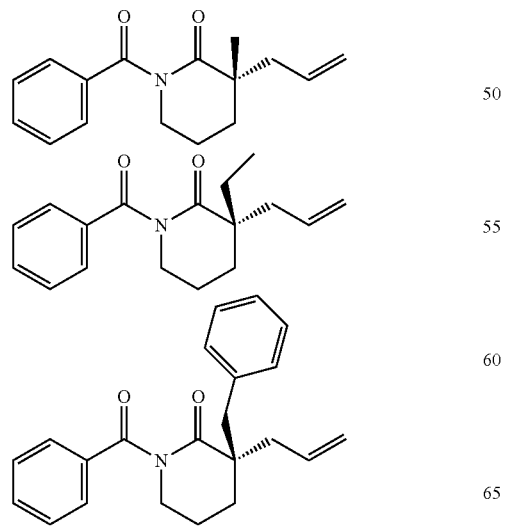

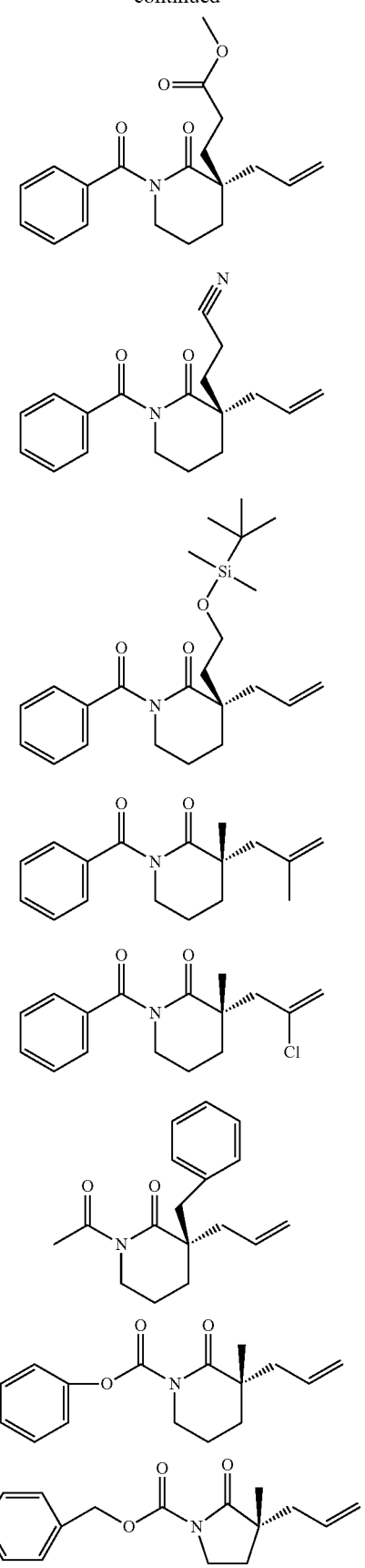

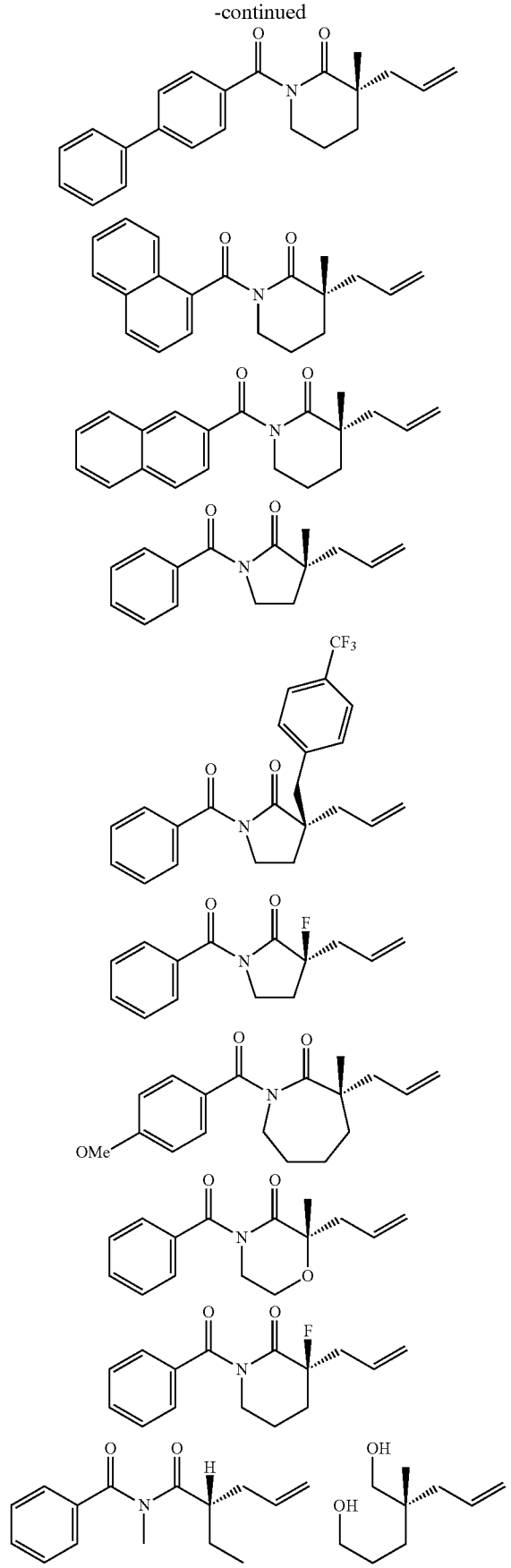
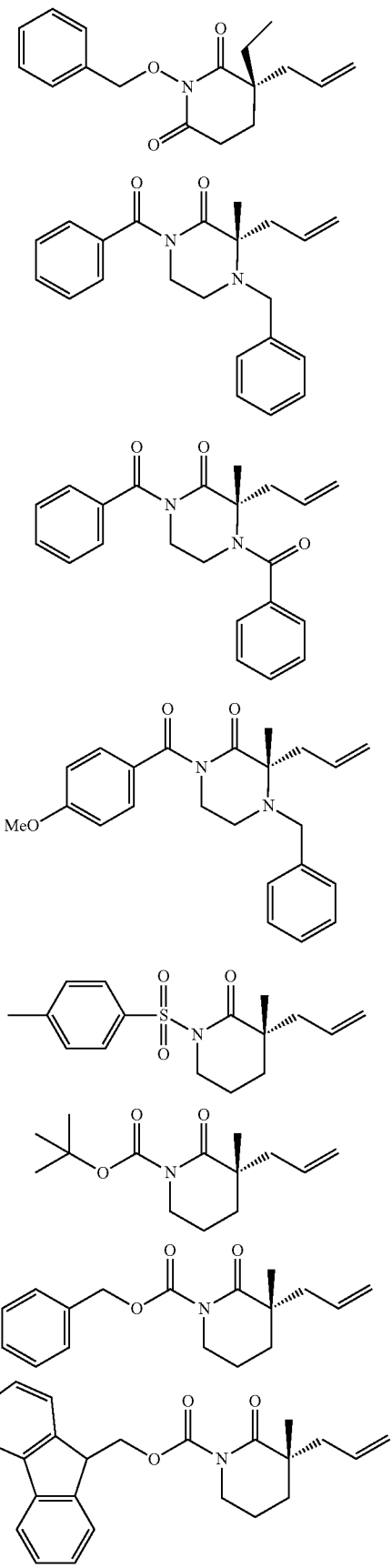

45
-continued
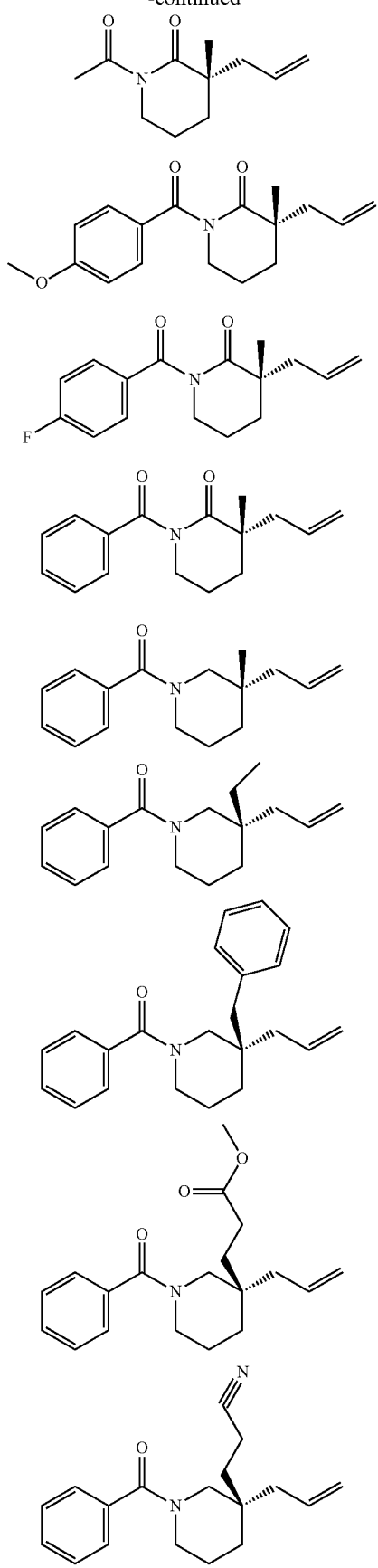
46
-continued
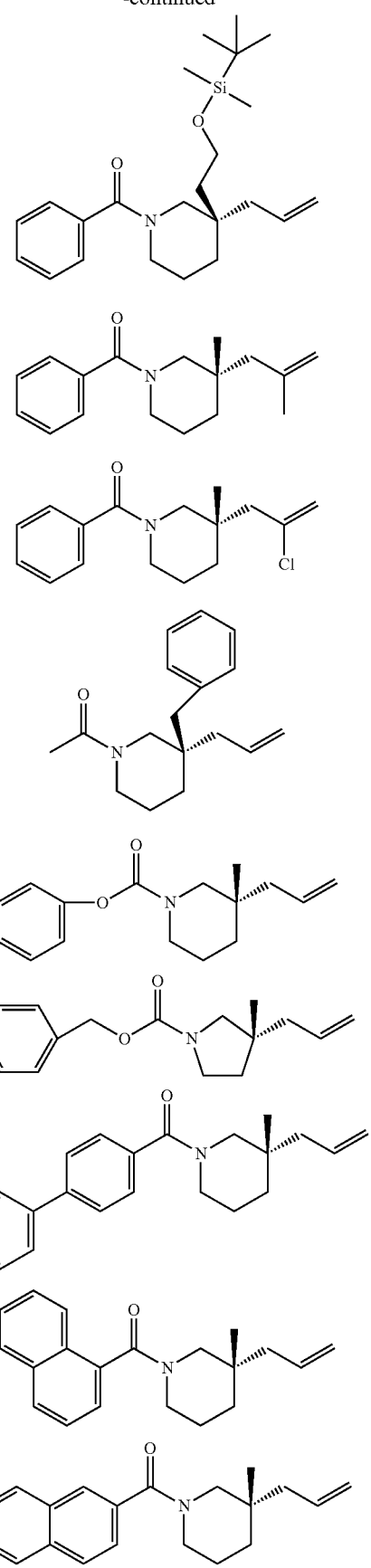

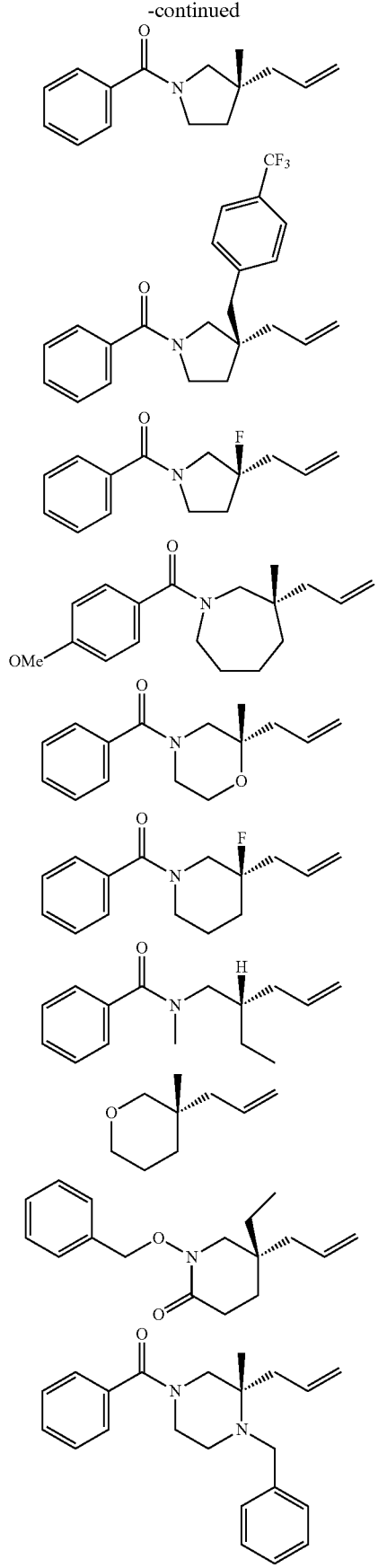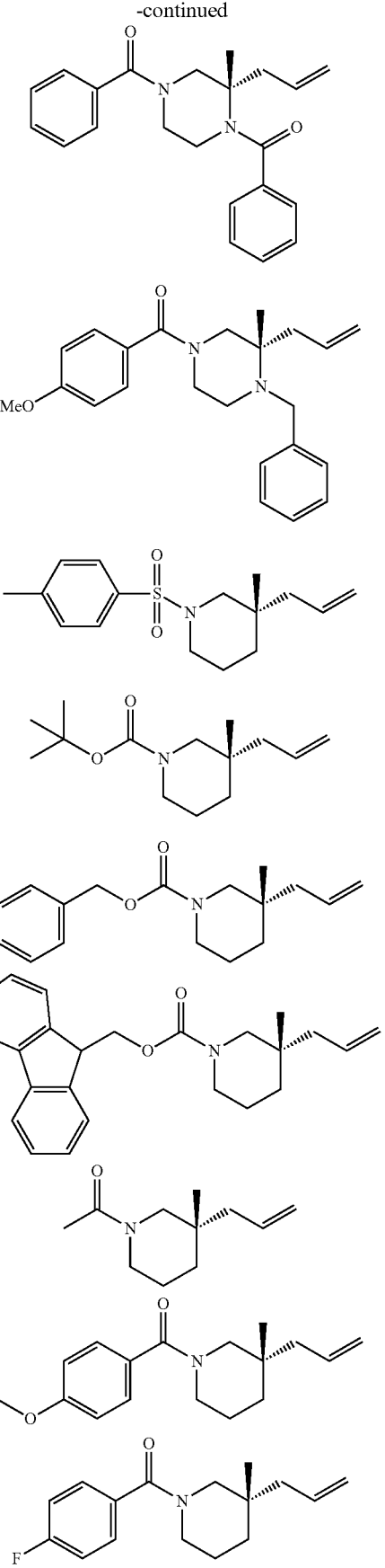

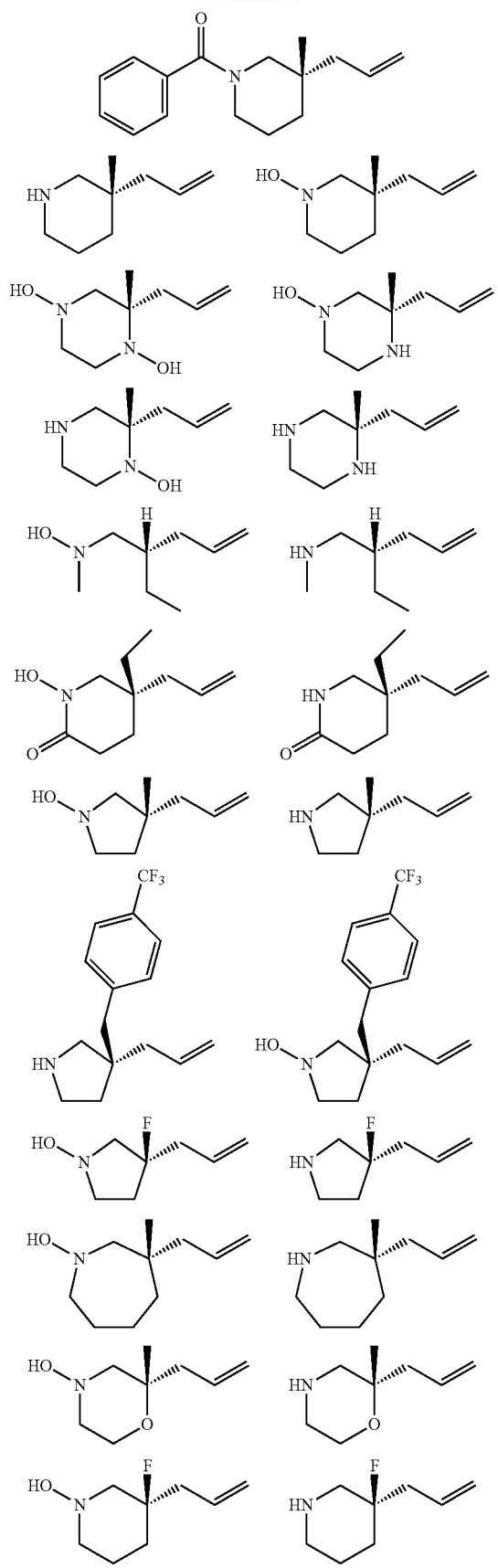
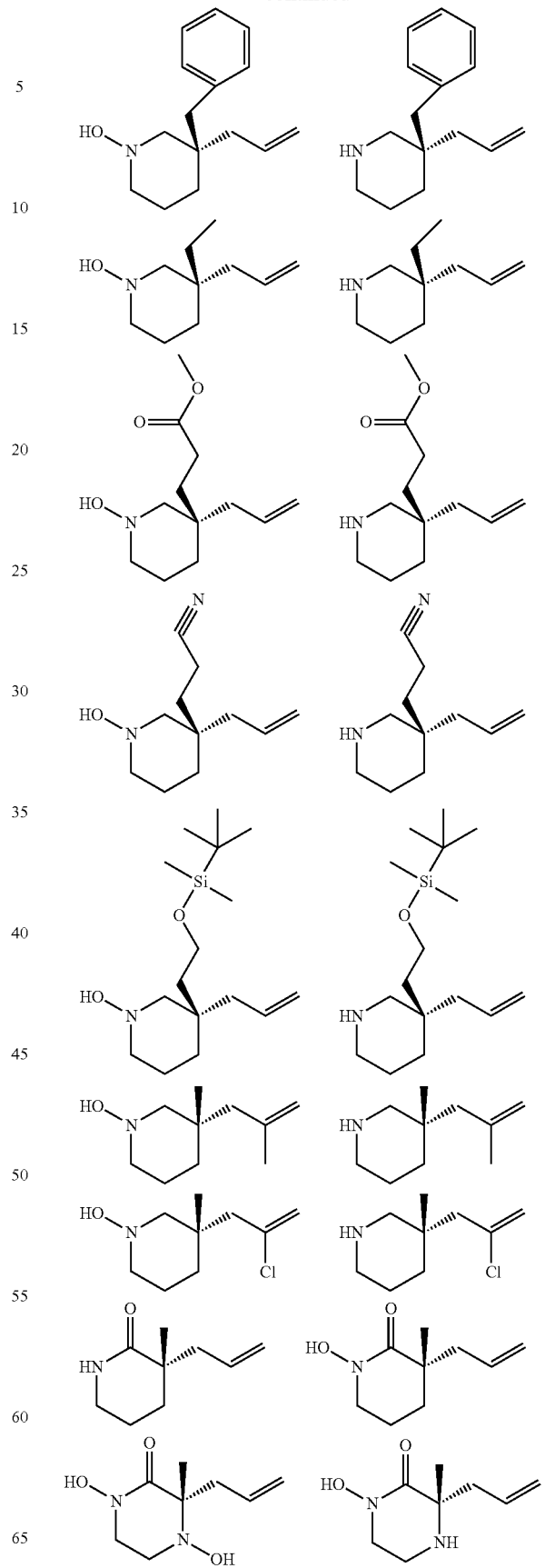

-continued

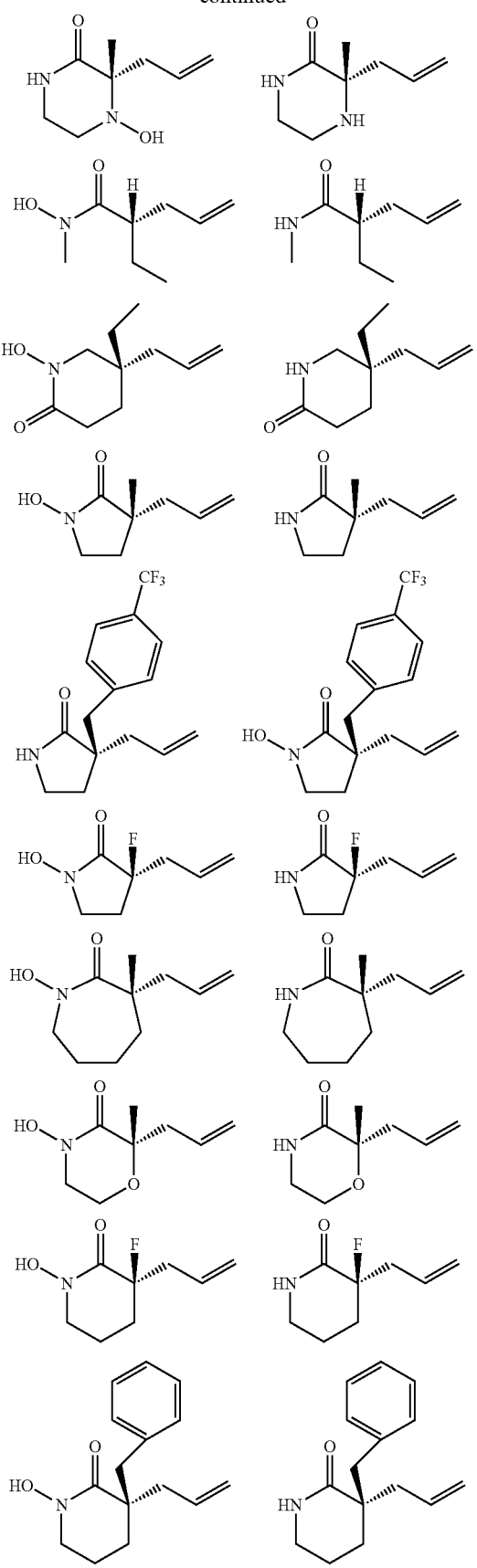
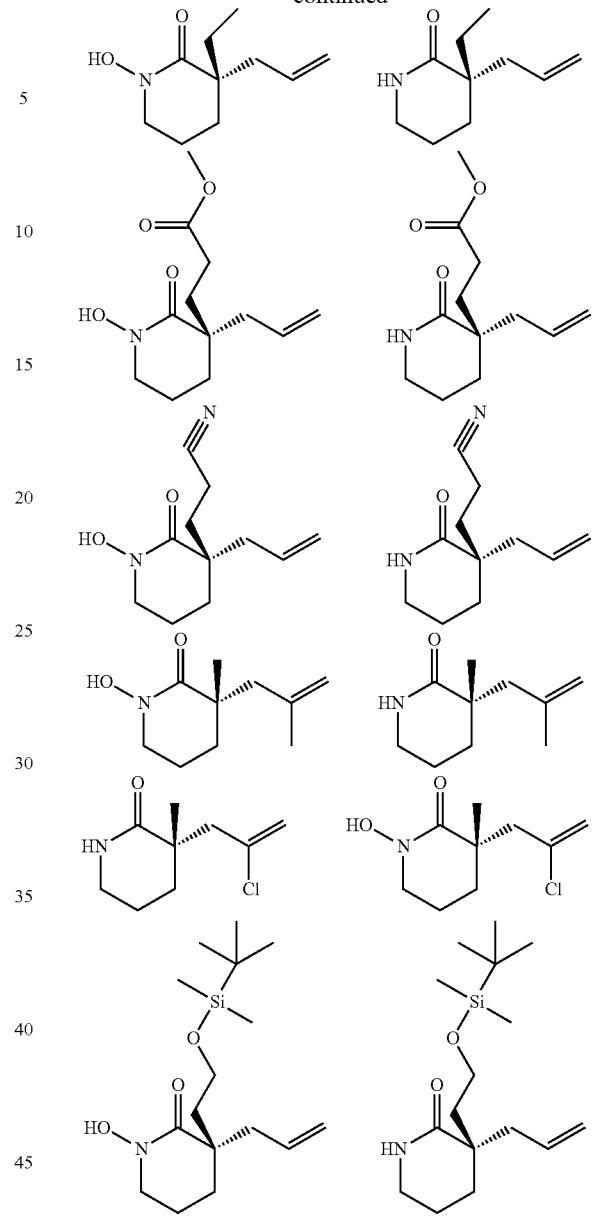

Palladium Catalyzed Decarboxylative Alkylation Reaction

As discussed above, decarboxylative alkylation chemistry, and related allylic alkylation methods have been used in the creation of certain classes of compounds, e.g., α-quaternary ketones. However, to date, there are no known transition metal catalyzed decarboxylative alkylation methods for making enantioselective lactam and related compounds.

For a description of the decarboxylative alkylation chemistry, and the attendant methods for making certain compounds, see Mohr, et al., "Deracemization of quaternary stereocenters by Pd-catalyzed enantioconvergent decarboxylative allylation of racemic β-ketoesters," *Angew. Chem., Int. Ed.* 44, 6924-6927 (2005); Seto, et al., "Catalytic enantioselective alkylation of substituted dioxanone enol ethers: ready access to C(α)-tetrasubstituted hydroxyketones, acids, and esters," *Angew. Chem. Int. Ed.* 47, 6873-6876 (2008); Streuff, et al., "A Palladium-catalysed enolate alkylation cascade for the formation of adjacent quaternary and tertiary stereocentres," *Nature Chem.* 2, 192-196 (2010);

McFadden, et al., The catalytic enantioselective, protecting group-free total synthesis of (+)-dichroanone," *J. Am. Chem. Soc.* 128, 7738-7739 (2006); White, et al., The catalytic asymmetric total synthesis of elatol," *J. Am. Chem. Soc.* 130, 810-811 (2008); Enquist, et al., The total synthesis of (−)-cyanthiwigin F via double catalytic enantioselective alkylation," *Nature* 453, 1228-1231 (2008); Day, et al., The catalytic enantioselective total synthesis of (+)-liphagal," *Angew. Chem. Int. Ed.* 50, in press (2011), the entire contents of all of which have already been incorporated herein by reference.

For a description of some related allylic alkylation methods, see Trost, et al., "Regio- and Enantioselective Pd-Catalyzed Allylic Alkylation of Ketones through Allyl Enol Carbonates," *J. Am. Chem. Soc.* 127, 2846-2847 (2005); Trost, et al., "Palladium-Catalyzed Asymmetric Allylic α-Alkylation of Acyclic Ketones," *J. Am. Chem. Soc.* 127, 17180-17181 (2005); Trost, et al., "Asymmetric Allylic Alkylation of Cyclic Vinylogous Esters and Thioesters by Pd-Catalyzed Decarboxylation of Enol Carbonate and β-Ketoester Substrates," *Angew. Chem., Int. Ed.* 45, 3109-3112 (2006); Trost, et al., "Enantioselective Synthesis of α-Tertiary Hydroxyaldehydes by Palladium-Catalyzed Asymmetric Allylic Alkylation of Enolates." *J. Am. Chem. Soc.* 129, 282-283 (2007); Trost, et al., "Palladium-Catalyzed Decarboxylative Asymmetric Allylic Alkylation of Enol Carbonates," *J. Am. Chem. Soc.* 131, 18343-18357 (2009); Nakamura, et al., "Synthesis of Chiral α-Fluoroketones through Catalytic Enantioselective Decarboxylation," *Angew. Chem., Int. Ed.* 44, 7248-7251 (2005); Burger, et al., "Catalytic Asymmetric Synthesis of Cyclic α-Allylated α-Fluoroketones," *Synlett* 2824-2826 (2006); Bélanger, et al., "Enantioselective Pd-Catalyzed Allylation Reaction of Fluorinated Silyl Enol Ethers," *J. Am. Chem. Soc.* 129, 1034-1035 (2007); Schulz, et al., "Palladium-Catalyzed Synthesis of Substituted Cycloheptane-1,4-diones by an Asymmetric Ring-Expanding Allylation (AREA)," *Angew. Chem., Int. Ed.* 46, 3966-3970 (2007), the entire contents of all of which have already been incorporated herein by reference.

The building blocks according to embodiments of the present invention, discussed in detail above, can be prepared by the transition metal catalyzed decarboxylative alkylation processes discussed in the references cited above. However, further investigation into the known ketone allylic alkylation reactions (and other related reactions), as discussed here, led to increased enantio- and stereo-selectivity of the reaction to yield highly enantioenriched building block compounds.

In the course of investigating the ketone enolate allylic alkylation and other alkylation processes, interesting ligand electronic effects and, in certain cases, pronounced solvent effects were encountered. McDougal, et al., "High-throughput screening of the asymmetric decarboxylative alkylation reaction of enolate-stabilized enol carbonates," *Synlett* 1712-1716 (2010), the entire content of which is incorporated herein by reference. For example, it was found that for inductively- and resonance-stabilized enolates, highly electron deficient ligands and non-polar solvents are desired. With these findings as a backdrop, further probing of these subtle effects involved examination of enolate reactivity in a lactam series that would be amenable to both steric and electronic fine-tuning. This further probing led to ligand and solvent designs useful for the alkylation of N-heterocycles (and other nitrogen containing compounds) and the construction of the novel building block compounds (discussed above) that are useful for medicinal and polymer chemistry.

Preliminary data suggested that electron rich N-alkyl lactam derivatives were poor substrates for decarboxylative alkylation due to low reactivity. Thus, electron withdrawing N-protecting groups were chosen. These substrates were screened across a series of four solvents (THF, MTBE, toluene, and 2:1 hexane-toluene) while employing two electronically distinct ligands on Pd. Specifically, the reactions used in the screening were carried out using racemic lactams 1a through 1 h (depicted below) as the reactants, a Pd2(dba)$_3$ catalyst (5 mol %), a solvent and a ligand. For each of the lactam compounds 1a through 1 h, eight experiments were carried out. Specifically, four experiments were carried out using the same first ligand, i.e., (S)-t-BuPHOX (12.5 mol %), but varying the solvent (0.033 M) between THF, MTBE, toluene, and 2:1 hexane-toluene. The other four experiments for each lactam compound were carried out using the same second ligand, i.e., (S)—(CF3)-3-t-BuPHOX (12.5 mol %), but varying the solvent (0.033 M) between THF, MTBE, toluene, and 2:1 hexane-toluene. Each experiment was carried out at 40° C.

Compound 1a
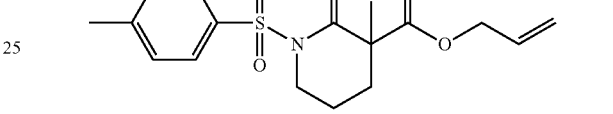

Compound 1b
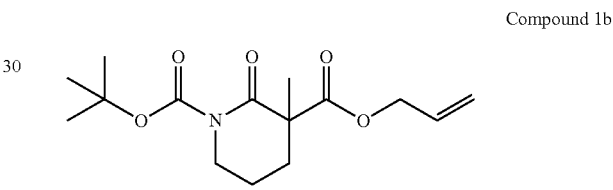

Compound 1c
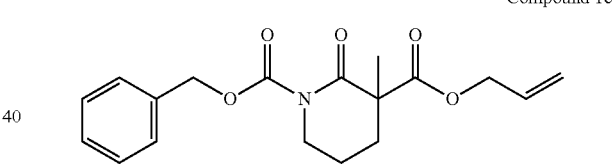

Compound 1d
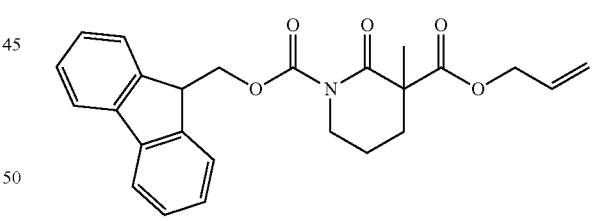

Compound 1e
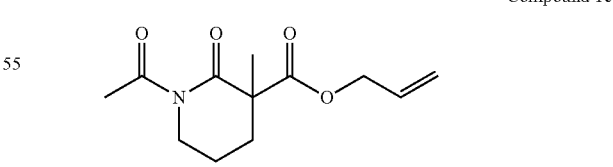

Compound 1f
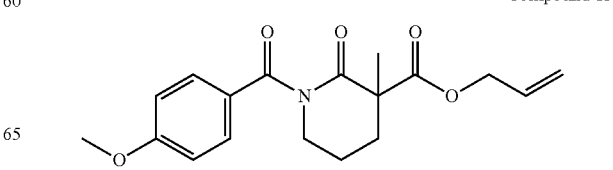

Compound 1g
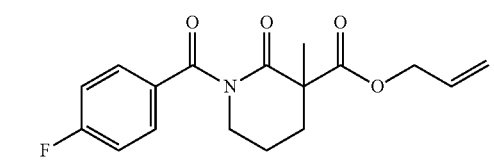

Compound 1h
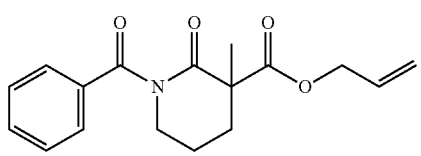

The compounds resulting from the palladium catalyzed decarboxylative alkylation reactions of Compounds 1a through 1h, described above, are depicted below as Compounds 2a through 2h, where Compound 2a corresponds to the compound made from the reaction of Compound 1a, Compound 2b corresponds to the compound made from the reaction of Compound 1b, Compound 2c corresponds to the compound made from the reaction of Compound 1c, Compound 2d corresponds to the compound made from the reaction of Compound 1d, Compound 2e corresponds to the compound made from the reaction of Compound 1e, Compound 2f corresponds to the compound made from the reaction of Compound 1f, Compound 2g corresponds to the compound made from the reaction of Compound 1g, and Compound 2h corresponds to the compound made from the reaction of Compound 1h.

Compound 2a
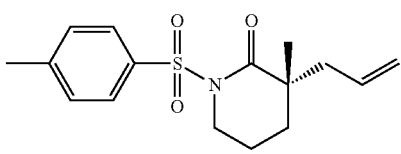

Compound 2b
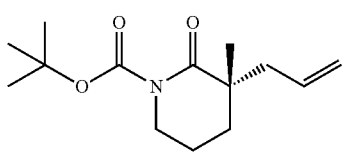

Compound 2c
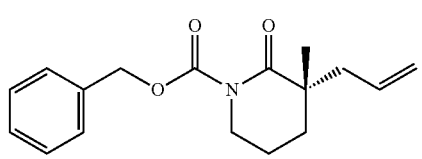

Compound 2d
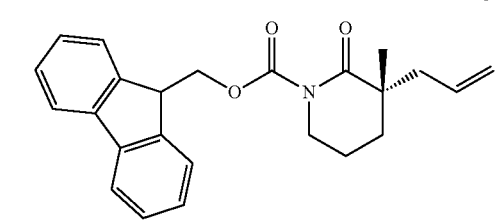

Compound 2e
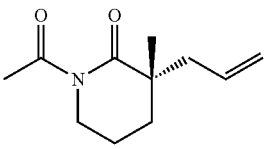

Compound 2f
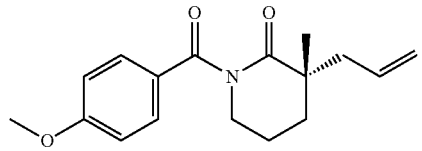

Compound 2g
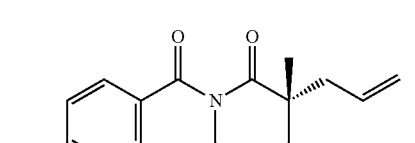

Compound 2h
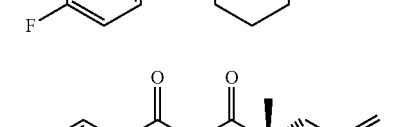

The results of this broad screen were highly encouraging, as shown in FIG. 1 (depicting the enantiomeric excess of the compounds prepared using the lactam reactants (Compounds 1a through 1h) with the various ligands and solvents discussed above). Reactivity across all substrates with either ligand was uniformly good, as all of the compounds were completely converted to the desired product. Strikingly, as the N-substituent group was changed from sulfonyl to carbamoyl to acyl functionalities, the enantioselectivity rose from nearly zero to nearly perfect. There was also a difference between the two ligands, and electron poor (S)—(CF$_3$)$_3$-t-BuPHOX was the better choice. As the solvent system became less polar, a distinct increase in enantiomeric excess was observed, however, this effect was substantially less pronounced for reactions employing the electron poor ligand and for reactions varying the N-substituent. Ultimately, with the N-benzoyl group (Bz) on the substrate (i.e., Compound 1h) and (S)—(CF$_3$)$_3$-t-BuPHOX as ligand, the reaction produced the lactam of Compound 2h in >96% ee in each of the four solvents.

Given these results, investigation of the reaction scope was performed by exploring a range of substituted N-acyl lactam derivatives. These derivatives are shown in Table 1 below.

TABLE 1

| a Pd-catalyzed Enantioselective Alkylation |
| --- |

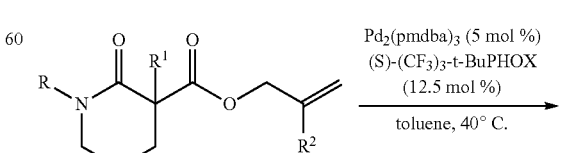

TABLE 1-continued
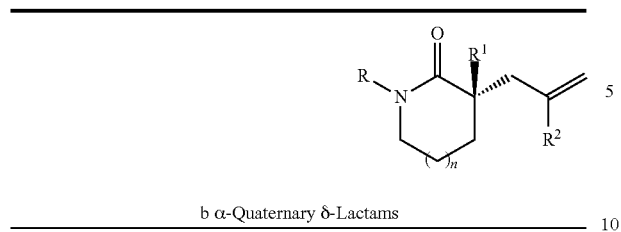
5
b α-Quaternary δ-Lactams
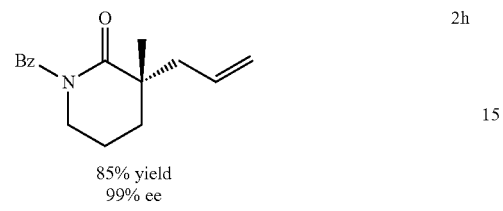
2h
85% yield
99% ee
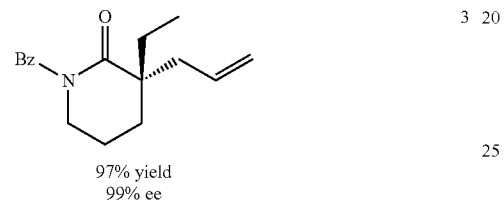
3
97% yield
99% ee
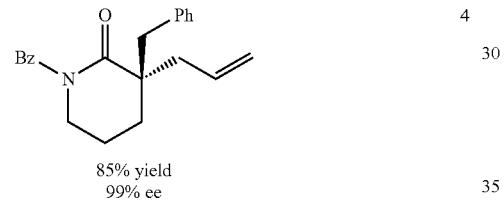
4
85% yield
99% ee
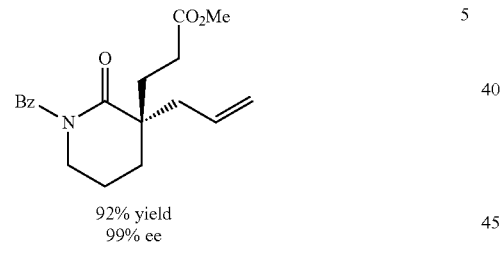
5
92% yield
99% ee
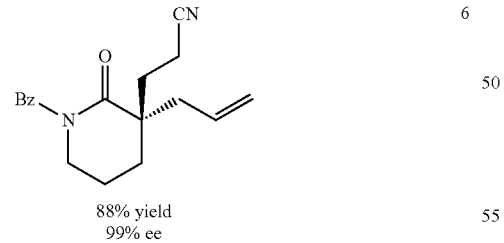
6
88% yield
99% ee
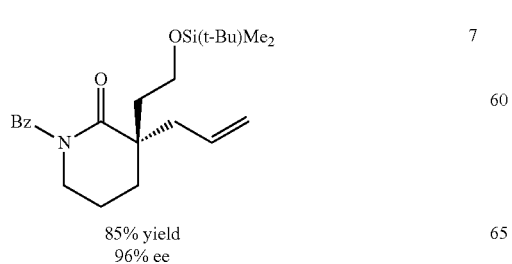
7
85% yield
96% ee
TABLE 1-continued
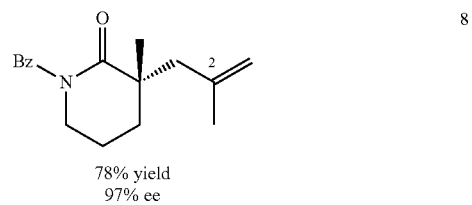
8
78% yield
97% ee
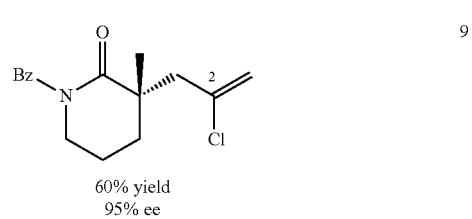
9
60% yield
95% ee
c Other Ring Sizes and Frameworks
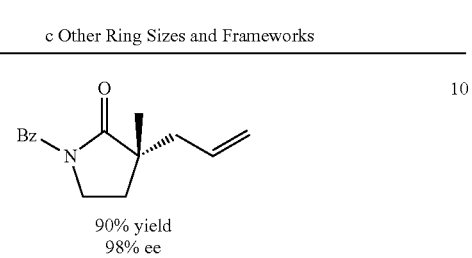
10
90% yield
98% ee
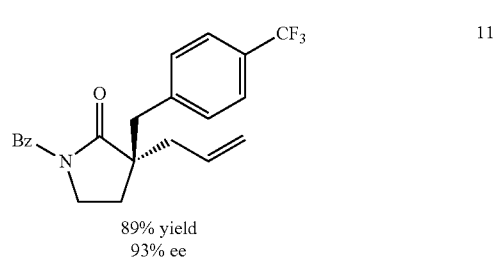
11
89% yield
93% ee
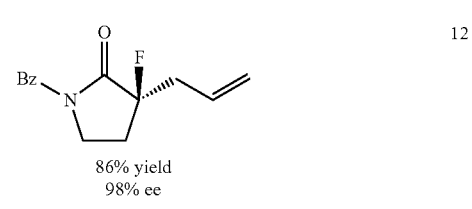
12
86% yield
98% ee
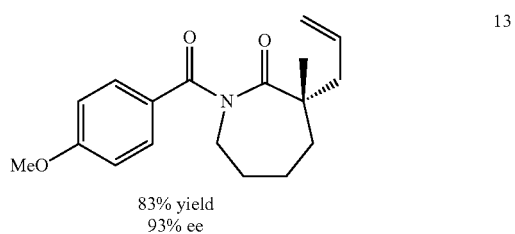
13
83% yield
93% ee
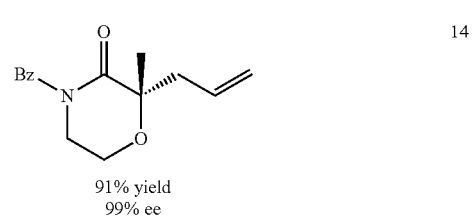
14
91% yield
99% ee

TABLE 1-continued

15 N-Bz piperidinone with F and allyl at C(α)
89% yield
99% ee

16 N-Bz glutarimide with methyl and allyl at C(α)
81% yield
94% ee

17 N-Bz glutarimide with ethyl and allyl at C(α)
86% yield
96% ee d Other N-acyl Groups

18 N-Ac piperidinone with benzyl and allyl at C(α)
90% yield
88% ee

19 N-PhOC(O) (Cbz-like phenyl carbamate) piperidinone with methyl and allyl
82% yield
94% ee

20 N-Cbz pyrrolidinone with methyl and allyl
86% yield
91% ee

21 N-(4-phenylbenzoyl) piperidinone with methyl and allyl
85% yield
99% ee

TABLE 1-continued

22 N-(1-naphthoyl) piperidinone with methyl and allyl
86% yield
99% ee

23 N-(2-naphthoyl) piperidinone with methyl and allyl
82% yield
97% ee

Importantly, reproducing the screening reaction on preparative scale furnishes the N-Bz piperidinone of Compound 2h in 85% isolated yield and 99% ee (see box (b) in Table 1 above). Alteration of the C(α)-group to other alkyl and functionalized alkyl units (e.g., —CH$_2$CH$_3$ and —CH$_2$Ph), as well as to moieties possessing additional acidic protons (e.g., —CH$_2$CH$_2$CO$_2$Me and —CH$_2$CH$_2$CN) leads to high yields of the lactams of Compounds 3 through 6 (see box b in Table 1 above) in uniformly good enantioenrichment (99% ee). Common silyl protecting groups are tolerated in the transformation and the lactam of Compound 7 is furnished in 85% yield and 96% ee. Substituted allyl groups can be incorporated, however only at C(2), leading to products such as the methallyl lactam of Compound 8 and the chloroallyl lactam of Compound 9 in good yield and enantioselectivity (≥95% ee).

Beyond piperidinones, pyrrolidinones and caprolactams are also good substrate classes, furnishing the heterocycles of Compounds 10 through 13 (see box c of Table 1 above) in good yield and ee. Additionally, the morpholine-derived product of Compound 14, containing a C(α)-tetrasubstituted tertiary center, is produced in 91% yield and 99% ee. C(α)-Fluoro substitution is readily introduced into the 1,3-dicarbonyl starting material and is viable in the enantioselective reaction leading to the fluoropyrrolidinone of Compound 12 (86% yield, 98% ee) and the fluoropiperidinone of Compound 15 (89% yield, 99% ee). Moreover, N-Bz glutarimides serve as good substrates smoothly reacting to provide the cyclic imides of Compounds 16 and 17 in high yield and enantioselectivity. Finally, alteration of the N-Bz group is possible (see box d in Table 1 above), giving lactams with an N-acetyl group (Compound 18), N-carbamates (Compounds 19 and 20), and a variety of N-aroyl derivatives (Compounds 21 through 23).

These screening procedures highlight certain methods according to the present invention. In particular, as can be seen from the screening procedures described above, according to some embodiments of the present invention, modifying the traditional transition metal catalyzed decarboxylative alkylation reaction by using an electron poor ligand yields enantioenriched compounds. As used herein, the term "electron poor" is used in its art-recognized sense, and not as a term of degree or approximation. Indeed, those of ordinary skill in the art would readily understand what is meant by the term "electron poor." However, in some embodiments, the electron poor ligand may be a (S)-t-BuPHOX in which one or more of the hydrogen atoms on the t-Bu moiety is substituted with a fluorine atom or other electron poor functional group, such as, for example, a partially or fully fluorinated hydrocarbyl or heteroatom containing hydrocarbyl group, a $NO_2$ group, or a $SO_2R$ group (in which R in $SO_2R$ is any substituted or unsubstituted hydrocarbyl, heteroatom containing hydrocarbyl, or functional group). In some embodiments, for example, the t-Bu moiety may be replaced, yielding a R'-PHOX (e.g., a (S)—R'-PHOX) ligand, in which R' may be a partially or fully fluorinated hydrocarbyl or heteroatom containing hydrocarbyl group, a $NO_2$ group, a $SO_2R$ group (in which R in $SO_2R$ is any substituted or unsubstituted hydrocarbyl, heteroatom containing hydrocarbyl, or functional group), or a hydrocarbyl or heteroatom containing hydrocarbyl group in which at least one of the hydrogen atoms is replaced by an electron poor group, such as, for example, a fluorine atom, a $NO_2$ group, or a $SO_2R$ group (in which R in $SO_2R$ is any substituted or unsubstituted hydrocarbyl, heteroatom containing hydrocarbyl, or functional group.

Accordingly, in some embodiments of the present invention, a method of preparing an enantioenriched heteroatom containing building block compound includes reaction of a heteroatom containing substrate compound with a palladium-based catalyst and an electron poor ligand in the presence of a solvent. The electron poor ligand is as described above, and the palladium catalyst is not particularly limited, and those of ordinary skill in the art would be able to select a suitable catalyst. However, nonlimiting examples of suitable catalysts include $Pd_2(dba)_3$ and $Pd_2(pmdba)_3$ (dba=dibenzylidene acetone; pmdba=di(p-methoxybenzylidene) acetone). The solvent is also not particularly limited, and can be any solvent normally used in metal catalyzed decarboxylative alkylation procedures. Some nonlimiting examples of suitable solvents include THF, MTBE, toluene, and hexane:toluene (2:1). Additional ligands, catalysts and solvents useful in the reactions according to embodiments of the present invention, and additional reaction particulars, are disclosed in U.S. Pat. No. 7,235,698 to Behenna, et al., the entire content of which is incorporated herein by reference.

The enantioenriched products formed by the catalytic asymmetric alkylation chemistry according to embodiments of the present invention can be of broad utility in synthetic chemistry. To illustrate this point, the lactam of Compound 3 can be transformed into the Aspidosperma alkaloid (+)-quebrachamine by modification of a previous route that employed a chiral auxiliary. See Amat, et al., "Enantioselective Synthesis of 3,3-Disubstituted Piperidine Derivatives by Enolate Dialkylation of Phenylglycinol-Derived Oxazolopiperidone Lactams," *J. Org. Chem.* 72, 4431-4439 (2007), the entire content of which is incorporated herein by reference. Additionally, cleavage of the N-Bz group of the lactam of Compound 3 produces the chiral lactam of Compound 24, a compound previously used as a racemate in the synthesis of rhazinilam, a microtubule-disrupting agent that displays similar cellular characteristics to paclitaxel. Edler, et al., "Demonstration of microtubule-like structures formed with (−)-rhazinilam from purified tubulin outside of cells and a simple tubulin-based assay for evaluation of analog activity," *Arch. Biochem. and Biophys.* 487, 98-104 (2009); Magnus, et al., "Concise synthesis of (±)-rhazinilam," *Tetrahedron* 57, 8647-8651 (2001), the entire contents of both of which are incorporated herein by reference. The below Synthesis Reaction Scheme depicts routes to the (+)-Quebrachamine and (+)-Rhazinilam. Finally, reduction of the lactam of Compound 24 produces the C(3)-quaternary piperidine of Compound 25 and demonstrates access to the corresponding amine building blocks.

Synthesis Reaction Scheme

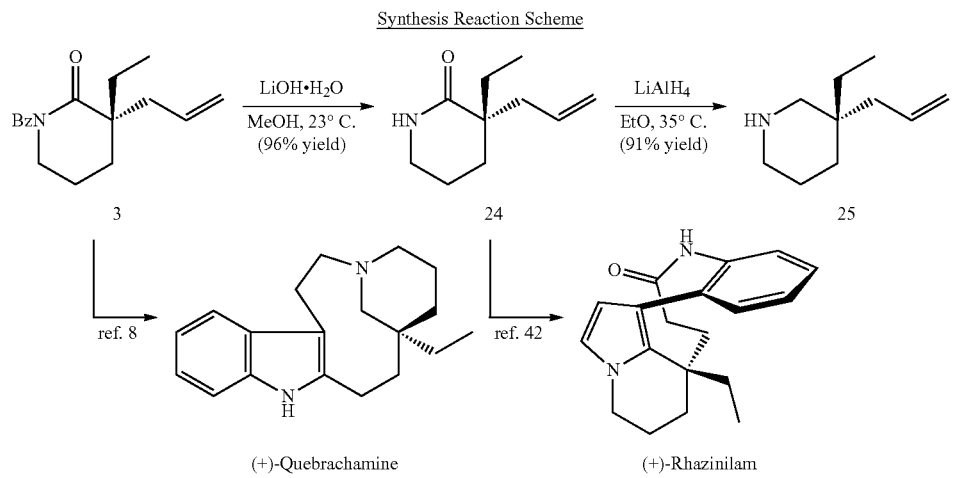

(+)-Quebrachamine (+)-Rhazinilam

In summary, embodiments of the present invention are directed to substrates useful in preparing enantioenriched quaternary N-containing compounds, and other embodiments are directed to the enantioenriched quaternary N-containing compounds. Additionally, embodiments of the present invention are directed to methods for the catalytic enantioselective alkylation of nitrogen containing derivatives (e.g., monocyclic 5-, 6-, and 7-membered lactam enolate derivatives) to form quaternary N-containing compounds (e.g., α-quaternary and α-tetrasubstituted tertiary lactams). The reaction discovery process was enabled by parallel screening of reaction parameters and led to the identification of a sterically and electronically tuned system for highly enantioselective alkylation. This method has been applied to the catalytic asymmetric synthesis of key intermediates previously employed for the construction of Aspidosperma alkaloids. Finally, the asymmetric products formed according to embodiments of the present invention are widely useful as building blocks for the preparation of a wide range of nitrogen containing compounds (including heterocycles) prevalent in materials science, medicinal chemistry and natural products.

EXPERIMENTAL

The following examples and experimental procedures are presented for illustrative purposes only, and do not limit the scope of the present invention. In the examples below and description throughout, certain terms are used as shorthand. The shorthand terms are known to those of ordinary skill in the art, however, the following Terms Table lists the shorthand used and its corresponding meaning.

Terms Table

| Shorthand | Meaning |
|---|---|
| Ts | Tosyl |
| Boc | Tert-butyloxy carbonyl group |
| Cbz | Carboxy benzyl group |
| Fmoc | Fluorenyl methyloxy carbonyl group |
| Ac | Acetyl group |
| 4-OMe-Bz | 4-methoxy-benzoyl group |
| 4-F-Bz | 4-fluoro-benzoyl group |
| Bz | Benzoyl group |
| THF | Tetrahydrofuran |
| MTBE | Methyl tert-butyl ether |
| Tol | Toluene |
| Hex:Tol | Mixed hexane and toluene solvent |
| Ph | Phenyl group |
| OPh (or PhO) | Phenyloxy group |

Materials and Methods

Unless otherwise stated, reactions were performed in flame-dried glassware under an argon or nitrogen atmosphere using dry, deoxygenated solvents. Solvents were dried by passage through an activated alumina column under argon. Brine solutions are saturated aqueous sodium chloride solutions. Tris(dibenzylideneacetone)dipalladium(0) ($Pd_2(dba)_3$) was purchased from Strem and stored in a glove box. Lithium bis(trimethylsilyl)amide was purchased from Aldrich and stored in a glove box. Tris[bis(p-methoxybenzylidene)-acetone]dipalladium(0) ($Pd_2(pmdba)_3$) was prepared by known methods and stored in a glovebox. See McDougal, et al., "High-throughput screening of the asymmetric decarboxylative alkylation reaction of enolate-stabilized enol carbonates," *Synlett* 1712-1716. (2010), the entire content of which has already been incorporated herein by reference.

(S)-t-BuPHOX, (S)—$(CF_3)_3$-t-BuPHOX, and allyl cyanoformate were prepared by known methods. See Helmchen, et al., "Phosphinooxazolines—a new class of versatile, modular P,N-ligands for asymmetric catalysis," *Acc. Chem. Res.* 33, 336-345 (2000); Tani, et al., "A facile and modular synthesis of phosphinooxazoline ligands," *Org. Lett.* 9, 2529-2531 (2007); McDougal, et al., Rapid synthesis of an electron-deficient t-BuPHOX ligand: cross-coupling of aryl bromides with secondary phosphine oxides," *Tetrahedron Lett.* 51, 5550-5554 (2010), the entire contents of all of which have already been incorporated herein by reference.

Selectfluor, methyl iodide, and ethyl iodide were purchased from Aldrich, Acros Organics, Strem, or Alfa Aesar and used as received unless otherwise stated. Sodium hydride (NaH) was purchased as a 60% dispersion in mineral oil from Acros and used as such unless otherwise stated. Triethylamine was distilled from $CaH_2$ prior to use. Acrolein, acrylonitrile, methyl acrylate, and benzoyl chloride were distilled prior to use.

Reaction temperatures were controlled by an IKAmag temperature modulator. Thin-layer chromatography (TLC) was performed using E. Merck silica gel 60 F254 precoated plates (0.25 mm) and visualized by UV fluorescence quenching, anisaldehyde, $KMnO_4$, or CAM staining. ICN Silica gel (particle size 0.032-0.063 mm) was used for flash chromatography. Analytical chiral HPLC was performed with an Agilent 1100 Series HPLC utilizing a Chiralpak (AD-H or AS) or Chiralcel (OD-H, OJ-H, or OB-H) columns (4.6 mm×25 cm) obtained from Daicel Chemical Industries, Ltd. with visualization at 220 or 254 nm. Analytical chiral SFC was performed with a JACSO 2000 series instrument utilizing Chiralpak (AD-H or AS-H) or Chiralcel (OD-H, OJ-H, or OB-H) columns (4.6 mm×25 cm), or a Chiralpak IC column (4.6 mm×10 cm) obtained from Daicel Chemical Industries, Ltd with visualization at 210 or 254 nm. Optical rotations were measured with a Jasco P-2000 polarimeter at 589 nm.

$^1$H and $^{13}$C NMR spectra were recorded on a Varian Inova 500 (at 500 MHz and 126 MHz, respectively) or a Mercury 300 (at 300 MHz and 75 MHz, respectively), and are reported relative to residual protio solvent ($CDCl_3$=7.26 and 77.0 ppm and $C_6D_6$=7.16 and 128.0 ppm, respectively). Data for $^1$H NMR spectra are reported as follows: chemical shift (δ ppm) (multiplicity, coupling constant (Hz), integration). IR spectra were recorded on a Perkin Elmer Paragon 1000 spectrometer and are reported in frequency of absorption ($cm^{-1}$). High resolution mass spectra were obtained using an Agilent 6200 Series TOF with an Agilent G1978A Multimode source in electrospray ionization (ESI), atmospheric pressure chemical ionization (APCI) or mixed (MM) ionization mode or from the Caltech Mass Spectral Facility.

Preparation of Substrates for the Ligand, Protecting Group and Solvent Screening The reactions used to probe the ligand, protecting group and solvent effects (discussed above) involved preparing a collection of racemic lactam substrates (i.e., Compounds 1a through 1h satisfying the formula for Compound 1, depicted below) for palladium-catalyzed decarboxylative allylic alkylation, and screening these substrates for reactivity and enantioselectivity across an array of solvents employing two chiral ligands, (S)-t-BuPHOX and (S)—$(CF_3)_3$-t-BuPHOX. For a description of the structure and synthesis of these ligands, see Helmchen, et al., "Phosphinooxazolines—a new class of versatile, modular P,N-ligands for asymmetric catalysis," *Acc. Chem. Res.* 33, 336-345 (2000); Tani, et al., "A facile and modular synthesis of phosphinooxazoline ligands," *Org. Lett.* 9, 2529-2531 (2007); McDougal, et al., Rapid synthesis of an electron-deficient t-BuPHOX ligand: cross-coupling of aryl bromides with secondary phosphine oxides," *Tetrahedron Lett.* 51, 5550-5554 (2010), the entire contents of all of which are incorporated herein by reference. The preparation of these compounds, and the screening reactions performed to make the enantioenriched Compounds 2a through 2h are described here.

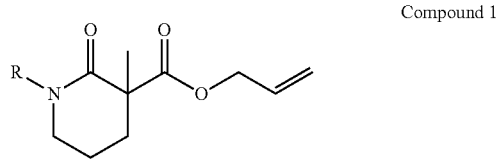

Compound 1

Generic formula for Compounds 1a through 1h

Some derivatives of Compound 1 (above) were made by a diallyl malonate method, i.e., the method represented by the below Diallyl Malonate Method Reaction Scheme.

Diallyl Malonate Method Reaction Scheme

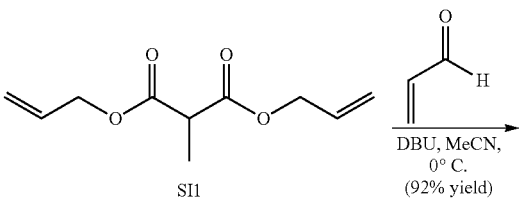

SI1

DBU, MeCN, 0° C.
(92% yield)

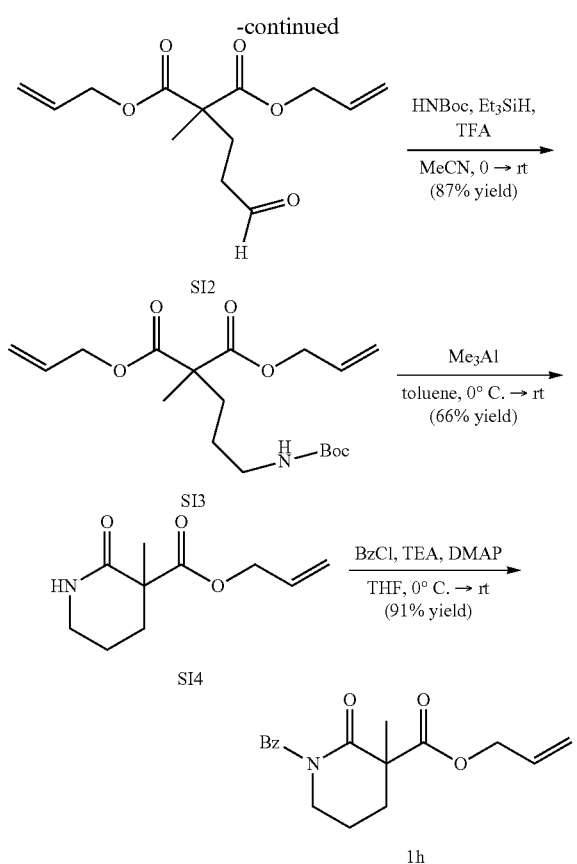

In the above Diallyl Malonate Method Reaction Scheme, aldehyde SI2, carbamate SI3, and lactam SI4 were prepared according to the following procedures. Also, although the final reaction depicted in the Diallyl Malonate Method Reaction Scheme describes the reaction used to form Compound 1h, analogous reactions can be used to form Compounds 1a through 1g, as also described below.

Aldehyde SI2: To a cooled (0° C.) solution of diallyl 2-methylmalonate (SI1)[5] (17.0 g, 84.7 mmol, 1.00 equiv) and acrolein (6.23 mL, 93.2 mmol, 1.10 equiv) in MeCN (282 mL) was added DBU (253 mL, 1.70 mmol, 0.02 equiv). After 15 min, the reaction mixture was diluted with saturated aqueous $NH_4Cl$ (200 mL) and EtOAc (100 mL) and the phases were separated. The aqueous phase was extracted with EtOAc (3×200 mL) and the combined organic phases were dried ($Na_2SO_4$), filtered, and concentrated under reduced pressure. The resulting oil was purified by flash chromatography (8×16 cm $SiO_2$, 10 to 20% EtOAc in hexanes) to afford aldehyde SI2 as a colorless oil (19.7 g, 92% yield). $R_f$=0.32 (20% EtOAc in hexanes); $^1$H NMR (300 MHz, $CDCl_3$) d 9.71 (t, J=1.2 Hz, 1H), 5.83 (ddt, J=17.2, 10.5, 5.7 Hz, 2H), 5.26 (dq, J=17.2, 1.5 Hz, 2H), 5.19 (dq, J=10.4, 1.3 Hz, 2H), 4.57 (dt, J=5.6, 1.4 Hz, 4H), 2.55-2.45 (m, 2H), 2.20-2.10 (m, 2H), 1.41 (s, 3H); $^{13}$C NMR (75 MHz, $CDCl_3$) d 200.6, 171.2, 131.3, 118.5, 65.9, 52.8, 39.2, 27.7, 20.3; IR (Neat Film NaCl) 2988, 2945, 1732, 1230, 1186, 1116, 984, 935 cm$^{-1}$; HRMS (MM: ESI-APCI) m/z calc'd for $C_{13}H_{19}O_5$ [M+H]$^+$: 255.1227. found 255.1223.

Carbamate SI3: To a cooled (0° C.) solution of aldehyde SI2 (19.7 g, 77.5 mmol, 1.00 equiv), $BocNH_2$[6] (22.7 g, 194 mmol, 2.50 equiv), and $Et_3SiH$ (31.0 mL, 194 mmol, 2.50 equiv) in MeCN (310 mL) was added trifluoroacetic acid (12.1 mL, 163 mmol, 2.10 equiv) dropwise over 5 min. The reaction mixture was stirred at 0° C. for 2 h and at ambient temperature for an additional 18 h, at which point the reaction mixture was cooled (0° C.), treated with saturated aqueous $NaHCO_3$ (150 mL), stirred for 40 min, and concentrated under reduced pressure to remove MeCN (~250 mL). The remaining material was diluted with $Et_2O$ (200 mL) and the phases were separated. The aqueous phase was extracted with $Et_2O$ (4×100 mL) and EtOAc (1×150 mL), and the combined organic phases were washed with brine (2×150 mL), dried over $Na_2SO_4$, filtered, and concentrated under reduced pressure. The resulting oil was purified by flash chromatography (8×25 cm $SiO_2$, 5 to 15% EtOAc in hexanes) to afford carbamate SI3 as a colorless oil (23.0 g, 87% yield). $R_f$=0.32 (20% EtOAc in hexanes); $^1$H NMR (300 MHz, $CDCl_3$) δ 5.88 (ddt, J=17.3, 10.4, 5.7 Hz, 2H), 5.30 (dq, J=17.2, 1.6, 1.5 Hz, 2H), 5.23 (dq, J=10.4, 1.3, 1.3 Hz, 2H), 4.61 (dt, J=5.6, 1.4 Hz, 4H), 4.55 (br s, 1H), 3.12 (q, J=6.7 Hz, 2H), 2.00-1.75 (m, 2H), 1.44 (m, 14H); $^{13}$C NMR (75 MHz, $CDCl_3$) δ 171.6, 155.8, 131.5, 118.4, 79.0, 65.7, 53.4, 40.4, 32.7, 28.3, 24.9, 19.9; IR (Neat Film NaCl) 3403, 2977, 2939, 1734, 1517, 1366, 1250, 1173, 985, 934 cm$^1$; HRMS (MM: ESI-APCI) m/z calc'd for $C_{18}H_{29}NO_6Na$ [M+Na]$^+$: 378.1887. found 378.1892.

Lactam SI4: To a cooled (0° C.) solution of carbamate SI3 (10.4 g, 30.6 mmol, 1.00 equiv) in toluene (306 mL) was added trimethylaluminum (11.7 mL, 61.1 mmol, 2.00 equiv) dropwise over 10 min. After 5 h the reaction was allowed to warm to ambient temperature and stirred for an additional 17 h. The reaction was cooled (0° C.), treated with brine (100 mL, CAUTION: Gas evolution and exotherm) in a dropwise manner over 30 min, and stirred until gas evolution ceased. The reaction mixture was then treated with saturated aqueous sodium potassium tartrate (200 mL) and stirred for 4 h. The phases were separated and the aqueous phase was extracted with EtOAc (5×150 mL). The combined organic phases were dried over $Na_2SO_4$, filtered, and concentrated under reduced pressure. The resulting oil was purified by flash chromatography (5×16 cm $SiO_2$, 45 to 65% EtOAc in hexanes) to afford lactam SI4 as a colorless oil (3.99 g, 66% yield). $R_f$=0.41 (100% EtOAc); $^1$H NMR (300 MHz, $CDCl_3$) δ 6.85 (s, 1H), 6.00-5.75 (m, 1H), 5.30 (d, J=17.1 Hz, 1H), 5.20 (d, J=10.4 Hz, 1H), 4.70-4.50 (m, 2H), 3.40-3.20 (m, 2H), 2.30-2.15 (m, 1H), 1.94-1.59 (m, 3H), 1.48 (s, 3H); $^{13}$C NMR (75 MHz, $CDCl_3$) δ 173.1, 172.0, 131.7, 118.1, 65.7, 50.1, 42.3, 33.0, 22.4, 19.3; IR (Neat Film NaCl) 3207, 3083, 2942, 2873, 1737, 1668, 1254, 1194, 1132 cm$^1$; HRMS (MM: ESI-APCI) m/z calc'd for $C_{10}H_{16}NO_3$ [M+H]$^+$: 198.1125. found 198.1117.

As discussed in more detail below with respect to the specific Compounds 1a through 1 h, reactions were performed with Compound 1 (33.6 mmol), $Pd_2(dba)_3$ (5 mol %), and ligand (12.5 mol %) in solvent (1.0 mL) at 40° C. for 72 h (dba=dibenzylideneacetone). In all cases, complete consumption of starting material and product formation was observed by thin layer chromatography on silica gel. $Pd_2$(pmdba)$_3$ (5 mol %) was used for Compounds 1a and 1b at 50° C. (pmdba=bis(4-methoxybenzylidene)acetone). Enantiomeric excess (ee) was determined by chiral GC, SFC, or HPLC.

Compound 1h-R is benzoyl

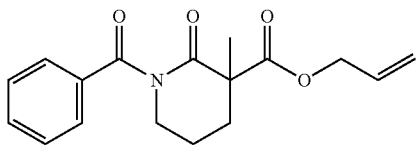

To a cooled (0° C.) solution of lactam SI4 (394 mg, 2.00 mmol, 1.00 equiv), triethylamine (840 mL, 6.00 mmol, 3.00 equiv), and DMAP (25.0 mg, 205 mmol, 0.102 equiv) in THF (8.00 mL) was added benzoyl chloride (470 mL, 4.00 mmol, 2.00 equiv) dropwise over 5 min. The reaction mixture was allowed to warm to ambient temperature and stirred for 14 h. The reaction mixture was then diluted with brine (10 mL) and EtOAc (10 mL), and the phases were separated. The aqueous phase was extracted with EtOAc (3×15 mL), and the combined organic phases were washed with brine (2×30 mL), dried over $Na_2SO_4$, filtered, and concentrated under reduced pressure. The resulting oil was purified by flash chromatography (3×25 cm $SiO_2$, 15 to 25% $Et_2O$ in hexanes) to afford benzoyl lactam 1h as an amorphous solid (550 mg, 91% yield). $R_f$=0.38 (25% EtOAc in hexanes); $^1H$ NMR (500 MHz, $CDCl_3$) δ 7.78-7.63 (m, 2H), 7.52-7.42 (m, 1H), 7.42-7.32 (m, 2H), 5.98 (ddt, J=17.2, 10.4, 5.9 Hz, 1H), 5.40 (dq, J=17.2, 1.4 Hz, 1H), 5.33 (dq, J=10.4, 1.2 Hz, 1H), 4.72 (dt, J=6.0, 1.3 Hz, 2H), 3.93-3.82 (m, 1H), 3.83-3.73 (m, 1H), 2.56-2.43 (m, 1H), 2.13-1.90 (m, 2H), 1.87-1.76 (m, 1H), 1.49 (s, 3H); $^{13}C$ NMR (126 MHz, $CDCl_3$) δ 174.9, 172.8, 172.4, 135.9, 131.6, 131.4, 128.0, 127.9, 119.5, 66.5, 52.9, 46.8, 33.8, 22.5, 20.2; IR (Neat Film NaCl) 3063, 2941, 2873, 1735, 1681, 1449, 1276, 1040, 942, 724 $cm^{-1}$; HRMS (MM: ESI-APCI) m/z calc'd for $C_{17}H_{20}NO_4$ [M+H]$^+$: 302.1387. found 302.1388.

Compound 1a

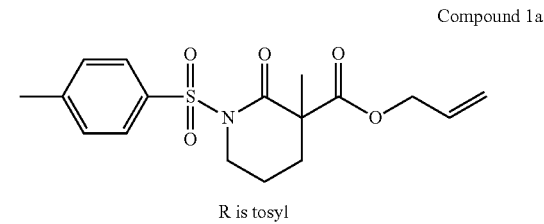 [SMILES: C=CCOC(=O)C1(C)CCCN(S(=O)(=O)c2ccc(C)cc2)C1=O]

R is tosyl

Compound 1a was made by the diallyl malonate method described above, except that the final reaction using lactam SI4 was replaced with the following final reaction scheme.

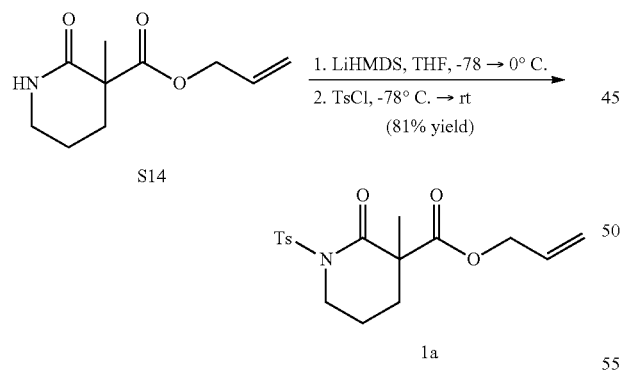

Specifically, to a cooled (−78° C.) solution of LiHMDS (385 mg, 2.30 mmol, 1.15 equiv) in THF (8.0 mL) was added lactam SI4 (394 mg, 2.00 mmol, 1.00 equiv). The reaction mixture warmed to 0° C. and stirred for 30 min, then cooled to −78° C. and treated with TsCl (572 mg, 3.00 mmol, 1.50 equiv). After 5 min, the reaction mixture was allowed to warm to ambient temperature for 30 min and treated with saturated aqueous $NH_4Cl$ (10 mL). The phases were separated, and the aqueous phase was extracted with EtOAc (3×20 mL). The combined organic phases were washed with saturated aqueous $NaHCO_3$ (20 mL) and brine (20 mL), dried over $Na_2SO_4$, filtered, and concentrated under reduced pressure. The resulting oil was purified by flash chromatography (3×30 cm $SiO_2$, 4:1:1 hexanes-EtOAc-DCM) to afford tosyl lactam 1a as a colorless oil (571 mg, 81% yield). $R_f$=0.58 (33% EtOAc in hexanes); $^1H$ NMR (500 MHz, $CDCl_3$) δ 7.93-7.83 (m, 2H), 7.35-7.27 (m, 2H), 5.68 (ddt, J=17.2, 10.5, 5.6 Hz, 1H), 5.17 (dq, J=9.1, 1.4 Hz, 1H), 5.14 (q, J=1.4 Hz, 1H), 4.47 (qdt, J=13.2, 5.6, 1.4 Hz, 2H), 3.98 (ddd, J=12.8, 6.9, 6.1 Hz, 1H), 3.90 (ddt, J=12.4, 6.0, 0.8 Hz, 1H), 2.42 (s, 3H), 2.34-2.26 (m, 1H), 1.95 (tt, J=6.5, 5.5 Hz, 2H), 1.71 (ddd, J=14.2, 8.1, 6.6 Hz, 1H), 1.41 (s, 3H); $^{13}C$ NMR (126 MHz, $CDCl_3$) δ 171.8, 169.9, 144.6, 135.7, 131.1, 129.2, 128.6, 118.7, 66.1, 52.8, 46.4, 32.4, 22.3, 21.6, 20.4; IR (Neat Film NaCl) 2942, 1740, 1691, 1353, 1284, 1167, 1090 $cm^{-1}$; HRMS (MM: ESI-APCI) m/z calc'd for $C_{17}H_{21}NO_5SNa$ [M+Na]$^+$: 374.1033. found 374.1042.

Compound 1b-R is BOC (i.e., tert-butoxycarbonyl)

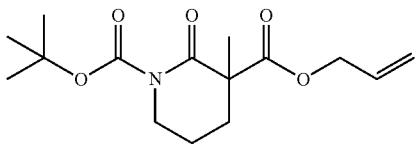

Compound 1b was prepared in a manner analogous to the tosyl lactam of Compound 1a, but using lactam SI4 (394 mg, 2.00 mmol, 1.00 equiv) and $Boc_2O$ (873 mg, 4.00 mmol, 2.00 equiv). Compound 1b (407 mg, 68% yield) was isolated as an amorphous solid by flash chromatography ($SiO_2$, 9 to 11% $Et_2O$ in hexanes). $R_f$=0.54 (25% EtOAc in hexanes); $^1H$ NMR (500 MHz, $CDCl_3$) δ 5.95-5.81 (m, 1H), 5.33 (dq, J=17.2, 1.5 Hz, 1H), 5.22 (dq, J=10.5, 1.5 Hz, 1H), 4.64 (m, 2H), 3.80-3.70 (m, 1H), 3.63-3.49 (m, 1H), 2.43-2.33 (m, 1H), 1.98-1.77 (m, 2H), 1.75-1.66 (m, 1H), 1.52 (s, 9H), 1.50 (s, 3H); $^{13}C$ NMR (126 MHz, $CDCl_3$) δ 172.5, 170.9, 153.1, 131.5, 118.4, 83.0, 65.9, 53.1, 46.0, 32.6, 28.0, 22.9, 20.1; IR (Neat Film NaCl) 2981, 2939, 1772, 1719, 1457, 1393, 1294, 1282, 1254, 1152, 988, 945, 852 $cm^{-1}$; HRMS (MM: ESI-APCI) m/z calc'd for $C_{15}H_{23}NO_5Na$ [M+Na]$^+$: 320.1468. found 320.1470.

Compound 1c-R is CBZ (i.e., carboxybenzyl)

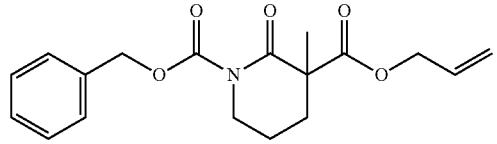

Compound 1c was prepared in a manner analogous to the tosyl lactam of Compound 1a, but using lactam SI4 (394 mg, 2.00 mmol, 1.00 equiv) and CbzCl (682 mg, 4.00 mmol, 2.00 equiv). Compound 1c (325 mg, 49% yield) was isolated as a colorless oil by flash chromatography ($SiO_2$, 14 to 17% $Et_2O$ in hexanes). $R_f$=0.34 (25% EtOAc in hexanes); $^1H$ NMR (500 MHz, $CDCl_3$) δ 7.47-7.40 (m, 2H), 7.39-7.28 (m, 3H), 5.85 (ddt, J=17.1, 10.5, 5.6 Hz, 1H), 5.30 (dq, J=10.5, 1.3 Hz, 1H), 5.29 (s, 2H), 5.19 (dq, J=10.5, 1.3 Hz, 1H), 4.69-4.54 (m, 2H), 3.86-3.79 (m, 1H), 3.71-3.60 (m, 1H), 2.44-2.37 (m, 1H), 1.98-1.78 (m, 2H), 1.73 (ddd, J=14.0, 9.1, 5.1 Hz, 1H), 1.52 (s, 3H); $^{13}C$ NMR (126 MHz, $CDCl_3$) δ 172.3, 170.9, 154.4, 135.4, 131.3, 128.5, 128.2, 128.0, 118.7, 68.6, 66.1, 53.3, 46.4, 32.5, 22.8, 20.0; IR (Neat Film NaCl) 2943, 2876, 1776, 1721, 1456, 1378, 1270, 1191, 1167, 1125, 1002, 941, 739, 698 cm$^{-1}$; HRMS (MM: ESI-APCI) m/z calc'd for C$_{18}$H$_{21}$NO$_5$Na [M+Na]$^+$: 354.1312. found 354.1310.

Compound 1d-R is FMOC (i.e., fluorenyl methyloxycarbonyl)

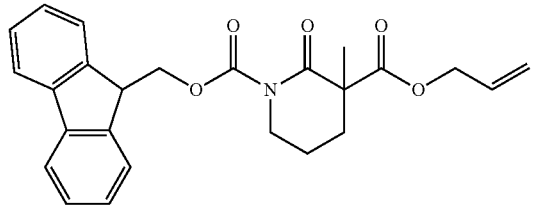

Compound 1d was prepared in a manner analogous to the tosyl lactam of Compound 1a, but using lactam SI4 (394 mg, 2.00 mmol, 1.00 equiv) and FmocCl (621 mg, 2.40 mmol, 1.20 equiv). Compound 1d (352 mg, 42% yield) was isolated as a colorless oil by flash chromatography (SiO$_2$, 2 to 12% Et$_2$O in hexanes). R$_f$=0.28 (25% EtOAc in hexanes); $^1$H NMR (500 MHz, CDCl$_3$) δ 7.77 (dt, J=7.6, 0.9 Hz, 2H), 7.73 (ddd, J=7.5, 5.0, 1.0 Hz, 2H), 7.43-7.38 (m, 2H), 7.32 (tdd, J=7.4, 4.8, 1.2 Hz, 2H), 5.91 (ddt, J=17.2, 10.5, 5.6 Hz, 1H), 5.36 (dq, J=17.2, 1.5 Hz, 1H), 5.25 (dq, J=10.5, 1.3 Hz, 1H), 4.69 (ddt, J=5.6, 2.8, 1.4 Hz, 2H), 4.56-4.43 (m, 2H), 4.33 (t, J=7.5 Hz, 1H), 3.86-3.79 (m, 1H), 3.73-3.61 (m, 1H), 2.44 (dddd, J=13.8, 6.8, 5.0, 0.9 Hz, 1H), 2.00-1.83 (m, 2H), 1.78 (ddd, J=14.0, 9.1, 5.0 Hz, 1H), 1.59 (s, 3H); $^{13}$C NMR (126 MHz, CDCl$_3$) δ 172.3, 170.9, 154.5, 143.6, 141.2, 131.4, 127.8, 127.1, 125.4, 119.9, 118.7, 69.3, 66.1, 53.4, 46.6, 46.4, 32.6, 22.9, 20.0; IR (Neat Film NaCl) 2948, 2892, 1776, 1721, 1451, 1378, 1269, 1191, 997, 759, 742 cm$^{-1}$; HRMS (MM: ESI-APCI) m/z calc'd for C$_{25}$H$_{25}$NO$_5$Na [M+Na]$^+$: 442.1625. found 442.1610.

Compound 1e-R is acetyl

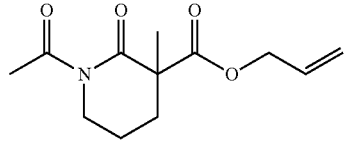

Compound 1e was prepared in a manner analogous to the benzoyl lactam of Compound 1h, but using lactam SI4 (394 mg, 2.00 mmol, 1.00 equiv), acetic anhydride (940 mL, 10.0 mmol, 5.00 equiv), and triethylamine (2.80 mL, 20.0 mmol, 10.0 equiv). Compound 1e (347 mg, 72% yield) was isolated as a colorless oil by flash chromatography (SiO$_2$, 12 to 25% Et$_2$O in hexanes). R$_f$=0.44 (25% EtOAc in hexanes); $^1$H NMR (500 MHz, CDCl$_3$) δ 5.88 (ddt, J=17.1, 10.4, 5.7 Hz, 1H), 5.31 (dq, J=17.2, 1.5 Hz, 1H), 5.25 (dq, J=10.5, 1.2 Hz, 1H), 4.66-4.60 (m, 2H), 3.78 (ddd, J=13.1, 7.6, 5.3 Hz, 1H), 3.71-3.62 (m, 1H), 2.49 (s, 3H), 2.44-2.37 (m, 1H), 1.93-1.77 (m, 2H), 1.78-1.70 (m, 1H), 1.52 (s, 3H); $^{13}$C NMR (126 MHz, CDCl$_3$) δ 174.0, 173.5, 172.4, 131.3, 119.1, 66.2, 53.2, 44.0, 32.9, 27.0, 22.7, 19.9; IR (Neat Film NaCl) 2985, 2942, 1739, 1699, 1457, 1368, 1301, 1261, 1190, 1132, 1048, 990, 959, 936 cm$^{-1}$; HRMS (MM: ESI-APCI) m/z calc'd for C$_{12}$H$_{18}$NO$_4$ [M+H]$^+$: 240.1230. found 240.1237.

Compound 1f-R is 4-OMe-Bz (i.e., 4-methoxybenzoyl)

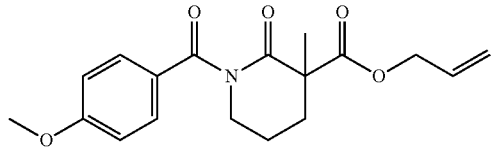

Compound 1f was prepared in a manner analogous to the benzoyl lactam of Compound 1h, but using lactam SI4 (394 mg, 2.00 mmol, 1.00 equiv), 4-methoxybenzoyl chloride (682 mg, 4.00 mmol, 2.00 equiv), and triethylamine (840 mL, 6.00 mmol, 3.00 equiv). Compound 1f (425 mg, 64% yield) was isolated as a colorless oil by flash chromatography (SiO$_2$, CHCl$_3$-hexanes-Et$_2$O 6.5:5:1). R$_f$=0.76 (50% EtOAc in hexanes); $^1$H NMR (500 MHz, CDCl$_3$) δ 7.81-7.67 (m, 2H), 6.93-6.79 (m, 2H), 6.05-5.88 (m, 1H), 5.39 (dq, J=17.2, 1.4 Hz, 1H), 5.31 (dq, J=10.4, 1.2 Hz, 1H), 4.71 (dt, J=6.0, 1.3 Hz, 2H), 3.90-3.77 (m, 1H), 3.82 (s, 3H), 3.76-3.63 (m, 1H), 2.48 (ddd, J=13.7, 5.7, 4.3 Hz, 1H), 2.06-1.89 (m, 2H), 1.80 (ddd, J=13.5, 10.0, 5.0 Hz, 1H), 1.49 (s, 3H); $^{13}$C NMR (126 MHz, CDCl$_3$) δ 174.3, 172.6 (2C), 162.7, 131.4, 130.7, 127.7, 119.3, 113.3, 66.3, 55.3, 52.8, 46.9, 33.7, 22.5, 20.2; IR (Neat Film NaCl) 3080, 2941, 1732, 1682, 1604, 1512, 1456, 1390, 1257, 1173, 1139, 1029, 939, 844, 770 cm$^{-1}$; HRMS (MM: ESI-APCI) m/z calc'd for C$_{18}$H$_{22}$NO$_5$ [M+H]$^+$: 332.1492. found 332.1501.

Compound 1g-R is 4-F-Bz (i.e., 4-fluorobenzoyl)

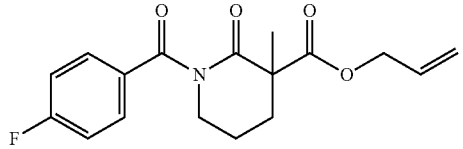

Compound 1g was prepared in a manner analogous to the benzoyl lactam of Compound 1h, but using lactam SI4 (394 mg, 2.00 mmol, 1.00 equiv), 4-fluorobenzoyl chloride (470 mL, 4.00 mmol, 2.00 equiv), and triethylamine (840 mL, 6.00 mmol, 3.00 equiv). Compound 1g (557 mg, 87% yield) was isolated as an amorphous white solid by flash chromatography (SiO$_2$, 15 to 25% Et$_2$O in hexanes). R$_f$=0.37 (25% EtOAc in hexanes); $^1$H NMR (500 MHz, CDCl$_3$) δ 7.84-7.72 (m, 2H), 7.12-6.97 (m, 2H), 5.99 (ddt, J=17.2, 10.4, 5.9 Hz, 1H), 5.41 (dq, J=17.2, 1.4 Hz, 1H), 5.35 (dq, J=10.4, 1.2 Hz, 1H), 4.73 (dt, J=6.0, 1.3 Hz, 2H), 3.89-3.82 (m, 1H), 3.81-3.75 (m, 1H), 2.57-2.42 (m, 1H), 2.09-1.91 (m, 2H), 1.89-1.75 (m, 1H), 1.50 (s, 3H); $^{13}$C NMR (126 MHz, CDCl$_3$) δ 173.8, 172.9, 172.5, 164.8 (d, J$_{C-F}$=252.5 Hz), 131.8 (d, J$_{C-F}$=3.3 Hz), 131.3, 130.7 (d, J$_{C-F}$=9.0 Hz), 119.5, 115.2 (d, J$_{C-F}$=22.0 Hz), 66.5, 52.9, 47.0, 33.8, 22.4, 20.2; IR (Neat Film NaCl) 3079, 2943, 2874, 1734, 1684, 1602, 1508, 1277, 1240, 1193, 1140, 939, 849, 770 cm$^{-1}$; HRMS (MM: ESI-APCI) m/z calc'd for C$_{17}$H$_{19}$NO$_4$F [M+H]$^+$: 320.1293. found 320.1297.

General Procedure for Allylic Alkylation Screening Reactions

The substrates described above (i.e., Compounds 1a through 1h) were then subjected to allylic alkylation reactions using different ligands and solvents and the resulting compounds (i.e., Compounds 2a through 2h) were analyzed for enantiomeric excess. The general procedure for these reactions is described here.

All reagents were dispensed as solutions using a Symyx Core Module within a nitrogen-filled glovebox. Oven-dried half-dram vials were charged with a solution of the palladium source (Pd$_2$ dba$_3$ or Pd$_2$ pmdba$_3$, 1.68 µmol, 0.05 equiv) in THF (368 µL). The palladium solutions were evaporated to dryness under reduced pressure using a Genevac centrifugal evaporator within the glovebox, and stirbars were added to the vials. The reaction vials were then charged with the desired reaction solvent (500 µL) and a solution of the PHOX ligand (4.20 µmmol, 0.125 equiv) in the reaction solvent (250 µL) and stirred at ambient glovebox temperature (~28° C.). After 30 min, solutions of the lactam substrate (33.6 µmmol, 1.0 equiv) in the reaction solvent (250 µL) were added. The reaction vials were tightly capped and heated to the desired temperature. When complete consumption of the starting material was observed by colorimetric change (from light green to red-orange) and confirmed by thin layer chromatography on SiO$_2$ (typically less than 72 h), the reaction mixtures were removed from the glovebox, concentrated under reduced pressure, resuspended in an appropriate solvent for analysis (e.g., hexanes), filtered, and analyzed for enantiomeric excess. The methods for determining the enantiomeric excess are reported in Table 4 below.

Results of the Screening of Various Reaction Parameters

The results of the enantiomeric excess analysis (by chiral HPLC (high performance liquid chromatography)) of Compounds 2a through 2h (made from Compounds 1a through 1h) over different N-protecting groups and different solvents are reported in the below Table 2.

TABLE 2

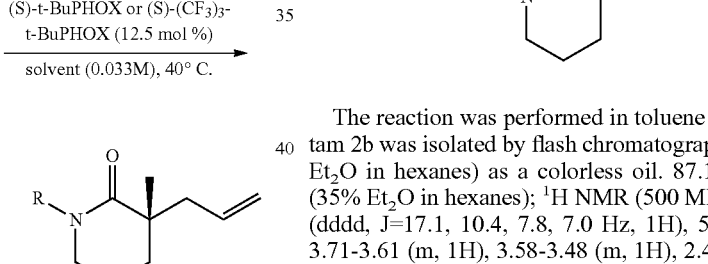

Pd$_2$dba$_3$ (5 mol %)
(S)-t-BuPHOX or (S)-(CF$_3$)$_3$-t-BuPHOX (12.5 mol %)
solvent (0.033M), 40° C.

|  | THF | MTBE | Toluene | Hex:Tol 2:1 |
|---|---|---|---|---|
| R = Ts[a] | 4.1 | 25.9 | 6.5 | 31.4 |
|  | 35.2 | 57.2 | 37.2 | 44.2 |
| R = Boc[a] | 57.3 | 74.5 | 73.6 | 76.7 |
|  | 70.3 | 72.1 | 73.0 | 71.0 |
| R = Cbz | 36.3 | 75.2 | 75.1 | 71.5 |
|  | 79.9 | 83.5 | 87.3 | 83.2 |
| R = Fmoc | 45.7 | 64.9 | 38.3 | 44.9 |
|  | 78.9 | 84.6 | 87.1 | 84.6 |
| R = Ac | 20.0 | 64.1 | 61.6 | 83.2 |
|  | 75.1 | 90.6[b] | 90.2[b] | 90.9[b] |
| R = 4-MeO—Bz | 59.5 | 90.7 | 87.4 | 96.8 |
|  | 97.1 | 98.3 | 99.0 | 98.5 |
| R = 4-F—Bz | 42.3 | 85.8 | 83.2 | 96.4 |
|  | 95.3 | 99.0 | 99.3 | 99.4 |
| R = Bz | 52.2 | 88.3 | 85.8 | 96.4 |
|  | 96.2 | 99.2 | 99.0 | 98.8 |

[a]Reactions for these substrates run at 50° C.
[b]Reaction performed at 60° C.

Characterization Data for New Product Compounds 2a through 2h

The new compounds 2a through 2h were formed using the reactions below, and characterized. The results of the characterizations are reported in Table 3 below.

Tosyl Lactam 2a

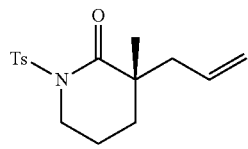

2a

The reaction was performed in MTBE at 40° C. Tosyl lactam 2a was isolated by flash chromatography (SiO$_2$, 3 to 15% Et$_2$O in hexanes) as a light yellow solid. 90.0% yield. R$_f$=0.29 (35% Et$_2$O in hexanes); $^1$H NMR (500 MHz, CDCl$_3$) δ 7.89-7.84 (m, 2H), 7.33-7.27 (m, 2H), 5.41 (dddd, J=16.9, 10.2, 8.1, 6.7 Hz, 1H), 4.99-4.86 (m, 2H), 3.99 (dddd, J=11.9, 5.9, 4.9, 1.3 Hz, 1H), 3.82-3.71 (m, 1H), 2.42 (s, 3H), 2.41-2.34 (m, 1H), 2.07 (ddt, J=13.6, 8.1, 1.0 Hz, 1H), 1.98-1.83 (m, 2H), 1.83-1.75 (m, 1H), 1.55-1.48 (m, 1H), 1.12 (s, 3H); $^{13}$C NMR (126 MHz, CDCl$_3$) δ 175.7, 144.4, 136.2, 132.9, 129.2, 128.5, 118.9, 47.6, 44.2, 44.0, 32.1, 25.5, 21.6, 20.1; IR (Neat Film NaCl) 3074, 2938, 1689, 1597, 1454, 1351, 1283, 1171, 1103, 1089, 1039, 921, 814, 748 cm$^{-1}$; HRMS (MM: ESI-APCI) m/z calc'd for C$_{16}$H$_{21}$NO$_3$SNa [M+Na]$^+$: 330.1134. found 330.1141; [α]$_D^{25}$ −69.2° (c 1.16, CHCl$_3$, 75% ee).

Boc Lactam 2b

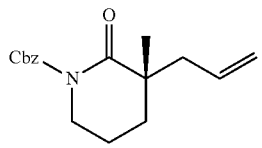

2b

The reaction was performed in toluene at 40° C. Boc lactam 2b was isolated by flash chromatography (SiO$_2$, 8 to 9% Et$_2$O in hexanes) as a colorless oil. 87.1% yield. R$_f$=0.57 (35% Et$_2$O in hexanes); $^1$H NMR (500 MHz, CDCl$_3$) δ 5.74 (dddd, J=17.1, 10.4, 7.8, 7.0 Hz, 1H), 5.14-5.02 (m, 2H), 3.71-3.61 (m, 1H), 3.58-3.48 (m, 1H), 2.48 (dd, J=13.6, 7.0 Hz, 1H), 2.26 (dd, J=13.6, 7.9 Hz, 1H), 1.87-1.76 (m, 3H), 1.61-1.52 (m, 1H), 1.50 (s, 9H), 1.22 (s, 3H); $^{13}$C NMR (126 MHz, CDCl$_3$) δ 177.1, 153.7, 133.7, 118.5, 82.5, 47.4, 44.5, 44.2, 33.0, 28.0, 25.4, 19.7; IR (Neat Film NaCl) 3076, 2978, 2936, 1768, 1715, 1457, 1392, 1368, 1298, 1280, 1252, 1149, 999, 917, 854 cm$^{-1}$; HRMS (MM: ESI-APCI) m/z calc'd for C$_{14}$H$_{23}$NO$_3$Na [M+Na]$^+$: 276.1570. found 276.1574; [α]$_D^{25}$ −73.6° (c 1.025, CHCl$_3$, 81% ee).

Cbz Lactam 2c

2c

The reaction was performed in toluene at 40° C. Cbz lactam 2c was isolated by flash chromatography (SiO$_2$, 8 to 10% Et$_2$O in hexanes) as a colorless oil. 84.6% yield. R$_f$=0.49 (25% EtOAc in hexanes); $^1$H NMR (500 MHz, CDCl$_3$) δ

7.44-7.40 (m, 2H), 7.36 (ddd, J=7.9, 7.0, 1.0 Hz, 2H), 7.33-7.29 (m, 1H), 5.74 (dddd, J=16.6, 10.5, 7.8, 6.9 Hz, 1H), 5.26 (s, 2H), 5.13-5.02 (m, 2H), 3.80-3.72 (m, 1H), 3.67-3.58 (m, 1H), 2.51 (dd, J=13.6, 7.0 Hz, 1H), 2.26 (dd, J=13.6, 7.9 Hz, 1H), 1.90-1.77 (m, 3H), 1.62-1.53 (m, 1H), 1.25 (s, 3H); $^{13}$C NMR (126 MHz, CDCl$_3$) δ 177.0, 154.8, 135.6, 133.4, 128.5, 128.2, 128.0, 118.8, 68.3, 47.8, 44.8, 44.2, 32.8, 25.5, 19.6; IR (Neat Film NaCl) 2940, 1772, 1712, 1456, 1377, 1296, 1270, 1218, 1161, 1001, 918 cm$^{-1}$; HRMS (MM: ESI-APCI) m/z calc'd for C$_{17}$H$_{20}$NO$_3$Na [M+Na]$^+$: 310.1414. found 310.1414; $[\alpha]_D^{25}$ −65.8° (c 1.48, CHCl$_3$, 86% ee).

Fmoc Lactam 2d

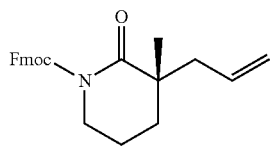

2d

The reaction was performed in toluene at 40° C. Fmoc lactam 2d was isolated by flash chromatography (SiO$_2$, 6 to 8% Et$_2$O in hexanes) as a colorless oil. 82.4% yield. R$_f$=0.45 (25% EtOAc in hexanes); $^1$H NMR (500 MHz, CDCl$_3$) δ 7.77 (dt, J=7.6, 1.0 Hz, 2H), 7.71 (ddd, J=7.5, 3.6, 1.0 Hz, 2H), 7.41 (tt, J=7.5, 0.9 Hz, 2H), 7.33 (ddt, J=7.5, 2.0, 1.2 Hz, 2H), 5.80 (dddd, J=17.9, 8.7, 7.9, 6.9 Hz, 1H), 5.18-5.10 (m, 2H), 4.53-4.42 (m, 2H), 4.33 (t, J=7.4 Hz, 1H), 3.80-3.71 (m, 1H), 3.65-3.57 (m, 1H), 2.58 (dd, J=13.6, 7.0 Hz, 1H), 2.32 (ddt, J=13.6, 7.8, 1.1 Hz, 1H), 1.93-1.79 (m, 3H), 1.64-1.57 (m, 1H), 1.31 (s, 3H); $^{13}$C NMR (126 MHz CDCl$_3$) δ 177.0, 154.9, 143.7, 141.2, 133.5, 127.7, 127.1, 125.4, 119.9, 118.8, 68.9, 47.7, 46.7, 44.8, 44.2, 32.8, 25.5, 19.6; IR (Neat Film NaCl) 3067, 2945, 1770, 1712, 1478, 1451, 1377, 1297, 1269, 1161, 1000, 759, 740 cm$^{-1}$; HRMS (MM: ESI-APCI) m/z calc'd for C$_{24}$H$_{26}$NO$_3$ [M+H]$^+$: 376.1907. found 376.1914; $[\alpha]_D^{25}$ −38.5° (c 2.17, CHCl$_3$, 89% ee).

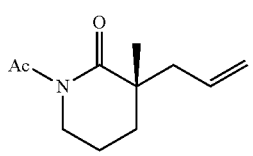

2e

Acetyl Lactam 2e

The reaction was performed in toluene at 40° C. Acetyl lactam 2e was isolated by flash chromatography (SiO$_2$, 8 to 10% Et$_2$O in hexanes) as a colorless oil. 47.2% yield. R$_f$=0.38 (25% EtOAc in hexanes); $^1$H NMR (500 MHz, CDCl$_3$) δ 5.73 (dddd, J=16.6, 10.4, 7.8, 7.0 Hz, 1H), 5.14-5.04 (m, 2H), 3.82-3.72 (m, 1H), 3.60-3.49 (m, 1H), 2.50 (ddt, J=13.6, 7.0, 1.2 Hz, 1H), 2.44 (s, 3H), 2.25 (ddt, J=13.6, 7.7, 1.1 Hz, 1H), 1.91-1.71 (m, 3H), 1.64-1.52 (m, 1H), 1.25 (s, 3H); $^{13}$C NMR (126 MHz, CDCl$_3$) δ 179.3, 174.4, 133.3, 118.9, 45.4, 44.8, 44.4, 32.8, 27.2, 25.7, 19.4; IR (Neat Film NaCl) 2941, 1694, 1387, 1367, 1293, 1248, 1177, 1114, 1046, 920 cm$^{-1}$; HRMS (MM: ESI-APCI) m/z calc'd for C$_{11}$H$_{18}$NO$_2$ [M+H]$^+$: 196.1332. found 196.1329; $[\alpha]_D^{25}$ −100.9° (c 0.99, CHCl$_3$, 91% ee).

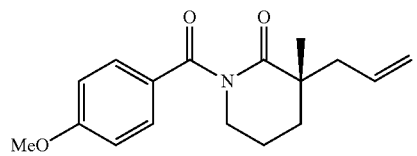

2f

4-Methoxybenzoyl Lactam 2f

The reaction was performed in toluene at 40° C. 4-Methoxybenzoyl lactam 2f was isolated by flash chromatography (SiO$_2$, 15% EtOAc in hexanes) as a colorless oil. 92.7% yield. R$_f$=0.36 (25% EtOAc in hexanes); $^1$H NMR (500 MHz, CDCl$_3$) δ 7.60-7.48 (m, 2H), 6.92-6.82 (m, 2H), 5.76 (dddd, J=17.2, 10.3, 7.7, 7.0 Hz, 1H), 5.19-5.03 (m, 2H), 3.83 (s, 3H), 3.80 (ddd, J=12.1, 5.3, 1.4 Hz, 1H), 3.73-3.64 (m, 1H), 2.57 (ddt, J=13.6, 7.1, 1.2 Hz, 1H), 2.29 (ddt, J=13.7, 7.6, 1.1 Hz, 1H), 2.05-1.91 (m, 3H), 1.72-1.63 (m, 1H), 1.32 (s, 3H); $^{13}$C NMR (126 MHz, CDCl$_3$) δ 179.0, 174.9, 162.4, 133.4, 130.1, 128.4, 118.9, 113.5, 55.4, 47.3, 43.9, 43.4, 33.3, 25.3, 19.6; IR (Neat Film NaCl) 2937, 1675, 1604, 1511, 1254, 1164, 1029, 922, 840, 770 cm$^{-1}$; HRMS (MM: ESI-APCI) m/z calc'd for C$_{17}$H$_{22}$NO$_3$ [M+H]$^+$: 288.1594. found 288.1595; $[\alpha]_D^{25}$ −94.2° (c 1.00, CHCl$_3$, 99% ee).

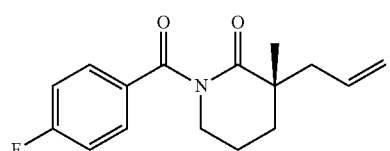

2g

4-Fluorobenzoyl Lactam 2g

The reaction was performed in toluene at 40° C. 4-Fluorobenzoyl lactam 2g was isolated by flash chromatography (SiO$_2$, 9% Et$_2$O in hexanes) as a colorless oil. 89.4% yield. R$_f$=0.41 (17% EtOAc in hexanes); $^1$H NMR (500 MHz, CDCl$_3$) δ 7.59-7.47 (m, 2H), 7.12-6.99 (m, 2H), 5.74 (ddt, J=17.0, 10.4, 7.3 Hz, 1H), 5.18-5.05 (m, 2H), 3.89-3.77 (m, 1H), 3.77-3.63 (m, 1H), 2.55 (dd, J=13.7, 7.0 Hz, 1H), 2.28 (dd, J=13.7, 7.6 Hz, 1H), 2.07-1.88 (m, 3H), 1.76-1.62 (m, 1H), 1.31 (s, 3H); $^{13}$C NMR (126 MHz, CDCl$_3$) δ 179.1, 174.2, 164.6 (d, J$_{C-F}$=252.4 Hz), 133.2, 132.5 (d, J$_{C-F}$=3.4 Hz), 123.0 (d, J$_{C-F}$=8.9 Hz), 119.1, 115.3 (d, J$_{C-F}$=22.1 Hz), 47.3, 44.0, 43.3, 33.3, 25.2, 19.5; IR (Neat Film NaCl) 3076, 2940, 1679, 1602, 1507, 1384, 1280, 1145, 922, 844, 769 cm$^{-1}$; HRMS (MM: ESI-APCI) m/z calc'd for C$_{16}$H$_{19}$NO$_2$F [M+H]$^+$: 276.1394. found 276.1392; $[\alpha]_D^{25}$ −85.5° (c 1.02, CHCl$_3$, 99% ee).

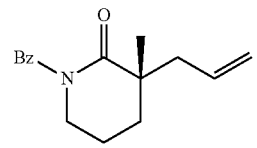

2h

Benzoyl Lactam 2h

The reaction was performed in toluene at 40° C. Benzoyl lactam 2h was isolated by flash chromatography (SiO$_2$, 5 to 9% Et$_2$O in pentane) as a colorless oil. 84.7% yield. R$_f$=0.55 (25% EtOAc in hexanes); $^1$H NMR (500 MHz, CDCl$_3$) δ 7.54-7.50 (m, 2H), 7.49-7.43 (m, 1H), 7.40-7.35 (m, 2H), 5.75 (dddd, J=17.1, 10.2, 7.7, 7.0 Hz, 1H), 5.19-5.03 (m, 2H), 3.92-3.78 (m, 1H), 3.72 (ddt, J=12.6, 6.4, 6.0, 1.2 Hz, 1H), 2.55 (ddt, J=13.7, 7.0, 1.2 Hz, 1H), 2.29 (ddt, J=13.7, 7.7, 1.1 Hz, 1H), 2.07-1.87 (m, 3H), 1.75-1.60 (m, 1H), 1.31 (s, 3H); $^{13}$C NMR (126 MHz, CDCl$_3$) δ 179.0, 175.3, 136.5, 133.3, 131.3, 128.1, 127.4, 118.9, 47.1, 44.0, 43.3, 33.3, 25.1, 19.5; IR (Neat Film NaCl) 3074, 2939, 2870, 1683, 1478, 1449, 1386, 1282, 1151, 919, 726, 695 cm$^{-1}$; HRMS (MM: ESI-APCI) m/z calc'd for C$_{16}$H$_{20}$NO$_2$ [M+H]$^+$: 258.1489. found 258.1491; [α]$_D^{25}$ −91.2° (c 1.07, CHCl$_3$, 99% ee).

TABLE 3

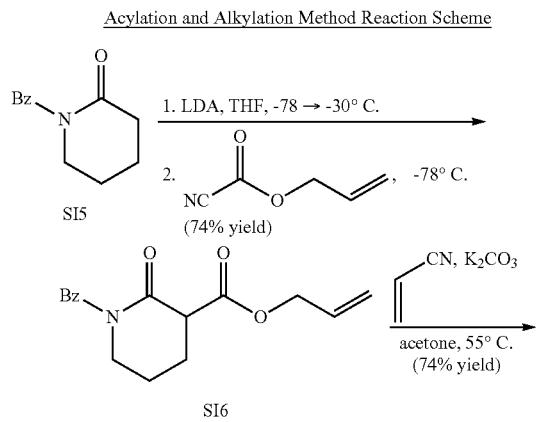

| entry | temperature (° C.) | concentration (M) | time (h) | % ee |
|---|---|---|---|---|
| 1 | 40 | 0.033 | 43 | 99.2 |
| 2 | 45 | 0.033 | 22 | 98.9 |
| 3 | 50 | 0.033 | 12 | 98.7 |
| 4 | 55 | 0.033 | 6 | 98.2 |
| 5 | 40 | 0.10 | 43 | 98.9 |
| 6 | 40 | 0.20 | 43 | 97.4 |

Preparation of Substrates for the Creation of N-Acyl Lactam Derivatives

The N-acyl lactam derivatives discussed above and depicted in Table 1, above, were prepared using substrates prepared according to an Acylation and Alkylation Method. A representative reaction scheme for the acylation and alkylation method is depicted in the below Acylation and Alkylation Method Reaction Scheme.

Acylation and Alkylation Method Reaction Scheme

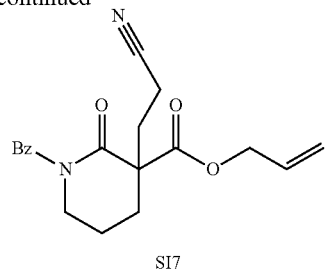

In the above Acylation and Alkylation Method Reaction Scheme, acyl lactam SI6 and benzoyl lactam SI6 were prepared according to the following procedures. Also, although the final reaction depicted in the Acylation and Alkylation Method Reaction Scheme describes the reaction used to form benzoyl lactam SI7, analogous reactions can be used to form substrates for certain of the remaining compounds depicted in Table 1 above. as also described below. Additionally, some of the substrates were formed using the diallyl malonate method described above, as described below.

Acyl Lactam SI6: To a cooled (0° C.) solution of diisopropylamine (3.33 mL, 23.6 mmol, 1.20 equiv) in THF (131 mL) was added a solution of n-BuLi (8.84 mL, 21.7 mmol, 2.45 M in hexanes, 1.10 equiv) dropwise over 10 min. After 30 min at 0° C., the reaction mixture was cooled to −78° C. A solution of benzoyl lactam SI5$^7$ (4.00 g, 19.7 mmol, 1.00 equiv) in THF (25 mL) was added dropwise over 10 min. After an additional 2 h, the reaction mixture was warmed to −30° C. for 1 h, cooled to −78° C., and treated with allyl cyanoformate (2.41 g, 21.7 mmol, 1.10 equiv). The reaction mixture was maintained at −78° C. for 2 h, allowed to warm to ambient temperature with stirring over 14 h, and diluted with half-saturated brine (100 mL) and EtOAc (100 mL). The phases were separated, and the aqueous phase was extracted with EtOAc (4×100 mL). The combined organic phases were washed with brine (2×100 mL), dried over Na$_2$SO$_4$, filtered, and concentrated under reduced pressure. The resulting oil was purified by flash chromatography (5×30 cm SiO$_2$, 15 to 30% EtOAc in hexanes) to afford acyl lactam SI6 as a colorless oil (4.18 g, 74% yield). R$_f$=0.43 (35% EtOAc in hexanes); $^1$H NMR (500 MHz, CDCl$_3$) δ 7.75-7.62 (m, 2H), 7.52-7.43 (m, 1H), 7.42-7.33 (m, 2H), 5.95 (ddt, J=17.2, 10.4, 5.9 Hz, 1H), 5.37 (dq, J=17.2, 1.5 Hz, 1H), 5.29 (dq, J=10.4, 1.2 Hz, 1H), 4.75-4.60 (m, 2H), 3.95-3.72 (m, 2H), 3.59 (t, J=6.4 Hz, 1H), 2.42-2.25 (m, 1H), 2.26-2.14 (m, 1H), 2.12-2.03 (m, 1H), 2.01-1.89 (m, 1H); $^{13}$C NMR (126 MHz, CDCl$_3$) δ 174.5, 169.5, 169.2, 135.4, 131.9, 131.4, 128.2, 128.1, 119.3, 66.4, 51.1, 46.3, 25.5, 20.7; IR (Neat Film NaCl) 3063, 2952, 1738, 1682, 1449, 1284, 1152, 730, 700 cm$^{-1}$; HRMS (MM: ESI-APCI) m/z calc'd for C$_{16}$H$_{18}$NO$_4$ [M+H]$^+$: 288.1230. found 288.1221.

Benzoyl Lactam SI7: To a mixture of acyl lactam SI6 (750 mg, 2.61 mmol, 1.00 equiv) K$_2$CO$_3$ (1.80 g, 13.1 mmol, 5.00 equiv) in acetone (10.5 mL) was added acrylonitrile (344 μL, 5.22 mmol, 2.00 equiv). The reaction mixture was heated (55° C.) for 6 h, then cooled to ambient temperature and filtered. The retentate was washed with acetone (2×10 mL). The combined organic phases were concentrated under reduced pressure. The resulting oil was purified by flash chromatography (3×30 cm SiO$_2$, 5 to 30% EtOAc in hexanes) to afford benzoyl lactam SI7 as a colorless oil (654 mg, 74% yield). R$_f$=0.23 (20% EtOAc in hexanes developed twice); $^1$H NMR (500 MHz, CDCl$_3$) δ 7.77-7.66 (m, 2H), 7.56-7.45 (m, 1H), 7.43-7.34 (m, 2H), 6.00 (ddt, J=17.2, 10.3, 6.2 Hz, 1H), 5.44 (dq, J=17.1, 1.3 Hz, 1H), 5.38 (dq, J=10.3, 1.1 Hz, 1H), 4.77 (ddt, J=6.1, 3.1, 1.2 Hz, 2H), 3.85 (ddd, J=13.0, 9.6, 5.4 Hz, 1H), 3.76 (ddt, J=13.0, 4.9, 1.4 Hz, 1H), 2.61 (ddd, J=17.0, 8.4, 6.9 Hz, 1H), 2.53-2.35 (m, 2H), 2.22 (ddd, J=8.8, 6.7, 1.6 Hz, 2H), 2.12-1.95 (m, 2H), 1.89 (ddd, J=13.6, 10.1, 5.3 Hz, 1H); $^{13}$C NMR (126 MHz, CDCl$_3$) δ 174.6, 171.2, 170.6, 135.4, 132.0, 130.8, 128.2, 128.1, 120.5, 119.1, 67.0, 55.4, 46.4, 31.7, 31.5, 20.0, 13.5; IR (Neat Film NaCl) 3067, 2952, 2248, 1733, 1683, 1449, 1271, 1196, 1175, 1152, 943, 725 cm$^{-1}$; HRMS (MM: ESI-APCI) m/z calc'd for C$_{19}$H$_{21}$N$_2$O$_4$ [M+H]$^+$: 341.1496. found 341.1492.

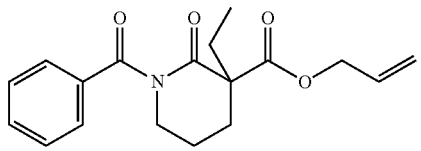

Benzoyl Lactam SI8

Benzoyl lactam SI8 was prepared by the diallyl malonate method using diallyl 2-ethylmalonate as a starting material. Benzoyl lactam SI8 was isolated by flash chromatography (SiO$_2$, 15 to 25% Et$_2$O in hexanes) as a colorless oil. R$_f$=0.38 (35% Et$_2$O in hexanes); $^1$H NMR (500 MHz, CDCl$_3$) δ 7.72-7.67 (m, 2H), 7.51-7.43 (m, 1H), 7.37 (dd, J=8.3, 7.1 Hz, 2H), 5.99 (ddt, J=17.3, 10.4, 5.9 Hz, 1H), 5.40 (dq, J=17.2, 1.4 Hz, 1H), 5.33 (dq, J=10.4, 1.2 Hz, 1H), 4.73 (dt, J=6.0, 1.3 Hz, 2H), 3.93-3.63 (m, 2H), 2.43 (ddt, J=13.7, 4.4, 1.4 Hz, 1H), 2.17-1.65 (m, 5H), 0.91 (t, J=7.4 Hz, 3H); $^{13}$C NMR (126 MHz, CDCl$_3$) δ 175.0, 172.0, 171.8, 135.9, 131.6, 131.4, 128.0 (2C), 119.5, 66.4, 56.9, 46.4, 29.8, 28.6, 20.3, 9.0; IR (Neat Film NaCl) 3062, 2943, 2882, 1732, 1678, 1449, 1385, 1268, 1188, 1137, 980, 937, 723, 693, 660 cm$^{-1}$; HRMS (MM: ESI-APCI) m/z calc'd for C$_{18}$H$_{22}$NO$_4$ [M+H]$^+$: 316.1543. found 316.1545.

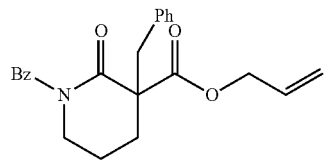

Benzoyl Lactam SI9

Benzoyl lactam SI9 was prepared by the diallyl malonate method using diallyl 2-benzylmalonate as a starting material. Benzoyl lactam SI9 was isolated by flash chromatography (SiO$_2$, 15 to 35% Et$_2$O in hexanes) as a colorless oil. R$_f$=0.32 (35% Et$_2$O in hexanes); $^1$H NMR (500 MHz, CDCl$_3$) δ 7.72 (dt, J=8.2, 0.9 Hz, 2H), 7.56-7.45 (m, 1H), 7.45-7.35 (m, 2H), 7.30-7.18 (m, 3H), 7.17-7.10 (m, 2H), 6.00 (ddt, J=17.2, 10.4, 6.0 Hz, 1H), 5.43 (dq, J=17.2, 1.4 Hz, 1H), 5.36 (dq, J=10.4, 1.1 Hz, 1H), 4.75 (dq, J=6.1, 1.1 Hz, 2H), 3.70 (dddd, J=12.9, 5.0, 4.3, 1.7 Hz, 1H), 3.59 (ddd, J=12.9, 10.5, 4.6 Hz, 1H), 3.47 (d, J=13.7 Hz, 1H), 3.14 (d, J=13.7 Hz, 1H), 2.36 (ddt, J=13.7, 4.3, 1.7 Hz, 1H), 2.07-1.92 (m, 1H), 1.91-1.75 (m, 2H); $^{13}$C NMR (126 MHz, CDCl$_3$) δ 175.0, 171.5, 171.3, 135.9, 135.7, 131.8, 131.2, 130.9, 128.3, 128.2, 128.0, 127.0, 119.8, 66.7, 57.8, 46.2, 40.6, 29.8, 20.1; IR (Neat Film NaCl) 3062, 3029, 2941, 2890, 1731, 1701, 1682, 1449, 1273, 1190, 1147, 934, 723, 702, 661 cm$^{-1}$; HRMS (MM: ESI-APCI) m/z calc'd for C$_{23}$H$_{24}$NO$_4$ [M+H]$^+$: 378.1700. found 378.1706.

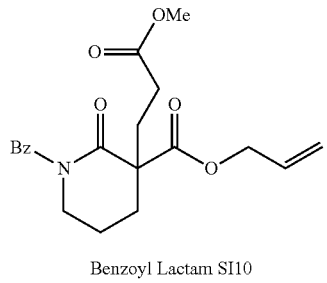

Benzoyl Lactam SI10

Benzoyl lactam SI10 was prepared by the acylation and alkylation method using methyl acrylate as an alkylating reagent. Benzoyl lactam SI10 was isolated by flash chromatography (SiO$_2$, 40 to 50% Et$_2$O in hexanes) as a colorless oil. R$_f$=0.28 (35% Et$_2$O in hexanes); $^1$H NMR (500 MHz CDCl$_3$) δ 7.78-7.66 (m, 2H), 7.52-7.42 (m, 1H), 7.38 (t, J=7.7 Hz, 2H), 6.04-5.93 (m, 1H), 5.41 (dq, J=17.1, 1.1 Hz, 1H), 5.35 (dt, J=10.4, 1.0 Hz, 1H), 4.79-4.68 (m, 2H), 3.88-3.79 (m, 1H), 3.79-3.72 (m, 1H), 3.63 (s, 3H), 2.56-2.41 (m, 2H), 2.40-2.28 (m, 1H), 2.27-2.18 (m, 2H), 2.08-1.92 (m, 2H), 1.85 (ddd, J=15.2, 9.8, 5.7 Hz, 1H); $^{13}$C NMR (126 MHz, CDCl$_3$) δ 174.8, 173.1, 171.6, 171.3, 135.7, 131.7, 131.1, 128.0 (2C), 119.9, 66.6, 55.8, 51.7, 46.4, 31.0, 30.5, 29.7, 20.1; IR (Neat Film NaCl) 2952, 1735, 1685, 1449, 1273, 1194, 1174, 726 cm$^{-1}$; HRMS (MM: ESI-APCI) m/z calc'd for C$_{20}$H$_{24}$NO$_6$ [M+H]$^+$: 374.1598. found 374.1592.

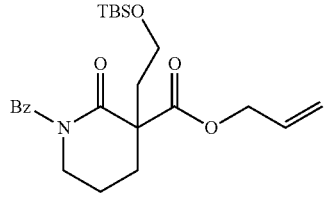

Benzoyl Lactam SI11

Benzoyl lactam SI11 was prepared the acylation and alkylation method, above, using (2-bromoethoxy)-tert-butyldimethylsilane as an alkylating reagent. Benzoyl lactam SI11 was isolated by flash chromatography (SiO$_2$, 10 to 40% Et$_2$O in hexanes) as a colorless oil. R$_f$=0.18 (10% Et$_2$O in hexanes); $^1$H NMR (500 MHz CDCl$_3$) δ 7.74-7.62 (m, 2H), 7.52-7.42 (m, 1H), 7.40-7.30 (m, 2H), 5.98 (ddt, J=17.1, 10.4, 6.0 Hz, 1H), 5.40 (dq, J=17.2, 1.4 Hz, 1H), 5.33 (dq, J=10.4, 1.2 Hz, 1H), 4.72 (dt, J=6.0, 1.3 Hz, 2H), 3.80 (ddt, J=6.4, 4.8, 2.4 Hz, 2H), 3.72 (td, J=6.4, 0.8 Hz, 2H), 2.55-2.31 (m, 1H), 2.23 (dt, J=14.1, 6.6 Hz, 1H), 2.16-2.03 (m, 2H), 2.02-1.92 (m, 2H), 0.86 (s, 9H), 0.01 (s, 3H), 0.00 (s, 3H); $^{13}$C NMR (126 MHz, CDCl$_3$) δ 175.0, 171.7 (2C), 136.0, 131.6, 131.4, 128.0 (2C), 119.6, 66.5, 59.5, 55.3, 46.4, 37.8, 30.6, 25.9, 20.3, 18.2, −5.45, −5.47; IR (Neat Film NaCl) 2954, 2929, 2884, 2856, 1735, 1703, 1683, 1276, 1255, 1143, 1092, 836 cm$^{-1}$; HRMS (MM: ESI-APCI) m/z calc'd for C$_{24}$H$_{36}$NO$_5$Si [M+H]$^+$: 446.2357. found 446.2361.

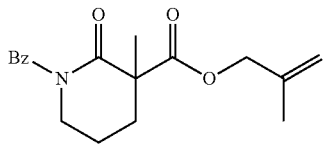

Benzoyl Lactam SI12

Benzoyl lactam SI12 was prepared by the diallyl malonate using dimethallyl malonate as a starting material. Benzoyl lactam SI12 was isolated by flash chromatography (SiO$_2$, 14 to 20% Et$_2$O in hexanes) as an amorphous white solid. R$_f$=0.47 (25% EtOAc in hexanes); $^1$H NMR δ 7.73-7.68 (m, 2H), 7.49-7.44 (m, 1H), 7.37 (ddd, J=8.1, 6.7, 1.2 Hz, 2H), 5.05 (s, 1H), 5.01 (s, 1H), 4.65 (dd, J=17.5, 10.0 Hz, 2H), 3.87 (ddd, J=12.9, 8.8, 5.6 Hz, 1H), 3.80 (ddt, J=12.9, 5.2, 1.4 Hz, 1H), 2.55-2.46 (m, 1H), 2.08-1.95 (m, 2H), 1.86-1.79 (m, 1H), 1.79 (s, 3H), 1.50 (s, 3H); $^{13}$C NMR (126 MHz, CDCl$_3$) δ 174.9, 172.8, 172.5, 139.3, 135.9, 131.6, 128.0 (2C), 114.2, 69.1, 53.0, 46.8, 33.8, 22.5, 20.3, 19.6; IR (Neat Film NaCl) 2941, 2873, 1735, 1682, 1449, 1276, 1192, 1140, 940, 724, 694, 659 cm$^{-1}$; HRMS (MM: ESI-APCI) m/z calc'd for C$_{18}$H$_{21}$NO$_4$Na [M+Na]$^+$: 338.1363. found 338.1373.

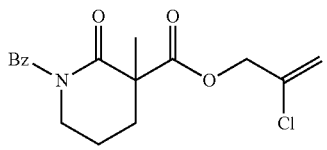

Benzoyl Lactam SI13

Benzoyl lactam SI13 was prepared by the diallyl malonate method using di-2-chloroallyl malonate as a starting material. Benzoyl lactam SI13 was isolated by flash chromatography (SiO$_2$, 14 to 20% Et$_2$O in hexanes) as a colorless oil. R$_f$=0.47 (25% EtOAc in hexanes); $^1$H NMR (500 MHz, CDCl$_3$) δ 7.76-7.64 (m, 2H), 7.56-7.41 (m, 1H), 7.43-7.31 (m, 2H), 5.54 (dt, J=2.0, 1.1 Hz, 1H), 5.48 (d, J=1.8 Hz, 1H), 4.80 (qd, J=13.4, 1.0 Hz, 2H), 3.89 (ddd, J=12.9, 8.9, 5.1 Hz, 1H), 3.80 (ddt, J=13.0, 5.3, 1.3 Hz, 1H), 2.52 (dddd, J=13.8, 5.6, 4.1, 1.3 Hz, 1H), 2.11-1.94 (m, 2H), 1.85 (ddd, J=13.8, 10.2, 4.5 Hz, 1H), 1.53 (s, 3H); $^{13}$C NMR (126 MHz, CDCl$_3$) δ 174.9, 172.5, 172.1, 135.8, 135.3, 131.7, 128.1, 128.0, 116.4, 67.1, 52.9, 46.7, 33.7, 22.5, 20.1; IR (Neat Film NaCl) 2943, 2873, 1740, 1682, 1449, 1390, 1276, 1192, 1124, 1061, 943, 724, 695 cm$^{-1}$; HRMS (MM: ESI-APCI) m/z calc'd for C$_{17}$H$_{18}$NO$_4$ClNa [M+Na]$^+$: 358.0817 found 358.0819.

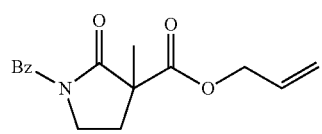

Benzoyl Lactam SI14

Benzoyl lactam SI14 was prepared by the acylation and alkylation method using N-benzoyl pyrrolidinone as a starting material and methyl iodide as an alkylating reagent. See Amat, et al., "Enantioselective Synthesis of 3,3-Disubstituted Piperidine Derivatives by Enolate Dialkylation of Phenylglycinol-derived Oxazolopiperidone Lactams," *J. Org. Chem.* 72, 4431-4439 (2007), the entire content of which is incorporated herein by reference. Benzoyl lactam SI14 was isolated by flash chromatography (SiO$_2$, 5 to 20% EtOAc in hexanes) as a colorless oil. R$_f$=0.45 (35% EtOAc in hexanes); $^1$H NMR (500 MHz, CDCl$_3$) δ 7.64-7.55 (m, 2H), 7.56-7.46 (m, 1H), 7.45-7.35 (m, 2H), 5.92 (ddt, J=17.2, 10.5, 5.7 Hz, 1H), 5.34 (dq, J=17.2, 1.5 Hz, 1H), 5.28 (dq, J=10.4, 1.2 Hz, 1H), 4.67 (dt, J=5.7, 1.4 Hz, 2H), 4.02 (ddd, J=11.3, 8.4, 4.6 Hz, 1H), 3.95 (dt, J=11.3, 7.7 Hz, 1H), 2.64 (ddd, J=13.2, 7.7, 4.5 Hz, 1H), 2.06 (ddd, J=13.2, 8.5, 7.6 Hz, 1H), 1.51 (s, 3H); $^{13}$C NMR (126 MHz CDCl$_3$) δ 173.0, 170.9, 170.5, 133.9, 132.0, 131.2, 128.8, 127.8, 119.0, 66.4, 53.8, 43.3, 30.5, 20.0; IR (Neat Film NaCl) 2985, 2938, 1750, 1738, 1733, 1683, 1449, 1362, 1307, 1247, 1196, 1136, 972, 937, 860, 730, 699, 656 cm$^{-1}$; HRMS (MM: ESI-APCI) m/z calc'd for C$_{16}$H$_{18}$NO$_4$ [M+H]$^+$: 288.1230. found 288.1228.

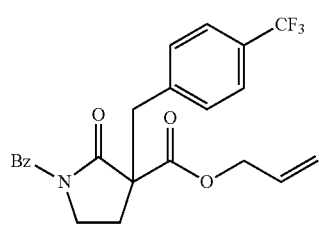

Benzoyl Lactam SI15

Benzoyl lactam SI15 was prepared by the acylation and alkylation method using N-benzoyl pyrrolidinone as a starting material and 4-(trifluoromethyl)benzyl bromide as an alkylating reagent. See Enders, et al., "Asymmetric Electrophilic Substitutions at the α-Position of γ- and δ-Lactams," *Eur. J. Org. Chem.* 4463-4477 (2011), the entire content of which is incorporated herein by reference. Benzoyl lactam SI15 was isolated by flash chromatography (SiO$_2$, 10 to 20% EtOAc in hexanes) as a colorless oil. R$_f$=0.28 (20% EtOAc in hexanes); $^1$H NMR (500 MHz, CDCl$_3$) δ 7.58 (d, J=7.9 Hz, 2H), 7.56-7.49 (m, 3H), 7.44-7.38 (m, 2H), 7.35 (d, J=7.9 Hz, 2H), 5.92 (ddt, J=17.3, 10.4, 5.8 Hz, 1H), 5.36 (dq, J=17.2, 1.4 Hz, 1H), 5.30 (dq, J=10.5, 1.2 Hz, 1H), 4.70 (dq, J=5.8, 1.2 Hz, 2H), 3.84 (ddd, J=11.2, 8.6, 7.6 Hz, 1H), 3.66 (ddd, J=11.2, 8.8, 3.2 Hz, 1H), 3.39 (d, J=14.0 Hz, 1H), 3.31 (d, J=13.9 Hz, 1H), 2.51 (ddd, J=13.3, 7.6, 3.3 Hz, 1H), 2.15 (dt, J=13.3, 8.7 Hz, 1H); $^{13}$C NMR (126 MHz, CDCl$_3$) δ 171.3, 170.2, 169.8, 139.7 (d, J$_{C-F}$=1.5 Hz), 133.7, 132.3, 131.0, 130.9, 129.8 (q, J$_{C-F}$=32.5 Hz), 128.9, 127.9, 125.5 (q, J$_{C-F}$=3.8 Hz), 124.0 (q, J$_{C-F}$=272.0 Hz), 119.5, 66.8, 59.0, 43.6, 38.4, 26.2; IR (Neat Film NaCl) 3062, 2938, 2913, 1751, 1733, 1683, 1449, 1366, 1326, 1294, 1250, 1193, 1165, 1116, 1068, 861, 728 cm$^{-1}$; HRMS (MM: ESI-APCI) m/z calc'd for C$_{23}$H$_{21}$NO$_4$F$_3$ [M+H]$^+$: 432.1417. found 432.1425.

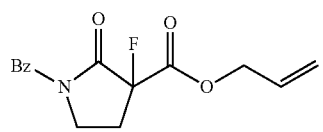

Benzoyl Lactam SI16

Benzoyl Lactam SI16 was prepared by the acylation and alkylation method using N-benzoyl pyrrolidinone as a starting material and using Selectfluor as a fluorinating agent. See Enders, et al., "Asymmetric Electrophilic Substitutions at the α-Position of γ- and δ-Lactams," *Eur. J. Org. Chem.* 4463-4477 (2011); Trost, et al., "Asymmetric syntheses of oxindole and indole spirocyclic alkaloid natural products," *Synthesis* 3003-3025 (2009), the entire contents of both which is incorporated herein by reference. Benzoyl lactam SI16 was isolated by flash chromatography (SiO$_2$, 10 to 20% EtOAc in hexanes) as a colorless oil. R$_f$=0.28 (20% EtOAc in hexanes); $^1$H NMR (500 MHz CDCl$_3$) δ 7.66-7.59 (m, 2H), 7.59-7.50 (m, 1H), 7.46-7.37 (m, 2H), 5.92 (ddt, J=17.2, 10.4, 5.8 Hz, 1H), 5.38 (dq, J=17.2, 1.4 Hz, 1H), 5.32 (dq, J=10.4, 1.1 Hz, 1H), 4.77 (dt, J=5.9, 1.3 Hz, 2H), 4.15 (ddd, J=11.2, 8.8, 4.2 Hz, 1H), 4.01 (dddd, J=11.3, 7.7, 7.0, 2.0 Hz, 1H), 2.80 (dddd, J=14.1, 13.4, 7.8, 4.2 Hz, 1H), 2.53 (dddd, J=23.0, 14.2, 8.8, 7.1 Hz, 1H); $^{13}$C NMR (126 MHz, CDCl$_3$) δ 169.8, 166.0 (d, J=10.2 Hz), 165.8 (d, J=5.5 Hz), 132.9, 132.7, 130.4, 129.0, 128.0, 120.0, 94.4 (d, J=203.6 Hz), 67.2, 42.3 (d, J=2.9 Hz), 29.0 (d, J=21.7 Hz); IR (Neat Film NaCl) 3062, 2987, 2917, 1773, 1690, 1449, 1373, 1290, 1257, 1198, 1161, 1118, 1076, 983, 942, 859, 796, 731 cm$^{-1}$; HRMS (MM: ESI-APCI) m/z calc'd for C$_{16}$H$_{19}$NO$_5$F [M+MeOH+ H]$^+$: 324.1242. found 324.1244.

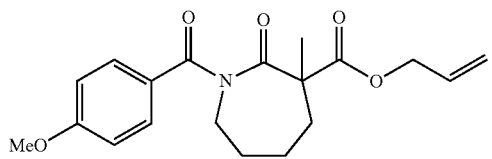

4-Methoxybenzoyl Lactam SI17

4-Methoxy benzoyl lactam SI17 was prepared by a combination of known methods and the diallyl malonate method. See Badillo, et al., "Enantioselective synthesis of oxindoles and spirooxindoles with applications in drug discovery," *Curr. Opin. Drug Disc. Dev.* 13, 758-776 (2010), the entire content of which is incorporated herein by reference. Benzoyl lactam SI17 was isolated by flash chromatography (SiO$_2$, 15 to 25% Et$_2$O in hexanes) as a colorless oil. R$_f$=0.38 (35% Et$_2$O in hexanes); $^1$H NMR (500 MHz, CDCl$_3$) δ 7.79-7.68 (m, 2H), 6.94-6.80 (m, 2H), 5.99 (ddt, J=17.1, 10.4, 6.1 Hz, 1H), 5.43 (dq, J=17.2, 1.4 Hz, 1H), 5.34 (dq, J=10.4, 1.1 Hz, 1H), 4.76 (dt, J=6.1, 1.2 Hz, 2H), 4.28-4.16 (m, 1H), 3.84 (s, 3H), 3.15 (ddd, J=15.6, 11.1, 1.2 Hz, 1H), 2.28-2.17 (m, 1H), 2.01-1.87 (m, 2H), 1.87-1.76 (m, 1H), 1.63 (ddd, J=14.8, 11.8, 3.7 Hz, 2H), 1.48 (s, 3H); $^{13}$C NMR (126 MHz, CDCl$_3$) δ 175.1, 174.6, 172.8, 162.6, 131.3, 130.7, 128.2, 119.9, 113.5, 66.2, 55.3, 54.9, 44.6, 34.3, 28.1, 26.9, 24.9; IR (Neat Film NaCl) 2939, 1679, 1604, 1512, 1456, 1281, 1256, 1169, 1139, 1054, 961 cm$^{-1}$; HRMS (MM: ESI-APCI) m/z calc'd for C$_{19}$H$_{24}$NO$_5$ [M+H]$^+$: 346.1649. found 346.1642.

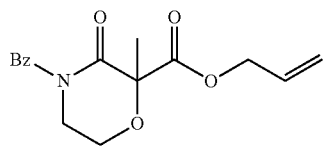

Benzoyl Lactam SI18

Benzoyl lactam SI8 was prepared by the acylation and alkylation method using 3-morpholinone as a starting material and methyl iodide as an alkylating reagent. See Zhou, et al., "Catalytic asymmetric synthesis of oxindoles bearing a tetrasubstituted stereocenter at the C-3 position," *Adv. Synth. Catal.* 1381-1407 (2010), the entire content of which is incorporated herein by reference. Benzoyl lactam SI18 was isolated by flash chromatography (SiO$_2$, 5 to 15% EtOAc in hexanes) as a colorless oil. R$_f$=0.40 (20% EtOAc in hexanes); $^1$H NMR (500 MHz, CDCl$_3$) δ 7.70-7.61 (m, 2H), 7.56-7.44 (m, 1H), 7.46-7.33 (m, 2H), 5.98 (ddt, J=17.1, 10.4, 5.9 Hz, 1H), 5.41 (dq, J=17.2, 1.4 Hz, 1H), 5.34 (dq, J=10.4, 1.1 Hz, 1H), 4.76 (dt, J=6.0, 1.3 Hz, 2H), 4.24 (ddd, J=12.4, 10.1, 3.2 Hz, 1H), 4.12 (ddd, J=12.4, 4.1, 3.3 Hz, 1H), 4.02 (ddd, J=13.2, 10.1, 4.1 Hz, 1H), 3.91 (dt, J=13.2, 3.3 Hz, 1H), 1.68 (s, 3H); $^{13}$C NMR (126 MHz, CDCl$_3$) δ 173.0, 169.0 (2C), 134.9, 132.2, 131.0, 128.3, 128.1, 119.8, 81.5, 66.8, 61.6, 45.3, 22.2; IR (Neat Film NaCl) 2943, 2892, 1749, 1689, 1149, 1375, 1311, 1281, 1246, 1124, 1080, 938, 727 cm$^{-1}$; HRMS (MM: ESI-APCI) m/z calc'd for C$_{16}$H$_{18}$NO$_5$ [M+H]$^+$: 304.1179. found 304.1171.

Benzoyl Lactam SI19

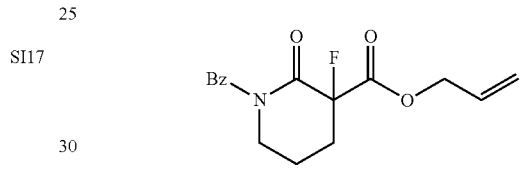

Benzoyl lactam SI19 was prepared by the acylation and alkylation method using Selectfluor as a fluorinating agent. See Amat, et al., "Enantioselective Synthesis of 3,3-Disubstituted Piperidine Derivatives by Enolate Dialkylation of Phenylglycinol-derived Oxazolopiperidone Lactams," *J. Org. Chem.* 72, 4431-4439 (2007), the entire content of which is incorporated herein by reference. Benzoyl lactam SI19 was isolated by flash chromatography (SiO$_2$, 20 to 35% Et$_2$O in hexanes) as a colorless oil. R$_f$=0.57 (35% Et$_2$O in hexanes developed three times); $^1$H NMR (500 MHz, CDCl$_3$) δ 7.69-7.61 (m, 2H), 7.53-7.45 (m, 1H), 7.42-7.34 (m, 2H), 5.94 (ddt, J=17.2, 10.4, 5.9 Hz, 1H), 5.39 (dq, J=17.2, 1.4 Hz, 1H), 5.31 (dq, J=10.4, 1.1 Hz, 1H), 4.76 (dt, J=6.0, 1.3 Hz, 2H), 3.98 (dddd, J=12.9, 6.0, 4.7, 1.1 Hz, 1H), 3.80 (dddd, J=14.8, 8.8, 4.4, 1.7 Hz, 1H), 2.62-2.45 (m, 1H), 2.45-2.30 (m, 1H), 2.25-2.05 (m, 2H); $^{13}$C NMR (126 MHz, CDCl$_3$) δ 173.8, 166.7 (d, J=26.0 Hz), 166.3 (d, J=23.5 Hz), 134.3, 132.3, 130.6, 128.3, 128.2, 119.9, 92.4 (d, J=194.8 Hz), 67.1, 46.2, 31.9 (d, J=22.4 Hz), 18.6 (d, J=4.0 Hz); IR (Neat Film NaCl) 3064, 2956, 1768, 1711, 1691, 1450, 1396, 1304, 1271, 1190, 1137, 1102, 994, 944, 912, 726, 694, 658 cm$^{-1}$; HRMS (MM: ESI-APCI) m/z calc'd for C$_{16}$H$_{17}$NO$_4$F [M+H]$^+$: 306.1136. found 306.1131.

Benzoyl Glutarimide SI20

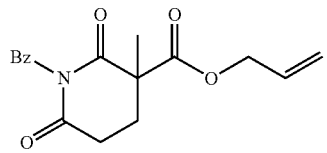

Benzoyl glutarimide SI20 was prepared from glutarimide by a combination of known methods and diallyl malonate method. See Badillo, et al., "Enantioselective synthesis of oxindoles and spirooxindoles with applications in drug discovery," *Curr. Opin. Drug Disc. Dev.* 13, 758-776 (2010), the entire content of which is incorporated herein by reference. Benzoyl glutarimide SI20 (32 mg, 72% yield) was isolated as a colorless oil by flash chromatography (SiO$_2$, 17 to 25% EtOAc in hexanes). R$_f$=0.18 (25% EtOAc in hexanes); $^1$H NMR (500 MHz, CDCl$_3$) δ 7.99 (d, J=8.22 Hz, 2H), 7.62 (t, J=7.46 Hz, 1H), 7.46 (dd, J=8.22, 7.46 Hz, 2H), 5.93 (ddt, J=17.2, 10.4, 6.0 Hz, 1H), 5.39 (dq, J=17.2, 1.20 Hz, 1H), 5.32 (dq, J=10.4, 1.20 Hz, 1H), 4.75 (ddt, J=12.9, 6.0, 1.20 Hz, 1H), 4.71 (ddt, J=12.9, 6.0, 1.20 Hz, 1H), 2.81-2.70 (m, 2H), 2.40 (ddd, J=14.2, 5.13, 3.56 Hz, 1H), 2.10 (ddd, J=14.2, 11.7, 6.36 Hz, 1H), 1.59 (s, 3H); $^{13}$C NMR (126 MHz, CDCl$_3$) δ 171.1, 170.8, 170.7, 170.4, 134.9, 131.6, 130.8, 130.3, 129.0, 120.0, 66.9, 51.0, 30.0, 29.1, 20.8; IR (Neat Film NaCl) 3070, 2943, 2878, 1755, 1716, 1689, 1450, 1240, 1179, 975, 781 cm$^{-1}$; HRMS (MM: ESI-APCI) m/z calc'd for C$_{17}$H$_{18}$NO$_5$ [M+H]$^+$: 316.1179. found 316.1192.

Benzoyl Glutarimide SI21

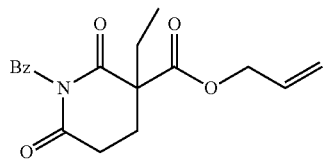

SI21

Benzoyl glutarimide SI121 was prepared from glutarimide by a combination of known methods and the diallyl malonate method. See Badillo, et al., "Enantioselective synthesis of oxindoles and spirooxindoles with applications in drug discovery," *Curr. Opin. Drug Disc. Dev.* 13, 758-776 (2010), the entire content of which is incorporated herein by reference. Benzoyl glutarimide SI21 (67 mg, 85% yield) was isolated as a colorless oil by flash chromatography (SiO$_2$, 17 to 25% EtOAc in hexanes). R$_f$=0.24 (25% EtOAc in hexanes); $^1$H NMR (500 MHz, CDCl$_3$) δ 7.95 (d, J=8.28 Hz, 2H), 7.62 (t, J=7.46 Hz, 1H), 7.46 (dd, J=8.28, 7.46 Hz, 2H), 5.93 (ddt, J=17.0, 10.4, 6.0 Hz, 1H), 5.39 (dq, J=17.0, 1.2 Hz, 1H), 5.32 (dq, J=10.4, 1.2 Hz, 1H), 4.77 (ddt, J=12.9, 6.0, 1.2 Hz, 1H), 4.74 (ddt, J=12.9, 6.0, 1.2 Hz, 1H), 2.84-2.72 (m, 2H), 2.34 (ddd, J=14.1, 5.2, 3.28 Hz, 1H), 2.19 (ddd, J=14.1, 12.2, 5.88 Hz, 1H), 2.15-2.02 (m, 2H), 1.01 (t, J=7.44 Hz, 3H); $^{13}$C NMR (126 MHz, CDCl$_3$) δ 171.1, 170.4, 170.2, 170.1, 134.9, 131.6, 130.8, 130.3, 129.0, 120.0, 66.8, 55.1, 29.9, 27.6, 25.6, 8.9; IR (Neat Film NaCl) 3068, 2975, 2884, 1755, 1716, 1694, 1450, 1270, 1180, 950, 779 cm$^{-1}$; HRMS (MM: ESI-APCI) m/z calc'd for C$_{18}$H$_{20}$NO$_5$ [M+H]$^+$: 330.1336. found 330.1334.

Acetyl Lactam SI22

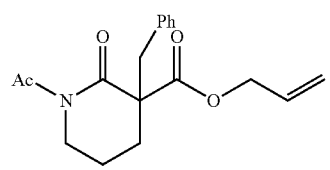

SI22

Acetyl lactam SI22 was prepared the diallyl malonate method using diallyl 2-benzylmalonate as a starting material and acetic anhydride as an acetylating reagent. Acetyl lactam SI22 was isolated by flash chromatography (SiO$_2$, 5 to 20% EtOAc in hexanes) as a colorless oil. R$_f$=0.46 (20% EtOAc in hexanes); $^1$H NMR (500 MHz, CDCl$_3$) δ 7.30-7.20 (m, 3H), 7.20-7.14 (m, 2H), 5.88 (ddt, J=17.2, 10.4, 5.8 Hz, 1H), 5.33 (dq, J=17.2, 1.5 Hz, 1H), 5.27 (dq, J=10.4, 1.2 Hz, 1H), 4.65 (dq, J=5.8, 1.4 Hz, 2H), 3.73-3.62 (m, 1H), 3.53 (d, J=13.6 Hz, 1H), 3.35 (ddd, J=13.8, 9.1, 4.8 Hz, 1H), 3.16 (d, J=13.6 Hz, 1H), 2.52 (s, 3H), 2.29-2.19 (m, 1H), 1.89-1.71 (m, 2H), 1.70-1.56 (m, 1H); $^{13}$C NMR (126 MHz, CDCl$_3$) δ 173.9, 172.3, 171.6, 135.8, 131.2, 130.6, 128.3, 127.1, 119.3, 66.4, 58.1, 43.6, 41.2, 29.4, 27.2, 19.8; IR (Neat Film NaCl) 3063, 3029, 2942, 1733, 1699, 1496, 1455, 1368, 1296, 1234, 1177, 1116, 1034, 992, 975, 934, 746, 703 cm$^{-1}$; HRMS (MM: ESI-APCI) m/z calc'd for C$_{18}$H$_{22}$NO$_4$ [M+H]$^+$: 316.1543. found 316.1541.

Phenyl Carbamate Lactam SI23

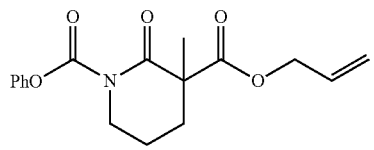

SI23

Phenyl carbamate lactam SI23 was prepared in a manner analogous to the tosyl lactam of Compound 1a using lactam SI4 and phenyl chloroformate. Phenyl carbamate lactam SI23 was isolated by flash chromatography (SiO$_2$, 5 to 20% EtOAc in hexanes) as a colorless oil. R$_f$=0.42 (50% EtOAc in hexanes); $^1$H NMR (500 MHz, CDCl$_3$) δ 7.40-7.35 (m, 2H), 7.26-7.21 (m, 1H), 7.20-7.16 (m, 2H), 5.91 (ddt, J=17.2, 10.4, 5.6 Hz, 1H), 5.36 (dq, J=17.2, 1.5 Hz, 1H), 5.26 (dq, J=10.5, 1.3 Hz, 1H), 4.77-4.59 (m, 2H), 3.90 (ddd, J=12.9, 7.6, 5.3 Hz, 1H), 3.85-3.74 (m, 1H), 2.47 (dddd, J=13.8, 6.2, 5.0, 1.0 Hz, 1H), 2.06-1.86 (m, 2H), 1.80 (ddd, J=14.2, 9.3, 5.0 Hz, 1H), 1.56 (s, 3H); $^{13}$C NMR (126 MHz, CDCl$_3$) δ 172.1, 171.2, 153.3, 150.8, 131.3, 129.4, 126.0, 121.4, 118.8, 66.2, 53.4, 46.8, 32.7, 22.7, 20.1; IR (Neat Film NaCl) 2943, 1786, 1732, 1494, 1457, 1297, 1267, 1204, 1161, 1134, 982, 943, 752, 689, 665 cm$^{-1}$; HRMS (MM: ESI-APCI) m/z calc'd for C$_{17}$H$_{20}$NO$_5$ [M+H]$^+$: 318.1336. found 318.1332.

Benzyl Carbamate Lactam SI24

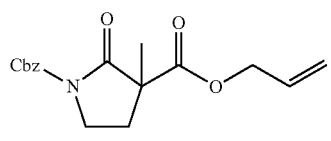

SI24

Benzyl carbamate lactam SI24 was prepared by the acylation and alkylation method using N-benzyloxycarbonylpyrrolidin-2-one as a starting material and methyl iodide as an alkylating reagent. See Ohmatsu, et al., "Chiral 1,2,3-triazoliums as New Cationic Organic Catalysts with Anion-Recognition Ability: Application to Asymmetric Alkylation of Oxindoles," *J. Am. Chem. Soc.* 133, 1307-1309 (2011), the entire content of which is incorporated herein by reference. Cbz lactam SI24 was isolated by flash chromatography (SiO$_2$, 5 to 15% EtOAc in hexanes) as a colorless oil. R$_f$=0.40 (20% EtOAc in hexanes); $^1$H NMR (500 MHz, CDCl$_3$) δ 7.46-7.40 (m, 2H), 7.40-7.28 (m, 3H), 5.87 (ddt, J=17.1, 10.4, 5.6 Hz, 1H), 5.30 (dq, J=17.2, 1.5 Hz, 1H) 5.30 (s, 2H), 5.23 (dq, J=10.5, 1.2 Hz, 1H), 4.69-4.55 (m, 2H), 3.82 (ddq, J=10.7, 8.4, 5.8 Hz, 2H), 2.54 (ddd, J=13.1, 7.4, 4.2 Hz, 1H), 1.93 (dt, J=13.2, 8.3 Hz, 1H), 1.50 (s, 3H); $^{13}$C NMR (126 MHz, CDCl$_3$) δ 171.9, 170.7, 151.4, 135.1, 131.3, 128.6, 128.4, 128.1, 118.8, 68.3, 66.3, 53.3, 43.7, 30.5, 20.2; IR (Neat Film NaCl) 2984, 2939, 1793, 1758, 1725, 1456, 1383, 1300, 1202, 1138, 1009, 983, 774, 739, 698 cm$^{-1}$; HRMS (MM: ESI-APCI) m/z calc'd for C$_{17}$H$_{20}$NO$_5$ [M+H]$^+$: 318.1336. found 318.1136.

4-Phenylbenzoyl Lactam SI25

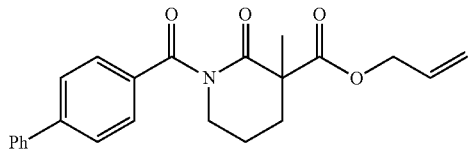

SI25

4-phenylbenzoyl lactam SI25 was prepared the diallyl malonate method using lactam SI4 and 4-phenylbenzoyl chloride. 4-Phenylbenzoyl lactam SI25 was isolated by flash chromatography (SiO$_2$, 5 to 15% EtOAc in hexanes) as an off-white solid. R$_f$=0.27 (20% EtOAc in hexanes); $^1$H NMR (500 MHz, CDCl$_3$) δ 7.84-7.77 (m, 2H), 7.65-7.54 (m, 4H), 7.49-7.40 (m, 2H), 7.40-7.34 (m, 1H), 6.00 (ddt, J=17.2, 10.4, 5.9 Hz, 1H), 5.41 (dq, J=17.2, 1.5 Hz, 1H), 5.34 (dq, J=10.4, 1.2 Hz, 1H), 4.75 (dt, J=5.9, 1.3 Hz, 2H), 3.95-3.84 (m, 1H), 3.81 (ddt, J=12.9, 5.1, 1.4 Hz, 1H), 2.52 (dddd, J=13.8, 5.7, 4.3, 1.4 Hz, 1H), 2.10-1.94 (m, 2H), 1.90-1.76 (m, 1H), 1.52 (s, 3H); $^{13}$C NMR (126 MHz, CDCl$_3$) δ 174.7, 172.9, 172.5, 144.5, 140.3, 134.5, 131.4, 128.8, 128.7, 127.8, 127.3, 126.8, 119.5, 66.5, 52.9, 46.89, 33.8, 22.5, 20.3; IR (Neat Film NaCl) 3030, 2942, 2874, 1733, 1679, 1607, 1486, 1449, 1389, 1278, 1191, 1139, 939, 749, 698 cm$^{-1}$; HRMS (MM: ESI-APCI) m/z calc'd for C$_{23}$H$_{24}$NO$_4$ [M+H]$^+$: 378.1700. found 378.1708.

1-Naphthoyl Lactam SI26

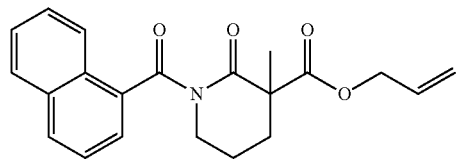

SI26

1-naphthoyl lactam SI26 was prepared by the diallyl malonate method using lactam SI4 and 1-naphthoyl chloride. 1-Naphthoyl lactam SI26 was isolated by flash chromatography (SiO$_2$, 10 to 20% EtOAc in hexanes) as a colorless oil. R$_f$=0.50 (35% EtOAc in hexanes); $^1$H NMR (500 MHz, CDCl$_3$) δ 8.07-8.01 (m, 1H), 7.90 (dd, J=8.2, 1.4 Hz, 1H), 7.88-7.83 (m, 1H), 7.57-7.47 (m, 3H), 7.42 (td, J=7.6, 7.0, 1.2 Hz, 1H), 5.99-5.86 (m, 1H), 5.35 (dq, J=17.3, 1.3 Hz, 1H), 5.30 (dq, J=10.6, 1.0 Hz, 1H), 4.66 (ddt, J=5.4, 4.2, 1.3 Hz, 2H), 4.13-3.91 (m, 2H), 2.49 (ddd, J=13.6, 6.1, 4.5 Hz, 1H), 2.14-1.97 (m, 2H), 1.83 (ddd, J=14.3, 9.9, 4.6 Hz, 1H), 1.42 (s, 3H); $^{13}$C NMR (126 MHz, CDCl$_3$) δ 173.8, 172.4, 172.1, 134.9, 133.6, 131.3, 130.3, 129.8, 128.4, 127.0, 126.1, 124.9, 124.4, 123.9, 119.3, 66.3, 52.9, 45.7, 33.4, 22.4, 20.1; IR (Neat Film NaCl) 3050, 2984, 2942, 1737, 1704, 1682, 1509, 1456, 1387, 1290, 1254, 1194, 1144, 1130, 935, 806, 783 cm$^{-1}$; HRMS (MM: ESI-APCI) in Z calc'd for C$_{21}$H$_{22}$NO$_4$ [M+H]$^+$: 352.1543. found 352.1542.

2-Naphthoyl Lactam SI27

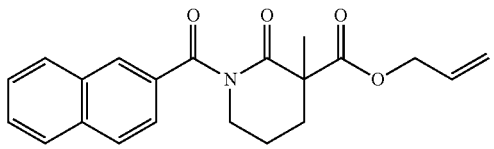

SI27

2-naphthoyl lactam SI27 was prepared by the diallyl malonate method using lactam SI4 and 2-naphthoyl chloride. 2-Naphthoyl lactam SI27 was isolated by flash chromatography (SiO$_2$, 20 to 33% Et$_2$O in hexanes) as a colorless oil. R$_f$=0.25 (35% Et$_2$O in hexanes); $^1$H NMR (500 MHz, CDCl$_3$) δ 8.30 (t, J=1.2 Hz, 1H), 7.90 (dd, J=8.1, 1.4 Hz, 1H), 7.85-7.79 (m, 2H), 7.76 (dd, J=8.6, 1.7 Hz, 1H), 7.54 (ddd, J=8.1, 6.8, 1.4 Hz, 1H), 7.50 (ddd, J=8.1, 6.9, 1.4 Hz, 1H), 6.01 (ddt, J=17.2, 10.4, 5.8 Hz, 1H), 5.42 (dq, J=17.2, 1.4 Hz, 1H), 5.34 (dq, J=10.4, 1.1 Hz, 1H), 4.77 (dt, J=5.9, 1.3 Hz, 2H), 3.93 (ddd, J=12.8, 8.9, 5.3 Hz, 1H), 3.85 (ddt, J=12.9, 5.1, 1.3 Hz, 1H), 2.52 (dddd, J=13.8, 5.6, 4.2, 1.3 Hz, 1H), 2.12-1.93 (m, 2H), 1.84 (ddd, J=13.7, 10.2, 4.7 Hz, 1H), 1.51 (s, 3H); $^{13}$C NMR (126 MHz, CDCl$_3$) δ 174.9, 172.8, 172.5, 134.8, 133.2, 132.5, 131.4, 129.2, 129.0, 127.7 (2C), 127.6, 126.3, 124.4, 119.4, 66.4, 52.9, 46.8, 33.7, 22.4, 20.2; IR (Neat Film NaCl) 3059, 2941, 2873, 1730, 1680, 1456, 1385, 1285, 1234, 1186, 1131, 936, 778, 762 cm$^{-1}$; HRMS (MM: ESI-APCI) m/z calc'd for C$_{21}$H$_{22}$NO$_4$ [M+H]$^+$: 352.1543. found 352.1530.

General Procedure for Preparative Allylic Alkylation Reactions to Form N-Acyl Lactam Derivatives The N-acyl lactam substrates described above were subjected to allylic alkylation reactions to form N-acyl lactam derivative building block compounds. The general procedure for these reactions is described here.

In a nitrogen-filled glovebox, an oven-dried 20 mL vial was charged with Pd$_2$ pmdba$_3$ (27.4 mg, 0.025 mmol, 0.05 equiv) or Pd$_2$ dba$_3$ (22.9 mg, 0.025 mmol, 0.05 equiv), (S)—(CF$_3$)$_3$-t-BuPHOX (37.0 mg, 0.0625 mmol, 0.125 equiv), toluene (15 mL, or 13 mL if the substrate is an oil), and a magnetic stir bar. See Franckevicius, et al., "Asymmetric Decarboxylative Alkylation of Oxindoles," Org. Lett. 13, 4264-4267 (2011), the entire content of which is incorporated herein by reference. The vial was stirred at ambient glovebox temperature (~28° C.) for 30 min and the substrate (0.50 mmol, 1.00 equiv) was added either as a solid or as a solution of an oil dissolved in toluene (2 mL). The vial was sealed and heated to 40° C. When complete consumption of the starting material was observed by colorimetric change (from light green to red-orange) and confirmed by thin layer chromatography on SiO$_2$, the reaction mixtures were removed from the glovebox, concentrated under reduced pressure, and purified by flash chromatography to afford the desired alkylated product.

Characterization Data for the N-acyl Lactam Derivative Building Blocks

The N-acyl lactam Derivatives were isolated as described below and characterized. The characterization data is reported below.

Benzoyl Lactam 3

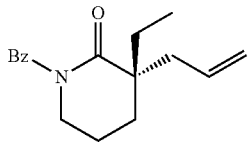

3

See Jakubec, et al., "Cyclic Imine Nitro-Mannich/Lactamization Cascades: A Direct Stereoselective Synthesis of Multicyclic Piperidinone Derivatives," *Org. Lett.* 10, 4267-4270 (2008), the entire content of which is incorporated by reference. Benzoyl lactam 3 was isolated by flash chromatography ($SiO_2$, 15 to 20% $Et_2O$ in hexanes) as a colorless oil. 97.2% yield. $R_f$=0.39 (20% $Et_2O$ in hexanes); $^1$H NMR (500 MHz, $CDCl_3$) δ 7.53-7.49 (m, 2H), 7.48-7.43 (m, 1H), 7.41-7.34 (m, 2H), 5.74 (dddd, J=16.7, 10.4, 7.6, 7.0 Hz, 1H), 5.19-5.02 (m, 2H), 3.84-3.70 (m, 2H), 2.51 (ddt, J=13.8, 7.0, 1.3 Hz, 1H), 2.28 (ddt, J=13.8, 7.6, 1.2 Hz, 1H), 2.06-1.91 (m, 2H), 1.91-1.74 (m, 3H), 1.74-1.63 (m, 1H), 0.91 (t, J=7.4 Hz, 3H); $^{13}$C NMR (126 MHz, $CDCl_3$) δ 178.0, 175.6, 136.7, 133.6, 131.2, 128.1, 127.4, 118.6, 47.4, 46.9, 41.3, 30.3 (2C), 19.6, 8.3; IR (Neat Film NaCl) 3072, 2970, 2941, 2880, 1678, 1448, 1384, 1283, 1147, 916, 725, 694 $cm^{-1}$; HRMS (MM: ESI-APCI) m/z calc'd for $C_{17}H_{22}NO_2$ [M+H]$^+$: 272.1645. found 272.1649; $[\alpha]_D^{25}$ −28.6° (c 1.15, $CHCl_3$, 99% ee).

Benzoyl Lactam 4

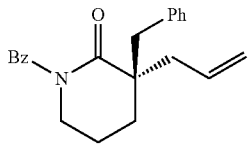

4

See Jakubec, et al., "Cyclic Imine Nitro-Mannich/Lactamization Cascades: A Direct Stereoselective Synthesis of Multicyclic Piperidinone Derivatives," *Org. Lett.* 10, 4267-4270 (2008), the entire content of which is incorporated by reference. Benzoyl lactam 4 was isolated by flash chromatography ($SiO_2$, 10% $Et_2O$ in hexanes) as a white solid. 84.8% yield. $R_f$=0.48 (35% $Et_2O$ in hexanes); $^1$H NMR (500 MHz, $CDCl_3$) δ 7.54 (dd, J=8.1, 1.4 Hz, 2H), 7.52-7.46 (m, 1H), 7.43-7.37 (m, 2H), 7.32-7.22 (m, 3H), 7.18-7.11 (m, 2H), 5.80 (dddd, J=16.8, 10.1, 7.6, 6.8 Hz, 1H), 5.21-5.06 (m, 2H), 3.70 (ddd, J=12.2, 7.0, 4.8 Hz, 1H), 3.63 (ddd, J=12.5, 7.7, 4.4 Hz, 1H), 3.34 (d, J=13.4 Hz, 1H), 2.73-2.64 (m, 1H), 2.68 (d, J=13.3 Hz, 1H), 2.25 (ddt, J=13.8, 7.7, 1.1 Hz, 1H), 2.03-1.91 (m, 1H), 1.91-1.83 (m, 1H), 1.81 (dd, J=6.7, 5.3 Hz, 2H); $^{13}$C NMR (126 MHz, $CDCl_3$) δ 177.4, 175.5, 136.9, 136.6, 133.2, 131.4, 130.8, 128.2, 128.1, 127.6, 126.7, 119.3, 48.8, 46.8, 43.0, 42.9, 28.9, 19.6; IR (Neat Film NaCl) 3061, 3028, 2942, 1679, 1449, 1286, 1149, 919, 724, 704, 695 $cm^{-1}$; HRMS (MM: ESI-APCI) m/z calc'd for $C_{22}H_{24}NO_2$ [M+H]$^+$: 334.1802. found 334.1800; $[\alpha]_D^{25}$ +48.1° (c 0.825, $CHCl_3$, 99% ee).

Benzoyl Lactam 5

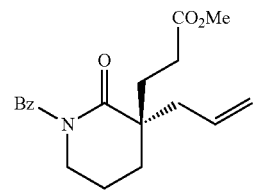

5

Benzoyl lactam 5 was isolated by flash chromatography ($SiO_2$, 25% $Et_2O$ in hexanes) as a light yellow oil. 91.8% yield. $R_f$=0.39 (35% $Et_2O$ in hexanes); $^1$H NMR (500 MHz $CDCl_3$) δ 7.53-7.49 (m, 2H), 7.49-7.44 (m, 1H), 7.41-7.31 (m, 2H), 5.72 (ddt, J=17.4, 10.3, 7.3 Hz, 1H), 5.23-5.05 (m, 2H), 3.78 (t, J=6.0 Hz, 2H), 3.67 (s, 3H), 2.58-2.47 (m, 1H), 2.42-2.24 (m, 3H), 2.08-1.97 (m, 4H), 1.93 (ddd, J=14.0, 7.8, 4.6 Hz, 1H), 1.78 (ddd, J=13.9, 7.1, 4.9 Hz, 1H); $^{13}$C NMR (126 MHz, $CDCl_3$) δ 177.4, 175.5, 173.7, 136.5, 132.6, 131.4, 128.2, 127.4, 119.4, 51.7, 47.0, 46.6, 41.2, 32.2, 31.2, 29.0, 19.4; IR (Neat Film NaCl) 3073, 2950, 2874, 1736, 1679, 1448, 1281, 1150, 920, 727, 696, 665 $cm^{-1}$; HRMS (MM: ESI-APCI) m/z calc'd for $C_{19}H_{24}NO_4$ [M+H]$^+$: 330.1700. found 330.1704; $[\alpha]_D^{25}$ +14.0° (c 0.72, $CHCl_3$, 99% ee).

Benzoyl Lactam 6

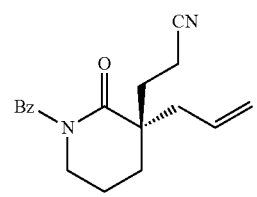

6

Benzoyl lactam 6 was isolated by flash chromatography ($SiO_2$, 15 to 25% EtOAc in hexanes) as a colorless oil. 88.2% yield. $R_f$=0.43 (35% EtOAc in hexanes); $^1$H NMR (500 MHz, $CDCl_3$) δ 7.52-7.47 (m, 3H), 7.41 (ddt, J=8.7, 6.6, 1.0 Hz, 2H), 5.71 (ddt, J=17.4, 10.1, 7.3 Hz, 1H), 5.28-5.15 (m, 2H), 3.88-3.79 (m, 1H), 3.76 (ddd, J=12.9, 8.7, 4.2 Hz, 1H), 2.57 (ddt, J=14.1, 7.3, 1.2 Hz, 1H), 2.44-2.29 (m, 3H), 2.13-2.04 (m, 2H), 2.03-1.89 (m, 3H), 1.87-1.78 (m, 1H); $^{13}$C NMR (126 MHz, $CDCl_3$) δ 176.8, 175.2, 136.2, 131.7, 131.5, 128.3, 127.3, 120.3, 119.5, 47.0, 46.5, 41.1, 32.7, 30.8, 19.2, 12.5; IR (Neat Film NaCl) 3074, 2945, 2876, 1678, 1448, 1389, 1282, 1151, 922, 727, 696 $cm^{-1}$; HRMS (MM: ESI-APCI) m/z calc'd for $C_8H_{21}N_2O_2$ [M+H]$^+$: 297.1598. found 297.1603; $[\alpha]_D^{25}$ +46.9° (c 0.83, $CHCl_3$, 99% ee).

Benzoyl Lactam 7

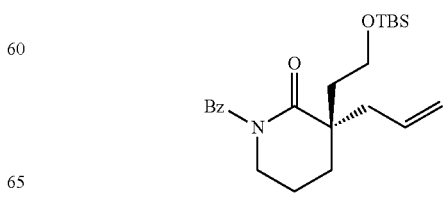

7

Benzoyl lactam 7 was isolated by flash chromatography (SiO$_2$, 5 to 15% Et$_2$O in hexanes) as a colorless oil. 85.4% yield. R$_f$=0.32 (10% Et$_2$O in hexanes); $^1$H NMR (500 MHz, CDCl$_3$) δ 7.54-7.48 (m, 2H), 7.48-7.42 (m, 1H), 7.41-7.33 (m, 2H), 5.76 (ddt, J=17.3, 10.2, 7.3 Hz, 1H), 5.18-5.06 (m, 2H), 3.81-3.75 (m, 2H), 3.75-3.64 (m, 2H), 2.55 (ddt, J=13.8, 7.1, 1.2 Hz, 1H), 2.33 (ddt, J=13.8, 7.5, 1.1 Hz, 1H), 2.10-1.94 (m, 4H), 1.94-1.85 (m, 1H), 1.81 (ddd, J=13.9, 7.3, 5.6 Hz, 1H), 0.88 (s, 9H), 0.04 (s, 6H); $^{13}$C NMR (126 MHz, CDCl$_3$) δ 177.6, 175.5, 136.8, 133.4, 131.2, 128.1, 127.4, 118.9, 59.2, 46.9, 46.3, 42.2, 39.7, 30.8, 25.9, 19.6, 18.2, −5.4; IR (Neat Film NaCl) 2953, 2928, 2884, 2856, 1681, 1280, 1257, 1151, 1093, 836, 776, 725, 694 cm$^{-1}$; HRMS (MM: ESI-APCI) m/z calc'd for C$_{23}$H$_{36}$NO$_3$Si [M+H]$^+$: 402.2459. found 402.2467; [α]$_D^{25}$ −3.71° (c 1.40, CHCl$_3$, 96% ee).

Benzoyl Lactam 8

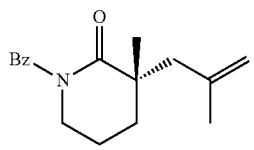

8

Benzoyl lactam 8 was isolated by flash chromatography (SiO$_2$, 5 to 9% EtOAc in hexanes) as a colorless oil. 78.0% yield. R$_f$=0.54 (25% EtOAc in hexanes); $^1$H NMR (500 MHz, CDCl$_3$) δ 7.54-7.50 (m, 2H), 7.48-7.43 (m, 1H), 7.41-7.35 (m, 2H), 4.89 (t, J=1.8 Hz, 1H), 4.70 (dt, J=2.1, 1.0 Hz, 1H), 3.94-3.84 (m, 1H), 3.74-3.63 (m, 1H), 2.75 (dd, J=13.8, 1.3 Hz, 1H), 2.13 (dd, J=13.8, 0.8 Hz, 1H), 2.08-1.94 (m, 3H), 1.69 (s, 3H), 1.68-1.61 (m, 1H), 1.37 (s, 3H); $^{13}$C NMR (126 MHz, CDCl$_3$) δ 178.8, 175.5, 141.9, 136.5, 131.3, 128.1, 127.4, 115.5, 47.2, 46.2, 44.0, 32.9, 26.9, 24.7, 19.8; IR (Neat Film NaCl) 3070, 2940, 1678, 1448, 1274, 1144, 726 cm$^{-1}$; HRMS (MM: ESI-APCI) m/z calc'd for C$_{17}$H$_{22}$NO$_2$ [M+H]$^+$: 272.1645. found 272.1655; [α]$_D^{25}$ −105.6° (c 0.99, CHCl$_3$, 97% ee).

Benzoyl Lactam 9

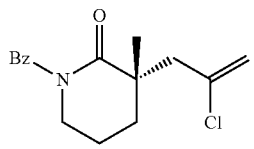

9

Benzoyl lactam 9 was isolated by flash chromatography (SiO$_2$, 8 to 10% Et$_2$O in hexanes) as a colorless oil. 60.3% yield. R$_f$=0.39 (25% EtOAc in hexanes); $^1$H NMR (500 MHz, CDCl$_3$) δ 7.55-7.49 (m, 2H), 7.49-7.43 (m, 1H), 7.42-7.34 (m, 2H), 5.32 (d, J=1.7 Hz, 1H), 5.18 (s, 1H), 3.92 (ddt, J=12.7, 4.8, 1.7 Hz, 1H), 3.75-3.66 (m, 1H), 3.04 (dd, J=14.5, 1.0 Hz, 1H), 2.50 (d, J=14.5 Hz, 1H), 2.16 (ddd, J=13.4, 10.2, 4.4 Hz, 1H), 2.12-1.98 (m, 2H), 1.86-1.77 (m, 1H), 1.43 (s, 3H); $^{13}$C NMR (126 MHz, CDCl$_3$) δ 177.9, 175.3, 138.3, 136.4, 131.4, 128.1, 127.4, 117.1, 47.0 (2C), 44.2, 32.8, 26.3, 19.7; IR (Neat Film NaCl) 2944, 2872, 1679, 1448, 1386, 1277, 1151, 894, 726 cm$^{-1}$; HRMS (MM: ESI-APCI) m/z calc'd for C$_{16}$H$_{19}$NO$_2$Cl [M+H]$^+$: 292.1099. found 292.1102; [α]$_D^{25}$ −91.4° (c 0.94, CHCl$_3$ 95% ee).

Benzoyl Lactam 10

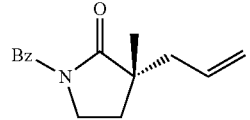

10

Benzoyl lactam 10 was isolated by flash chromatography (SiO$_2$, 5 to 10% Et$_2$O in hexanes) as a colorless oil. 90.3% yield. R$_f$=0.35 (35% Et$_2$O in hexanes); $^1$H NMR (500 MHz, CDCl$_3$) δ 7.58-7.54 (m, 2H), 7.53-7.48 (m, 1H), 7.43-7.38 (m, 2H), 5.78 (dddd, J=17.1, 10.2, 7.8, 7.0 Hz, 1H), 5.22-5.09 (m, 2H), 3.87 (dd, J=7.7, 6.7 Hz, 2H), 2.36 (dd, J=13.8, 7.0 Hz, 1H), 2.24 (dd, J=13.7, 7.8 Hz, 1H), 2.15 (dt, J=12.9, 7.6 Hz, 1H), 1.85 (dt, J=13.1, 6.7 Hz, 1H), 1.22 (s, 3H); $^{13}$C NMR (126 MHz, CDCl$_3$) δ 178.6, 170.8, 134.4, 133.0, 131.8, 128.8, 127.7, 119.3, 46.2, 42.8, 41.8, 29.3, 22.8; IR (Neat Film NaCl) 3075, 2974, 2902, 1742, 1674, 1448, 1377, 1357, 1306, 1243, 1156, 921, 860, 731, 694, 656 cm$^{-1}$; HRMS (MM: ESI-APCI) m/z calc'd for C$_{15}$H$_{18}$NO$_2$ [M+H]$^+$: 244.1332. found 244.1336; [α]$_D^{25}$ −31.6° (c 1.04, CHCl$_3$, 98% ee).

Benzoyl Lactam 11

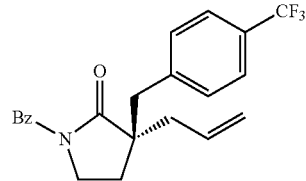

11

Benzoyl lactam 11 was isolated by flash chromatography (SiO$_2$, 10 to 20% Et$_2$O in hexanes) as a colorless oil. 89.3% yield. R$_f$=0.24 (20% Et$_2$O in hexanes); $^1$H NMR (500 MHz, CDCl$_3$) δ 7.60-7.56 (m, 2H), 7.56-7.51 (m, 1H), 7.49-7.45 (m, 2H), 7.42 (ddt, J=7.8, 6.7, 1.0 Hz, 2H), 7.31 (d, J=7.7 Hz, 2H), 5.83 (dddd, J=17.1, 10.1, 7.8, 6.9 Hz, 1H), 5.28-5.10 (m, 2H), 3.70 (dt, J=11.4, 7.5 Hz, 1H), 3.39 (dt, J=11.4, 6.9 Hz, 1H), 3.10 (d, J=13.4 Hz, 1H), 2.76 (d, J=13.5 Hz, 1H), 2.48 (dd, J=13.8, 7.0 Hz, 1H), 2.32 (dd, J=13.8, 7.8 Hz, 1H), 2.05 (t, J=7.3 Hz, 2H); $^{13}$C NMR (126 MHz, CDCl$_3$) δ 177.1, 170.5, 140.9, 134.2, 132.3, 131.9, 130.7, 129.4 (q, J$_{C-F}$=32.5 Hz), 128.7, 127.7, 125.3 (q, J$_{C-F}$=3.7 Hz), 124.1 (q, J$_{C-F}$=272.2 Hz), 120.1, 51.3, 43.0, 41.9 (2C), 25.2; IR (Neat Film NaCl) 3080, 2977, 2913, 1738, 1677, 1325, 1294, 1244, 1164, 1121, 1067, 859, 728, 701, 665 cm$^{-1}$; HRMS (FAB) m/z calc'd for C$_{22}$H$_{21}$NO$_2$F$_3$ [M+H]$^+$: 388.1524. found 388.1525; [α]$_D^{25}$ +78.3° (c 1.90, CHCl$_3$, 93% ee).

Benzoyl Lactam 12

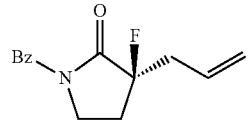

12

Benzoyl lactam 12 was isolated by flash chromatography (SiO$_2$, 10 to 20% Et$_2$O in hexanes) as a white solid. 85.7% yield. R$_f$=0.35 (35% Et$_2$O in hexanes); $^1$H NMR (500 MHz, CDCl$_3$) δ 7.63-7.58 (m, 2H), 7.58-7.52 (m, 1H), 7.49-7.40 (m, 2H), 5.87-5.73 (m, 1H), 5.32-5.20 (m, 2H), 4.00 (ddd, J=11.5, 7.7, 6.5 Hz, 1H), 3.90-3.80 (m, 1H), 2.81-2.70 (m, 1H), 2.62-2.48 (m, 1H), 2.46-2.27 (m, 2H); $^{13}$C NMR (126 MHz, CDCl$_3$) δ 170.3, 169.7 (d, J$_{C-F}$=23.1 Hz), 133.4, 132.4, 129.7 (d, J$_{C-F}$=7.1 Hz), 129.0, 127.9, 121.0, 97.0 (d, J$_{C-F}$=185.4 Hz), 42.0 (d, J$_{C-F}$=2.3 Hz), 38.4 (d, J$_{C-F}$=25.2 Hz), 28.5 (d, J$_{C-F}$=22.6 Hz); IR (Neat Film NaCl) 3076, 1760, 1676, 1365, 1314, 1253, 1132, 1058, 1008, 980, 920, 863, 791, 729 cm$^{-1}$; HRMS (MM: ESI-APCI) m/z calc'd for C$_{14}$H$_{15}$NO$_2$F [M+H]$^+$: 248.1081. found 248.1092; [α]$_D^{25}$ −120.5° (c 1.11, CHCl$_3$, 98% ee).

4-Methoxybenzoyl Lactam 13:

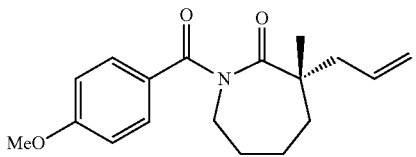

13

The reaction was performed in MTBE at 40° C. 4-Methoxybenzoyl lactam 13 was isolated by flash chromatography (SiO$_2$, 8% Et$_2$O in hexanes) as a colorless oil. 83.2% yield. R$_f$=0.48 (25% EtOAc in hexanes); $^1$H NMR (500 MHz, CDCl$_3$) δ 7.56-7.48 (m, 2H), 6.91-6.82 (m, 2H), 5.86-5.66 (m, 1H), 5.18-5.02 (m, 2H), 4.03 (ddd, J=15.0, 8.0, 2.4 Hz, 1H), 3.88 (ddd, J=15.1, 8.5, 2.1 Hz, 1H), 3.83 (s, 3H), 2.50 (ddt, J=13.6, 7.0, 1.2 Hz, 1H), 2.35 (ddt, J=13.7, 7.6, 1.1 Hz, 1H), 1.92-1.77 (m, 4H), 1.77-1.62 (m, 2H), 1.31 (s, 3H); $^{13}$C NMR (126 MHz, CDCl$_3$) δ 182.3, 174.7, 162.2, 133.9, 130.0, 128.9, 118.6, 113.5, 55.4, 47.7, 44.7, 43.0, 35.1, 28.2, 25.0, 23.4; IR (Neat Film NaCl) 3074, 2932, 1673, 1605, 1511, 1279, 1255, 1168, 1112, 1025, 837 cm$^{-1}$; HRMS (MM: ESI-APCI) m/z calc'd for C$_{18}$H$_{24}$NO$_3$ [M+H]$^+$: 302.1751. found 302.1744; [α]$_D^{25}$ −34.7° (c 0.75, CHCl$_3$, 93% ee).

Benzoyl Lactam 14

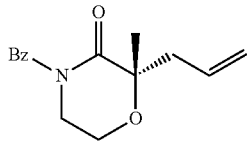

14

Benzoyl lactam 14 was isolated by flash chromatography (SiO$_2$, 10 to 20% Et$_2$O in hexanes) as a colorless oil. 91.4% yield. R$_f$=0.36 (35% Et$_2$O in hexanes); $^1$H NMR (500 MHz, CDCl$_3$) δ 7.55-7.52 (m, 2H), 7.52-7.47 (m, 1H), 7.42-7.37 (m, 2H), 5.90 (ddt, J=17.3, 10.3, 7.2 Hz, 1H), 5.26-5.10 (m, 2H), 4.12-3.95 (m, 3H), 3.94-3.81 (m, 1H), 2.71 (ddt, J=14.1, 7.3, 1.2 Hz, 1H), 2.47 (ddt, J=14.1, 7.0, 1.3 Hz, 1H), 1.48 (s, 3H); $^{13}$C NMR (126 MHz, CDCl$_3$) δ 174.3, 173.1, 135.7, 132.1, 131.7, 128.1, 127.7, 119.3, 80.3, 59.4, 45.7, 43.1, 23.3; IR (Neat Film NaCl) 3075, 2978, 2894, 1685, 1448, 1373, 1283, 1227, 1111, 1092, 921, 726, 694 cm$^{-1}$; HRMS (FAB) m/z calc'd for C$_{15}$H$_{18}$NO$_3$ [M+H]$^+$: 260.1287. found 260.1277; [α]$_D^{25}$ −72.1° (c 0.97, CHCl$_3$, 99% ee).

Benzoyl Lactam 15

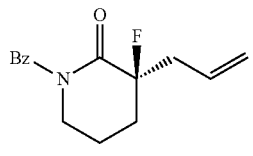

15

Benzoyl lactam 15 was isolated by flash chromatography (SiO$_2$, 5 to 10% EtOAc in hexanes) as a colorless oil. 88.8% yield. R$_f$=0.35 (35% Et$_2$O in hexanes); $^1$H NMR (500 MHz, CDCl$_3$) δ 7.62-7.57 (m, 2H), 7.53-7.47 (m, 1H), 7.44-7.37 (m, 2H), 5.87-5.70 (m, 1H), 5.28-5.15 (m, 2H), 3.91 (dddd, J=12.8, 6.0, 4.7, 1.4 Hz, 1H), 3.74 (dddd, J=13.6, 9.2, 4.5, 2.4 Hz, 1H), 2.86-2.60 (m, 2H), 2.33-2.14 (m, 2H), 2.13-1.89 (m, 2H); $^{13}$C NMR (126 MHz, CDCl$_3$) δ 174.5, 170.8 (d, J$_{C-F}$=23.5 Hz), 135.0, 132.0, 130.6 (d, J$_{C-F}$=6.5 Hz), 128.3, 128.0, 120.4, 93.9 (d, J$_{C-F}$=179.3 Hz), 46.4, 40.0 (d, J$_{C-F}$=23.6 Hz), 32.1 (d, J$_{C-F}$=22.5 Hz), 19.1 (d, J$_{C-F}$=4.6 Hz); IR (Neat Film NaCl) 3078, 2956, 1715, 1687, 1478, 1449, 1435, 1390, 1288, 1273, 1175, 1152, 1000, 930, 725, 694, 662 cm$^{-1}$; HRMS (MM: ESI-APCI) m/z calc'd for C$_{15}$H$_{16}$NO$_2$F [M+H]$^+$: 262.1238. found 262.1244; [α]$_D^{25}$ −120.6° (c 1.09, CHCl$_3$, 99% ee).

Benzoyl Glutarimide 16

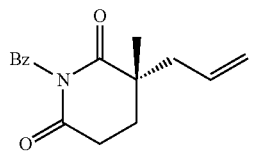

16

Benzoyl glutarimide 16 was isolated by flash chromatography (SiO$_2$, 17 to 25% EtOAc in hexanes) as a colorless oil. 81% yield. R$_f$=0.21 (25% EtOAc in hexanes); $^1$H NMR (500 MHz, CDCl$_3$) δ 7.83 (d, J=8.29 Hz, 2H), 7.63 (t, J=7.45 Hz, 1H), 7.48 (dd, J=8.29, 7.45 Hz, 2H), 5.77 (dddd, J=17.4, 10.2, 7.4, 7.0 Hz, 1H), 5.22-5.16 (m, 2H), 2.87-2.77 (m, 2H), 2.59 (ddt, J=13.8, 7.0, 1.0 Hz, 1H), 2.40 (ddt, J=13.8, 7.4, 1.0 Hz, 1H), 2.12 (ddd, J=14.2, 7.73, 6.81 Hz, 1H), 1.85 (ddd, J=14.2, 6.5, 6.1 Hz, 1H), 1.37 (s, 3H); $^{13}$C NMR (126 MHz, CDCl$_3$) δ 176.6, 171.6, 170.9, 134.8, 132.0, 131.9, 130.0, 129.1, 120.0, 41.9, 41.7, 29.2, 28.2, 22.8; IR (Neat Film NaCl) 3077, 2975, 2935, 1750, 1713, 1683, 1450, 1340, 1239, 1198, 981, 776 cm$^{-1}$; HRMS (MM: ESI-APCI) m/z calc'd for C$_{16}$H$_{18}$NO$_3$ [M+H]$^+$: 272.1281. found 272.1281; [α]$_D^{25}$ −31.3° (c 1.00, CHCl$_3$, 94% ee).

Benzoyl Glutarimide 17

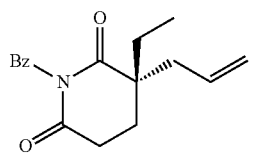

17

Benzoyl glutarimide 17 was isolated by flash chromatography (SiO$_2$, 17 to 25% EtOAc in hexanes) as a colorless oil. 86% yield. R$_f$=0.24 (25% EtOAc in hexanes); $^1$H NMR (500

MHz, CDCl$_3$) δ 7.83 (d, J=8.38 Hz, 2H), 7.64 (t, J=7.46 Hz, 1H), 7.48 (dd, J=8.38, 7.46 Hz, 2H), 5.75 (dddd, J=17.2, 10.2, 7.7, 7.0 Hz, 1H), 5.20-5.15 (m, 2H), 2.86-2.76 (m, 2H), 2.60 (ddt, J=14.0, 7.0, 1.1 Hz, 1H), 2.37 (ddt, J=14.0, 7.7, 1.1 Hz, 1H), 2.05 (ddd, J=14.3, 7.85, 6.81 Hz, 1H), 1.97 (ddd, J=14.3, 6.56, 6.24 Hz, 1H), 1.87-1.75 (m, 2H), 0.97 (t, J=7.46, 3H); $^{13}$C NMR (126 MHz, CDCl$_3$) δ 175.9, 171.6, 171.0, 134.8, 132.4, 131.9, 130.0, 129.0, 119.8, 45.4, 39.3, 29.0, 28.1, 25.4, 8.1; IR (Neat Film NaCl) 3076, 2974, 2940, 2882, 1750, 1713, 1683, 1450, 1340, 1239, 1195, 1001, 923, 778 cm$^{-1}$; HRMS (MM: ESI-APCI) m/z calc'd for C$_{17}$H$_{20}$NO$_3$ [M+H]$^+$: 286.1438. found 286.1432; [α]$_D^{25}$ −16.2° (c 1.00, CHCl$_3$, 96% ee).

Acyl Lactam 18

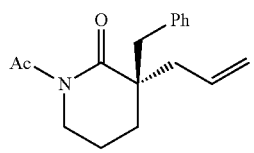

Acyl lactam 18 was isolated by flash chromatography (SiO$_2$, 10 to 20% Et$_2$O in hexanes) as a colorless oil. 88.4% yield. R$_f$=0.40 (35% Et$_2$O in hexanes); $^1$H NMR (500 MHz, CDCl$_3$) δ 7.32-7.17 (m, 3H), 7.17-7.09 (m, 2H), 5.77 (dddd, J=17.0, 10.3, 7.9, 6.8 Hz, 1H), 5.19-5.05 (m, 2H), 3.60-3.48 (m, 1H), 3.44 (dddd, J=13.0, 7.0, 4.6, 1.0 Hz, 1H), 3.27 (d, J=13.3 Hz, 1H), 2.68 (d, J=13.2 Hz, 1H), 2.66-2.62 (m, 1H), 2.51 (s, 3H), 2.23 (ddt, J=13.5, 7.9, 1.1 Hz, 1H), 1.90-1.61 (m, 3H), 1.57-1.38 (m, 1H); $^{13}$C NMR (126 MHz, CDCl$_3$) δ 178.0, 174.2, 137.1, 133.2, 130.4, 128.3, 126.8, 119.2, 49.7, 45.1, 44.8, 44.5, 29.0, 27.6, 19.6; IR (Neat Film NaCl) 3028, 2941, 1691, 1367, 1291, 1247, 111178, 1131, 1031, 923 cm$^{-1}$; HRMS (MM: ESI-APCI) m/z calc'd for C$_{17}$H$_{22}$NO$_2$ [M+H]$^+$: 272.1645. found 272.1646; [α]$_D^{25}$ +11.4° (c 1.03, CHCl$_3$, 88% ee).

Phenyl Carbamate Lactam 19

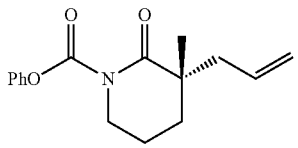

Phenyl Carbamate lactam 19 was isolated by flash chromatography (SiO$_2$, 10 to 20% Et$_2$O in hexanes) as a colorless oil. 82.2% yield. R$_f$=0.39 (35% Et$_2$O in hexanes); $^1$H NMR (500 MHz, CDCl$_3$) δ 7.40-7.35 (m, 2H), 7.25-7.21 (m, 1H), 7.20-7.15 (m, 2H), 5.79 (dddd, J=16.7, 10.4, 7.8, 7.0 Hz, 1H), 5.18-5.08 (m, 2H), 3.89-3.82 (m, 1H), 3.78-3.70 (m, 1H), 2.55 (ddt, J=13.6, 7.0, 1.2 Hz, 1H), 2.33 (ddt, J=13.6, 7.8, 1.1 Hz, 1H), 2.00-1.85 (m, 3H), 1.70-1.59 (m, 1H), 1.30 (s, 3H); $^{13}$C NMR (126 MHz, CDCl$_3$) δ 177.3, 153.8, 150.8, 133.3, 129.3, 125.9, 121.5, 118.9, 48.2, 45.0, 44.1, 33.0, 25.3, 19.6; IR (Neat Film NaCl) 3074, 2939, 2870, 1783, 1733, 1718, 1494, 1299, 1265, 1203, 1153, 991, 920 cm$^{-1}$; HRMS (MM: ESI-APCI) m/z calc'd for C$_{16}$H$_{20}$NO$_3$ [M+H]$^+$: 274.1438. found 274.1444; [α]$_D^{25}$ −81.6° (c 1.11, CHCl$_3$, 94% ee).

Benzyl Carbamate Lactam 20

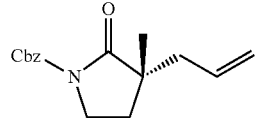

Benzyl carbamate lactam 20 was isolated by flash chromatography (SiO$_2$, 10 to 30% Et$_2$O in hexanes) as a colorless oil. 85.9% yield. R$_f$=0.41 (35% Et$_2$O in hexanes); $^1$H NMR (500 MHz, CDCl$_3$) δ 7.46-7.42 (m, 2H), 7.37 (ddd, J=7.4, 6.3, 1.5 Hz, 2H), 7.35-7.30 (m, 1H), 5.74 (dddd, J=15.9, 11.0, 7.9, 6.9 Hz, 1H), 5.28 (s, 2H), 5.18-5.06 (m, 2H), 3.77-3.63 (m, 2H), 2.33 (ddt, J=13.8, 6.9, 1.2 Hz, 1H), 2.24 (ddt, J=13.8, 7.9, 1.0 Hz, 1H), 2.03 (ddd, J=12.9, 8.1, 6.9 Hz, 1H), 1.74 (ddd, J=13.2, 7.7, 5.9 Hz, 1H), 1.19 (s, 3H); $^{13}$C NMR (126 MHz, CDCl$_3$) δ 178.0, 151.7, 135.3, 133.0, 128.6, 128.3, 128.1, 119.1, 68.0, 45.5, 42.9, 41.7, 29.5, 22.6; IR (Neat Film NaCl) 3066, 2973, 2930, 2903, 1789, 1750, 1719, 1456, 1380, 1363, 1301, 1217, 1001, 919, 776, 736 cm$^{-1}$; HRMS (MM: ESI-APCI) m/z calc'd for C$_{16}$H$_{20}$NO$_3$ [M+H]$^+$: 274.1438. found 274.1438; [α]$_D^{25}$ −41.4° (c 1.02, CHCl$_3$, 91% ee).

4-Phenylbenzoyl Lactam 21

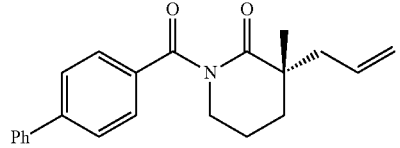

4-Phenylbenzoyl lactam 21 was isolated by flash chromatography (SiO$_2$, 10 to 15% Et$_2$O in pentane) as a colorless oil. 84.6% yield. R$_f$=0.43 (35% Et$_2$O in hexanes); $^1$H NMR (500 MHz, CDCl$_3$) δ 7.64-7.57 (m, 6H), 7.45 (ddd, J=7.8, 6.7, 1.1 Hz, 2H), 7.40-7.34 (m, 1H), 5.84-5.70 (m, 1H), 5.20-5.09 (m, 2H), 3.91-3.82 (m, 1H), 3.74 (ddd, J=12.1, 7.4, 5.7 Hz, 1H), 2.59 (ddd, J=13.7, 7.0, 1.3 Hz, 1H), 2.32 (ddt, J=13.7, 7.7, 1.2 Hz, 1H), 2.10-1.91 (m, 3H), 1.77-1.64 (m, 1H), 1.34 (s, 3H); $^{13}$C NMR (126 MHz, CDCl$_3$) δ 179.1, 175.1, 144.2, 140.2, 135.1, 133.3, 128.8, 128.1, 127.8, 127.2, 126.9, 119.0, 47.2, 44.0, 43.3, 33.3, 25.2, 19.5; IR (Neat Film NaCl) 3073, 2938, 2869, 1677, 1607, 1478, 1383, 1295, 1279, 1145, 922, 849, 743, 698 cm$^{-1}$; HRMS (MM: ESI-APCI) m/z calc'd for C$_{22}$H$_{24}$NO$_2$ [M+H]$^+$: 334.1802. found 334.1812; [α]$_D^{25}$ −82.6° (c 0.75, CHCl$_3$, 99% ee).

1-Naphthoyl Lactam 22

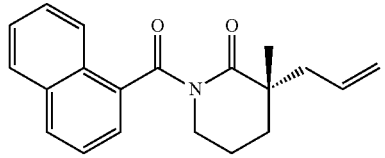

1-Naphthoyl lactam 22 was isolated by flash chromatography (SiO$_2$, 10 to 20% Et$_2$O in hexanes) as a white solid. 86.3% yield. R$_f$=0.42 (35% Et$_2$O in hexanes); $^1$H NMR (500 MHz, CDCl$_3$) δ 8.03-7.97 (m, 1H), 7.90-7.83 (m, 2H), 7.55-

7.46 (m, 2H), 7.42 (dd, J=8.1, 7.1 Hz, 1H), 7.37 (dd, J=7.1, 1.3 Hz, 1H), 5.64 (dddd, J=17.2, 10.2, 7.6, 7.1 Hz, 1H), 5.16-4.97 (m, 2H), 4.05 (dddd, J=12.8, 6.3, 5.2, 1.3 Hz, 1H), 3.95-3.82 (m, 1H), 2.43 (ddt, J=13.7, 7.1, 1.2 Hz, 1H), 2.19 (ddt, J=13.7, 7.6, 1.1 Hz, 1H), 2.11-1.99 (m, 2H), 1.99-1.91 (m, 1H), 1.73-1.64 (m, 1H), 1.18 (s, 3H); $^{13}$C NMR (126 MHz, CDCl$_3$) δ 178.5, 174.3, 135.8, 133.6, 133.1, 130.0, 129.8, 128.4, 126.9, 126.2, 124.9, 124.5, 123.3, 118.9, 46.4, 44.1, 43.3, 33.2, 24.8, 19.5; IR (Neat Film NaCl) 3062, 2937, 2869, 1702, 1677, 1381, 1295, 1251, 1147, 923, 781 cm$^{-1}$; HRMS (MM: ESI-APCI) m/z calc'd for C$_{20}$H$_{22}$NO$_2$ [M+H]$^+$: 308.1645. found 308.1648; [α]$_D^{25}$ −102.3° (c 1.12, CHCl$_3$, 99% ee).

2-Naphthoyl Lactam 23

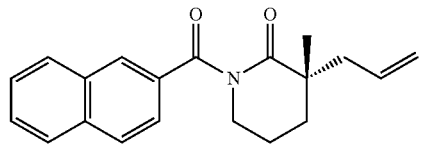

2-Naphthoyl lactam 23 was isolated by flash chromatography (SiO$_2$, 10 to 20% Et$_2$O in hexanes) as a colorless oil. 82.1% yield. R$_f$=0.42 (35% Et$_2$O in hexanes); $^1$H NMR (500 MHz, CDCl$_3$) δ 8.10 (dd, J=1.8, 0.8 Hz, 1H), 7.93-7.76 (m, 3H), 7.63-7.43 (m, 3H), 5.87-5.67 (m, 1H), 5.21-5.06 (m, 2H), 3.95-3.84 (m, 1H), 3.84-3.72 (m, 1H), 2.58 (ddt, J=13.8, 7.1, 1.2 Hz, 1H), 2.33 (ddt, J=13.7, 7.6, 1.1 Hz, 1H), 2.12-1.89 (m, 3H), 1.71 (ddt, J=10.9, 4.9, 4.3, 2.4 Hz, 1H), 1.34 (s, 3H); $^{13}$C NMR (126 MHz, CDCl$_3$) δ 179.0, 175.3, 134.6, 133.7, 133.3, 132.5, 128.9, 128.1, 127.7 (2C), 127.5, 126.4, 124.1, 118.9, 47.2, 44.0, 43.3, 33.3, 25.1, 19.5; IR (Neat Film NaCl) 3059, 2938, 2869, 1677, 1467, 1383, 1293, 1234, 1165, 1139, 923, 862, 822, 780, 762 cm$^{-1}$; HRMS (FAB) m/z calc'd for C$_{20}$H$_{22}$NO$_2$ [M+H]$^+$: 308.1650. found 308.1638; [α]$_D^{25}$ −257.4° (c 0.92, CHCl$_3$, 97% ee).

Procedures for the Conversion of Benzoyl Lactam 3 to Various Derivatives

The benzoyl lactam 3 compound was converted to various derivatives via the reactions described below (and depicted in Benzoyl Lactam 3 Reaction Schemes 1 and 2).

Benzoyl Lactam 3 Reaction Scheme 1

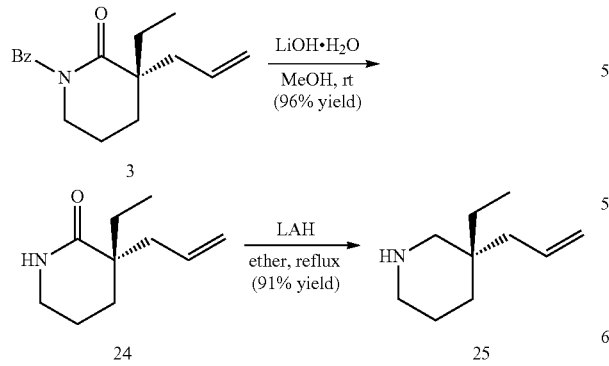

Piperidin-2-One 24

To a solution of lactam 3 (2.00 g, 7.37 mmol, 1.00 equiv) in MeOH (188 mL) was added a solution of LiOH·H$_2$O (464 mg, 11.1 mmol, 1.50 equiv) in H$_2$O (75 mL). After 20 h, the reaction mixture was concentrated under reduced pressure and diluted with saturated aqueous NaHCO$_3$ (100 mL) and EtOAc (75 mL). The phases were separated, and the aqueous phase was extracted with EtOAc (4×75 mL). The combined organic phases were washed with brine (2×30 mL), dried (Na$_2$SO$_4$), filtered, and concentrated under reduced pressure. The resulting oil was purified by flash chromatography (3×25 cm SiO$_2$, 40 to 60% EtOAc in hexanes) to afford known lactam 24 as a colorless oil (1.18 g, 96% yield). See Jakubec, et al., "Cyclic Imine Nitro-Mannich/Lactamization Cascades: A Direct Stereoselective Synthesis of Multicyclic Piperidinone Derivatives," Org. Lett. 10, 4267-4270 (2008), the entire content of which is incorporated by reference. R$_f$=0.21 (50% EtOAc in hexanes); $^1$H NMR (500 MHz, CDCl$_3$) δ 6.05 (br s, 1H), 5.88-5.66 (m, 1H), 5.12-4.95 (m, 2H), 3.25 (td, J=5.8, 1.9 Hz, 2H), 2.48 (ddt, J=13.6, 6.7, 1.3 Hz, 1H), 2.18 (ddt, J=13.6, 8.1, 1.0 Hz, 1H), 1.87-1.62 (m, 5H), 1.49 (dq, J=13.5, 7.4 Hz, 1H), 0.89 (t, J=7.5 Hz, 3H); [α]$_D^{25}$ −13.7° (c 0.57, CHCl$_3$, 99% ee).

Piperidine 25

To a solution of piperidin-2-one 24 (250 mg, 1.49 mmol, 1.00 equiv) in ether (14.9 mL) was added lithium aluminum hydride (170 mg, 4.48 mmol, 3.0 equiv) (Caution: Gas evolution and exotherm). After stirring at ambient temperature for 5 min, the reaction mixture was heated to reflux for 36 h, cooled (0° C.), and quenched with saturated aqueous K$_2$CO$_3$ (20 mL, Caution: Gas evolution and exotherm). The phases were separated, and the aqueous phase was extracted with Et$_2$O (4×75 mL). The combined organic phases were washed with brine (2×30 mL), dried (Na$_2$SO$_4$), filtered, and concentrated under reduced pressure to provide piperidine 23 (206 mg, 90% yield) as a colorless oil. R$_f$=0.29 (20% MeOH in DCM); $^1$H NMR (500 MHz, CDCl$_3$) δ 5.76 (ddt, J=16.4, 10.6, 7.5 Hz, 1H), 5.10-4.96 (m, 2H), 2.81-2.68 (m, 2H), 2.53 (dd, J=13.0, 20.0 Hz, 2H), 2.06 (d, J=7.5 Hz, 2H), 2.02 (br s, 1H), 1.55-1.42 (m, 2H), 1.40-1.30 (m, 2H), 1.32 (q, J=7.5 Hz, 2H), 0.80 (t, J=7.6 Hz, 3H); $^{13}$C NMR (126 MHz, CDCl$_3$) δ 134.6, 116.9, 55.1, 47.0, 39.2, 34.9, 33.6, 27.7, 22.4, 7.1; IR (Neat Film NaCl) 3298, 3073, 2963, 2931, 2853, 2799, 1638, 1462, 1125, 996, 911 cm$^{-1}$; HRMS (MM: ESI-APCI) m/z calc'd for C$_{10}$H$_{20}$N [M+H]$^+$: 154.1590. found 154.1590; [α]$_D^{25}$ −7.5° (c 0.80, MeOH, 96% ee).

Benzoyl Lactam 3 Reaction Scheme 2

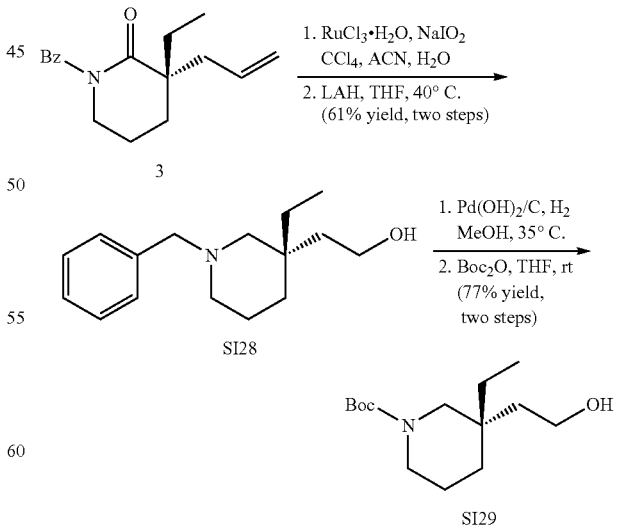

Alcohol SI28

See Moss, et al., "Catalytic enantio- and diastereoselective alkylations with cyclic sulfamidates," Angew. Chem. Int. Ed.

49, 568-571 (2010), the entire content of which is incorporated by reference. To a vigorously stirred mixture of benzoyl lactam 3 (291 mg, 1.07 mmol, 1.00 equiv) and $NaIO_4$ (915 mg, 4.28 mmol, 4.00 equiv) in $CCl_4$ (4.3 mL), MeCN (4.3 mL), and $H_2O$ (6.5 mL) was added $RuCl_3 \cdot H_2O$ (11.0 mg, 0.053 mmol, 0.05 equiv). After 28 h, the reaction mixture was diluted with half-saturated brine (30 mL) and extracted with DCM (5×25 mL). The combined organics were washed with half-saturated brine, dried ($Na_2SO_4$), and concentrated under reduced pressure. The resulting residue was suspended in $Et_2O$ (30 mL) and filtered through a pad of celite. The celite pad was washed with $Et_2O$ (2×15 mL), and the combined filtrate was concentrated under reduced pressure. This crude residue was used in the next step without further purification.

With cooling from a room temperature bath, the above residue was dissolved in THF (19 mL) and then treated with lithium aluminum hydride (487 mg, 12.9 mmol, 12.0 equiv) (Caution: Gas evolution and exotherm). The reaction mixture was stirred at ambient temperature for 12 h and then warmed to 40° C. for an addition 12 h. The reaction mixture was then cooled (0° C.) and dropwise treated with brine (20 mL, Caution: Gas evolution and exotherm). Once gas evolution had ceased the reaction mixture was diluted with half-saturated brine (20 mL) and EtOAc (20 mL). The phases were separated and the aqueous phase was extracted with EtOAc (5×50 mL). The combined organic phases were dried ($Na_2SO_4$), filtered, and concentrated under reduced pressure. The resulting oil was purified by flash chromatography (3×12 cm $SiO_2$, 35 to 70% EtOAc in hexanes) to afford alcohol SI28 as a colorless oil (162 mg, 61% yield for two steps). $R_f$=0.36 (75% EtOAc in hexanes); $^1$H NMR (500 MHz, $CDCl_3$) δ 7.35-7.24 (m, 5H), 3.80-3.72 (m, 1H), 3.71-3.60 (m, 2H), 3.31 (br s, 1H), 2.85-2.70 (br s, 2H), 2.00-1.70 (br s, 4H), 1.66-1.45 (m, 3H), 1.35-1.10 (m, 3H), 0.81 (t, J=7.5 Hz, 3H); $^{13}$C NMR (126 MHz, $CDCl_3$) δZ 129.5, 128.4, 127.4, 63.9, 63.4, 59.4, 52.9, 39.9, 35.9, 35.1, 33.4, 22.4, 7.5; IR (Neat Film NaCl) 3345 (br), 2933, 2793, 1453, 1350, 1115, 1040, 1028, 739 $cm^{-1}$; HRMS (MM: ESI-APCI) m/z calc'd for $C_{16}H_{26}NO$ $[M+H]^+$: 248.2009. found 248.2016.

Alcohol SI29

A mixture of alcohol SI28 (162.3 mg, 0.656 mmol, 1.00 equiv) and 20% $Pd(OH)_2$/C (50 mg) in MeOH (15 mL) was stirred under an $H_2$ atmosphere for 3.5 h. The reaction mixture was filtered through a pad of celite. The celite pad was washed with MeOH (2×15 mL), and the combined filtrate was concentrated under reduced pressure. This crude residue was used in the next step without further purification.

To a solution of the above residue in THF (10 mL) was added $Boc_2O$ (150 mg, 0.689 mmol, 1.05 equiv). After stirring for 24 h, the reaction mixture was concentrated under reduced pressure and partitioned between DCM (20 mL) and saturated aqueous $NaHCO_3$ (20 mL). The organic layer was dried ($Na_2SO_4$), filtered, and concentrated under reduced pressure. The resulting oil was purified by flash chromatography (2×20 cm $SiO_2$, 15 to 35% EtOAc in hexanes) to afford alcohol SI29 as a colorless oil (130 mg, 77% yield for two steps). $R_f$=0.34 (35% EtOAc in hexanes); $^1$H NMR (500 MHz, $CDCl_3$) δ 3.74-3.60 (m, 2H), 3.48 (br s, 1H), 3.31 (br s, 1H), 3.20 (br s, 1H), 2.96 (br s, 1H), 2.16 (br s, 1H), 1.66-1.55 (m, 1H), 1.55-1.42 (m, 3H), 1.44 (s, 9H), 1.40-1.27 (m, 2H), 1.25-1.15 (m, 1H), 0.83 (t, J=7.5 Hz, 3H); $^{13}$C NMR (126 MHz, $CDCl_3$) δ 155.2, 79.4, 58.7, 52.5, 44.5, 36.1, 35.3, 34.6, 28.4, 27.6, 21.2, 7.4; IR (Neat Film NaCl) 3439 (br), 2967, 2934, 2861, 1693, 1670, 1429, 1365, 1275, 1248, 1162, 1045, 865, 767 $cm^{-1}$; HRMS (MM: ESI-APCI) m/z calc'd for $C_{14}H_{28}NO_3$ $[M+H]^+$: 258.2064. found 258.2069; $[α]_D^{25}$ −7.0° (c 1.13, $CHCl_3$, 96% ee).

TABLE 4

Methods for the Determination of Enantiomeric Excess for the above Examples
In the below Table, HPLC refers to high performance liquid chromatography and SFC refers supercritical fluid chromatography. Also, ChiralPak and Chiralcel refer to the companies from which the column resin (i.e., stationary phase) was obtained, and the lettering appearing after the company name refers to the specific material used.

| entry | product | assay conditions | retention time of major isomer (min) | retention time of minor isomer (min) | % ee |
|---|---|---|---|---|---|
| 1 | 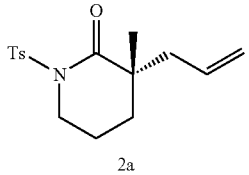 [SMILES: C=CC[C@]1(C)CCCN(S(=O)(=O)c2ccc(C)cc2)C1=O]<br>2a | HPLC<br>Chiralpak AD-H<br>5% EtOH in hexanes<br>isocratic, 1.0 mL/min<br>254 nm | 19.10 | 15.77 | 75 |
| 2 | 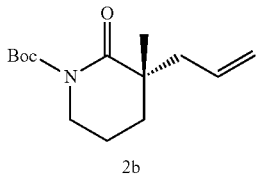<br>2b | HPLC<br>Chiralcel OJ-H<br>0.1% IPA in hexanes<br>isocratic, 1.0 mL/min<br>220 nm | 15.22 | 18.10 | 81 |
| 3 | 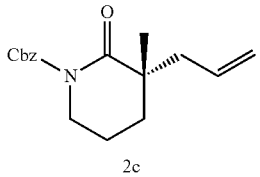 [SMILES: C=CC[C@]1(C)CCCN(C(=O)OCc2ccccc2)C1=O]<br>2c | HPLC<br>Chiralcel OJ-H<br>3% EtOH in hexanes<br>isocratic, 1.0 mL/min<br>220 nm | 18.68 | 17.60 | 86 |

TABLE 4-continued

Methods for the Determination of Enantiomeric Excess for the above Examples
In the below Table, HPLC refers to high performance liquid chromatography and SFC
refers supercritical fluid chromatography. Also, ChiralPak and Chiralcel refer to the companies
from which the column resin (i.e., stationary phase) was obtained, and the lettering appearing after
the company name refers to the specific material used.

| entry | product | assay conditions | retention time of major isomer (min) | retention time of minor isomer (min) | % ee |
|---|---|---|---|---|---|
| 4 | 2d | HPLC Chiralcel OD 3% EtOH in hexanes isocratic, 1.0 mL/min 254 nm | 28.89 | 21.47 | 89 |
| 5 | 2e | HPLC Chiralcel OJ 1% IPA in hexanes isocratic, 1.0 mL/min 254 nm | 10.15 | 9.71 | 91 |
| 6 | 2f | HPLC Chiralcel OD-H 3% IPA in hexanes isocratic, 1.0 mL/min 254 nm | 15.73 | 18.12 | 99 |
| 7 | 2g | HPLC Chiralcel OJ-H 2% IPA in hexanes isocratic, 1.0 mL/min 254 nm | 29.12 | 19.74 | 99 |
| 8 | 2h | HPLC Chiralcel OJ-H 5% IPA in hexanes isocratic, 1.0 mL/min 254 nm | 32.97 | 31.16 | 99 |
| 9 | 3 | SFC Chiralcel OJ-H 3% MeOH in CO$_2$ isocratic, 5.0 mL/min 254 nm | 3.85 | 2.49 | 99 |
| 10 | 4 | SFC Chiralcel OD-H 10% MeOH in CO$_2$ isocratic, 5.0 mL/min 254 nm | 3.84 | 3.20 | 99 |

TABLE 4-continued

Methods for the Determination of Enantiomeric Excess for the above Examples
In the below Table, HPLC refers to high performance liquid chromatography and SFC
refers supercritical fluid chromatography. Also, ChiralPak and Chiralcel refer to the companies
from which the column resin (i.e., stationary phase) was obtained, and the lettering appearing after
the company name refers to the specific material used.

| entry | product | assay conditions | retention time of major isomer (min) | retention time of minor isomer (min) | % ee |
|---|---|---|---|---|---|
| 11 | 5 | HPLC Chiralpak AD-H 3% EtOH in hexane isocratic, 1.0 mL/min 254 nm | 32.69 | 27.83 | 99 |
| 12 | 6 | SFC Chiralpak IC 10% MeOH in $CO_2$ isocratic, 5.0 mL/min 254 nm | 2.67 | 3.84 | 99 |
| 13 | 7 | HPLC Chiralcel OJ-H 3% IPA in hexane isocratic, 1.0 mL/min 254 nm | 7.75 | 5.95 | 96 |
| 14 | 8 | HPLC Chiralcel OJ-H 8% IPA in hexane isocratic, 1.0 mL/min 254 nm | 25.94 | 19.12 | 97 |
| 15 | 9 | HPLC Chiralpak AD 2% IPA in hexane isocratic, 1.0 mL/min 254 nm | 18.72 | 27.05 | 95 |
| 16 | 10 | SFC Chiralcel OJ-H 10% MeOH in $CO_2$ isocratic, 5.0 mL/min 254 nm | 2.93 | 1.84 | 98 |

TABLE 4-continued

Methods for the Determination of Enantiomeric Excess for the above Examples
In the below Table, HPLC refers to high performance liquid chromatography and SFC
refers supercritical fluid chromatography. Also, ChiralPak and Chiralcel refer to the companies
from which the column resin (i.e., stationary phase) was obtained, and the lettering appearing after
the company name refers to the specific material used.

| entry | product | assay conditions | retention time of major isomer (min) | retention time of minor isomer (min) | % ee |
|---|---|---|---|---|---|
| 17 | 11 | SFC Chiralcel OJ-H 5% MeOH in $CO_2$ isocratic, 5.0 mL/min 254 nm | 2.31 | 3.73 | 93 |
| 18 | 12 | SFC Chiralpak AD-H 15% MeOH in $CO_2$ isocratic, 5.0 mL/min 254 nm | 4.16 | 5.05 | 99 |
| 19 | 13 | HPLC Chiralcel OJ-H 5% IPA in hexane isocratic, 1.0 mL/min 254 nm | 29.16 | 24.82 | 93 |
| 20 | 14 | SFC Chiralpak AD-H 10% MeOH in $CO_2$ isocratic, 5.0 mL/min 254 nm | 1.96 | 1.41 | 99 |
| 21 | 15 | SFC Chiralcel OJ-H 5% MeOH in $CO_2$ isocratic, 5.0 mL/min 254 nm | 2.55 | 2.25 | 99 |
| 22 | 16 | SFC Chiralcel OJ-H 3% MeOH in $CO_2$ isocratic, 5.0 mL/min 254 nm | 3.05 | 2.72 | 94 |
| 23 | 17 | SFC Chiralpak OJ-H 3% MeOH in $CO_2$ isocratic, 5.0 mL/min 254 nm | 3.28 | 2.87 | 96 |

TABLE 4-continued

Methods for the Determination of Enantiomeric Excess for the above Examples
In the below Table, HPLC refers to high performance liquid chromatography and SFC
refers supercritical fluid chromatography. Also, ChiralPak and Chiralcel refer to the companies
from which the column resin (i.e., stationary phase) was obtained, and the lettering appearing after
the company name refers to the specific material used.

| entry | product | assay conditions | retention time of major isomer (min) | retention time of minor isomer (min) | % ee |
|---|---|---|---|---|---|
| 24 | 18 | SFC Chiralpak AD-H 3% MeOH in $CO_2$ isocratic, 3.0 mL/min 235 nm | 4.03 | 4.69 | 88 |
| 25 | 19 | SFC Chiralcel OB-H 10% MeOH in $CO_2$ isocratic, 5.0 mL/min 210 nm | 2.65 | 2.39 | 94 |
| 26 | 20 | SFC Chiralpak AD-H 15% MeOH in $CO_2$ isocratic, 5.0 mL/min 210 nm | 4.23 | 2.51 | 91 |
| 27 | 21 | SFC Chiralcel OJ-H 10% MeOH in $CO_2$ isocratic, 5.0 mL/min 254 nm | 4.53 | 3.80 | 99 |
| 28 | 22 | SFC Chiralcel OB-H 10% MeOH in $CO_2$ isocratic, 5.0 mL/min 210 nm | 4.05 | 4.60 | 99 |
| 29 | 23 | SFC Chiralpak AD-H 20% MeOH in $CO_2$ isocratic, 5.0 mL/min 254 nm | 3.73 | 2.93 | 97 |

Piperazinone Examples

Some exemplary piperazinone building blocks were prepared according to the below reaction schemes.

Preparation of Piperazinone Building Block Compound 2

Piperazinone building block compound 2 was prepared according the following piperazinone Reaction Scheme 1 according to the following reaction particulars.

Piperazinone Reaction Scheme 1

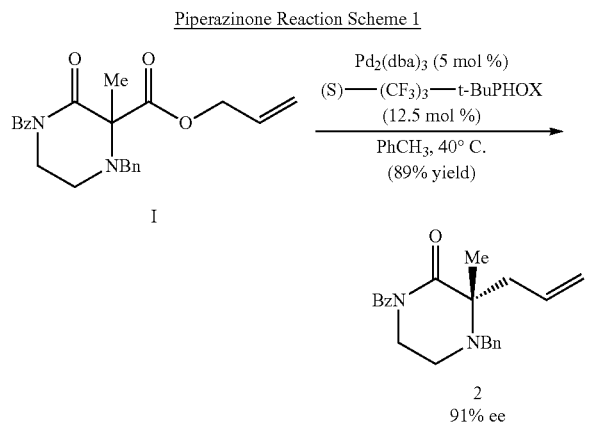

According to the above piperazinone Reaction Scheme 1, in a nitrogen-filled glovebox, an oven-dried 2 dram vial was charged with $Pd_2 dba_3$ (21.3 mg, 0.023 mmol, 0.05 equiv), (S)—$(CF_3)_3$-t-Bu-PHOX (34.3 mg, 0.058 mmol, 0.125 equiv), toluene (10 mL), and a magnetic stir bar. The vial was stirred at ambient glovebox temperature (~28° C.) for 30 min and 1 (182 mg, 0.464 mmol, 1.00 equiv) was added as a solution in toluene (5 mL). The vial was sealed and heated to 40° C. After 17 hours, complete consumption of the starting material was observed by colorimetric change (from light green to red-orange) and confirmed by thin layer chromatography on $SiO_2$. The reaction mixture was removed from the glovebox, concentrated under reduced pressure, and purified by flash chromatography (SiO 4:1 hexane:ethyl acetate) to afford piperazinone 2 (145 mg, 0.413 mmol, 89% yield) as a pale yellow oil; $^1$H NMR (500 MHz, $CDCl_3$) δ 7.57-7.55 (m, 2H), 7.50-7.47 (m, 1H), 7.42-7.26 (m, 7H), 6.10-6.02 (m, 1H), 5.19-5.13 (m, 2H), 4.02 (d, J=13.5 Hz, 1H), 3.89-3.86 (m, 1H), 3.62-3.57 (m, 1H), 3.42 (d, J=13.5 Hz, 1H), 2.91-2.79 (m, 3H), 2.66-2.62 (m, 1H), 1.41 (s, 3H).

Preparation of Piperazinone Building Block Compound 4

Piperazinone building block compound 4 was prepared according the following piperazinone Reaction Scheme 2 according to the following reaction particulars.

Piperazinone Reaction Scheme 2

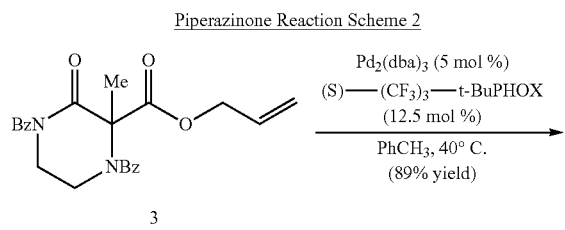

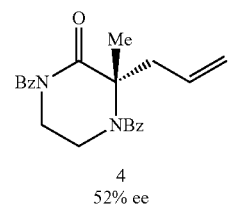

According to piperazinone Reaction Scheme 2, in a nitrogen-filled glovebox, an oven-dried 2 dram vial was charged with $Pd_2 dba_3$ (22.9 mg, 0.025 mmol, 0.05 equiv), (S)—$(CF_3)_3$-t-Bu-PHOX (37.0 mg, 0.063 mmol, 0.125 equiv), toluene (10 mL), and a magnetic stir bar. The vial was stirred at ambient glovebox temperature (~28° C.) for 30 min and 3 (203 mg, 0.50 mmol, 1.00 equiv) was added as a solution in toluene (5 mL). The vial was sealed and heated to 40° C. After 7 hours, complete consumption of the starting material was observed by colorimetric change (from light green to red-orange) and confirmed by thin layer chromatography on $SiO_2$. The reaction mixture was removed from the glovebox, concentrated under reduced pressure, and purified by flash chromatography ($SiO_2$, 4:1 hexane:ethyl acetate) to afford piperazinone 4 (161 mg, 0.445 mmol, 89% yield) as a pale yellow oil; $^1$H NMR (500 MHz, $CDCl_3$) δ 7.57-7.51 (m, 3H), 7.46-7.40 (m, 7H), 5.89-5.81 (m, 1H), 5.26-5.18 (m, 2H), 4.16-4.12 (m, 1H), 3.82-3.69 (m, 2H), 3.63-3.50 (m, 2H), 2.90-2.85 (m, 1H), 1.99 (s, 3H).

Preparation of Piperazinone Building Block Compound 6

Piperazinone building block compound 6 was prepared according the following piperazinone Reaction Scheme 3 according to the following reaction particulars.

Piperazinone Reaction Scheme 3

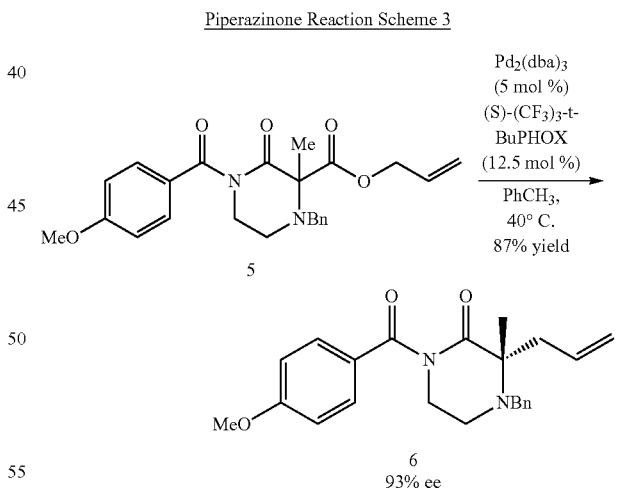

According to piperazinone Reaction Scheme 3, in a nitrogen-filled glovebox, an oven-dried 2 dram vial was charged with $Pd_2 dba_3$ (1.7 mg, 0.002 mmol, 0.05 equiv), (S)—$(CF_3)_3$-t-Bu-PHOX (2.5 mg, 0.0047 mmol, 0.125 equiv), toluene (0.5 mL), and a magnetic stir bar. The vial was stirred at ambient glovebox temperature (−28° C.) for 30 min and 5 (15.5 mg, 0.038 mmol, 1.00 equiv) was added as a solution in toluene (0.5 mL). The vial was sealed and heated to 40° C. After 18 hours, complete consumption of the starting material was observed by colorimetric change (from light green to red-orange) and confirmed by thin layer chromatography on SiO$_2$. The reaction mixture was removed from the glovebox, concentrated under reduced pressure, and purified by flash chromatography (SiO$_2$, 4:1 hexane:ethyl acetate) to afford piperazinone 6 (12.5 mg, 0.033 mmol, 87% yield) as a pale yellow oil; $^1$H NMR (500 MHz, CDCl$_3$) δ 7.66-7.58 (m, 2H), 7.42-7.26 (m, 5H), 6.90-6.86 (m, 2H), 5.63 (ddt, J=17.0, 10.3, 7.0 Hz, 1H), 5.19-5.12 (m, 2H), 4.02 (d, J=13.7 Hz, 2H), 3.85 (s, 3H), 3.83-3.77 (m, 1H), 3.62-3.53 (m, 1H), 3.41 (d, J=13.7 Hz, 2H), 2.91-2.79 (m, 3H), 2.66-2.59 (m 1H), 1.45 (s, 3H).

Additional Examples

Some additional building block compounds were prepared according to the below reaction schemes.

Preparation of Acyclic Building Block Compound 2

Acyclic building block compound 2 was prepared from acyclic substrate compound 1 according to the following Acyclic Reaction Scheme.

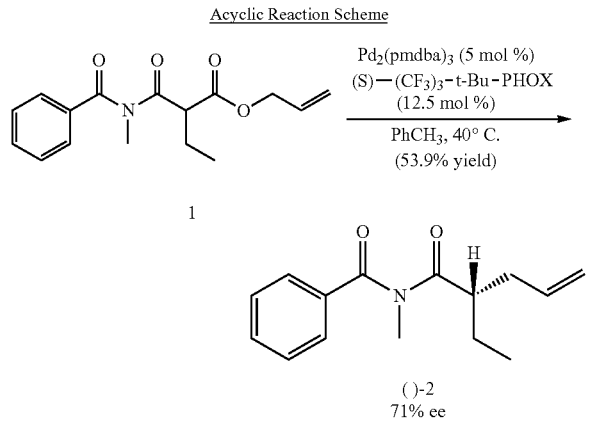

According to the Acyclic Reaction Scheme above, in a nitrogen-filled glovebox, an oven-dried 20 mL vial was charged with Pd$_2$ pmdba$_3$ (27.4 mg, 0.025 mmol, 0.05 equiv), (S)—(CF3)3-t-Bu-PHOX (37.0 mg, 0.0625 mmol, 0.125 equiv), toluene (13 mL), and a magnetic stir bar. The vial was stirred at ambient glovebox temperature (~28° C.) for 30 min and 1 (144.6 mg, 0.50 mmol, 1.00 equiv) was added as a solution in toluene (2 mL). The vial was sealed and heated to 40° C. After 37 hours, complete consumption of the starting material was observed by colorimetric change (from light green to red-orange) and confirmed by thin layer chromatography on SiO$_2$. The reaction mixture was removed from the glovebox, concentrated under reduced pressure, and purified by flash chromatography (SiO$_2$, 3×25 cm, 19:1→14:1→9:1 hexane:diethyl ether) to afford imide 2 (66.2 mg, 0.013 mmol, 53.9% yield) as a pale yellow oil; $^1$H NMR (500 MHz, CDCl$_3$) δ 7.68-7.52 (m, 3H), 7.52-7.43 (m, 2H), 5.70 (ddt, J=17.2, 10.2 Hz, 1H), 2.28-2.18 (m, 1, 7.1 Hz, 1H), 5.09-4.97 (m, 2H), 3.19 (s, 3H), 2.99 (tt, J=7.6, 6.0 Hz, 1H), 2.40 (dtt, J=13.9, 7.5, 11H), 1.72 (dp, J=13.4, 7.5 Hz, 1H), 1.60-1.47 (m, 1H), 0.88 (t, J=7.4 Hz, 3H).

Preparation of Lactone Building Block Compound 4

Lactone building block compound 4 was prepared from lactone substrate compound 3 according to the following Lactone Reaction Scheme.

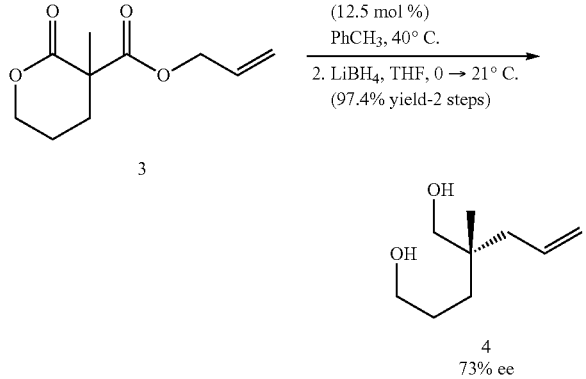

According to the Lactone Reaction Scheme, above, in a nitrogen-filled glovebox, an oven-dried 20 mL vial was charged with Pd$_2$ dba$_3$ (27.4 mg, 0.025 mmol, 0.05 equiv), (S)-t-Bu-PHOX (24.2 mg, 0.0625 mmol, 0.125 equiv), toluene (13 mL), and a magnetic stir bar. The vial was stirred at ambient glovebox temperature (~28° C.) for 30 min and 3 (99.0 mg, 0.50 mmol, 1.00 equiv) was added as a solution in toluene (2 mL). The vial was sealed and heated to 40° C. After 30 hours, complete consumption of the starting material was observed by colorimetric change (from light green to red-orange) and confirmed by thin layer chromatography on SiO$_2$. The reaction mixture was removed from the glovebox, concentrated under reduced pressure, and taken up in 10 mL THF. The solution was cooled to 0° C. with an ice-water bath and LiBH$_4$ (1.0 mL 2.0 M solution in THF, 2.0 mmol, 4 equiv) was added. After 30 minutes stirring, an additional charge of LiBH4 1.0 mL 2.0 M solution in THF, 2.0 mmol, 4 equiv) was added. After 40 additional minutes of stirring, the ice-water bath was removed to allow the reaction to warm to room temperature (~21° C.). After more hours stirring at room temperature, the reaction was complete as observed by thin layer chromatography on SiO$_2$. The reaction mixture was poured into a mixture of water and ethyl acetate. A 1.0 M solution of HCl in water was added slowly. The aqueous phase was extracted five times with ethyl acetate. The combined organic layers were washed with brine and concentrated under reduced pressure. The resulting crude product was purified by flash chromatography (SiO$_2$, 1.5×20 cm, 19:1→7:3→1:1→7:3 hexane:diethyl ether) to afford diol 4 (77.1 mg, 0.049 mmol, 97.4% yield) as a pale yellow oil; $^1$H NMR (500 MHz, CDCl$_3$) δ 5.84 (ddt, J=16.4, 10.5, 7.5 Hz, 1H), 5.11-5.02 (m, 2H), 4.12 (q, J=7.1 Hz, 1H), 3.69-3.51 (m, 2H), 3.37 (d, J=0.8 Hz, 2H), 2.08-1.92 (m, 3H), 1.62-1.42 (m, 2H), 1.42-1.18 (m, 2H), 0.86 (s, 3H).

Preparation of Imide Building Block Compound 6

Imide building block compound 6 was prepared from imide substrate compound 6 according to the following Imide Reaction Scheme.

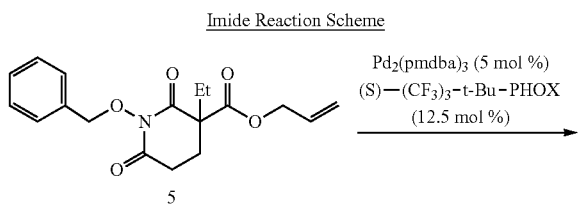

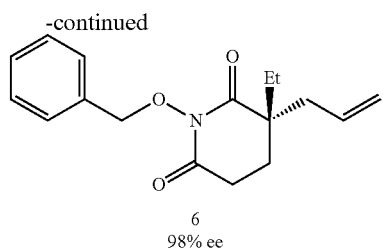

6
98% ee

According to the Imide Reaction Scheme, above, in a nitrogen-filled glovebox, an oven-dried 2 dram vial was charged with $Pd_2$ pmdba$_3$ (5.0 mg, 0.005 mmol, 0.05 equiv), (S)—(CF3)3-t-Bu-PHOX (7.7 mg, 0.013 mmol, 0.125 equiv), toluene (3 mL), and a magnetic stir bar. The vial was stirred at ambient glovebox temperature (~28° C.) for 30 min and 5 (33 mg, 0.10 mmol, 1.00 equiv) was added as a solution in toluene (0.3 mL). The vial was sealed and heated to 40° C. After 5 days, complete consumption of the starting material was observed by colorimetric change (from light green to red-orange) and confirmed by thin layer chromatography on $SiO_2$. The reaction mixture was removed from the glovebox, concentrated under reduced pressure, and purified by flash chromatography ($SiO_2$, 4:1 hexane:ethyl acetate) to afford imide 6 (23 mg, 0.08 mmol, 80% yield) as a pale yellow oil; $^1$H NMR (500 MHz, CDCl$_3$) δ 7.55-7.47 (m, 2H), 7.36 (dd, J=5.0, 2.0 Hz, 3H), 5.63 (ddt, J=17.3, 10.3, 7.4 Hz, 1H), 5.15-5.06 (m, 2H), 4.99 (s, 2H), 2.80-2.65 (m, 2H), 2.45 (ddt, J=14.2, 7.0, 1.3 Hz, 1H), 2.26 (ddt, J=14.0, 8.0, 1.1 Hz, 1H), 1.84-1.63 (m, 3H), 0.86 (t, J=7.5 Hz, 3H).

While certain exemplary embodiments of the present invention have been illustrated and described, those of ordinary skill in the art will understand that various modifications and changes can be made to the described embodiments without departing from the spirit and scope of the present invention, as defined by the following claims.

What is claimed is:

1. A method of making an enantioenriched heteroatom-containing compound, the method comprising subjecting a compound of Formula A to palladium-catalyzed decarboxylative alkylation using an electron-poor ligand, a palladium-based catalyst, and a solvent:

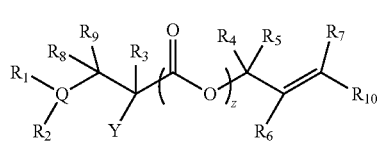

wherein:
z is 1;
Q is N;
each of $R_1$ through $R_{10}$ is independently hydrogen, a substituted or unsubstituted hydrocarbyl group, a substituted or unsubstituted heteroatom-containing hydrocarbyl group, or a functional group;
Y is hydrogen, a heteroatom, a substituted or unsubstituted hydrocarbyl group, a substituted or unsubstituted heteroatom-containing hydrocarbyl group, or a functional group; and
two or more groups selected from $R_1$ through $R_{10}$ and Y optionally combine to form a ring or a carbonyl group.

2. The method of claim 1, wherein the electron-poor ligand comprises a ligand including an electron-poor moiety selected from the group consisting of fluorine atoms, partially or fully fluorinated hydrocarbyl groups, partially or fully fluorinated heteroatom-containing hydrocarbyl groups, $NO_2$ groups and $SO_2R$ groups, wherein R is hydrogen, a substituted or unsubstituted hydrocarbyl group, a substituted or unsubstituted heteroatom-containing hydrocarbyl group, or a functional group.

3. The method of claim 1, wherein the electron-poor ligand comprises a R'-PHOX ligand, wherein R' is selected from the group consisting of $(CF_3)_3$ groups, partially or fully fluorinated hydrocarbyl groups, partially or fully fluorinated heteroatom-containing hydrocarbyl groups, $NO_2$ groups and $SO_2R$ groups, wherein R is hydrogen, a substituted or unsubstituted hydrocarbyl group, a substituted or unsubstituted heteroatom-containing hydrocarbyl group, or a functional group.

4. The method of claim 1, wherein $R_8$ and $R_9$ combine to form a carbonyl group.

5. The method of claim 1, wherein $R_2$ and Y combine to form a ring with Q, the ring including between 3 and 12 atoms.

6. The method of claim 5, wherein the ring includes between 4 and 7 ring atoms.

7. The method of claim 1, wherein $R_2$ and Y combine to form a ring including at least one double bond.

8. The method of claim 1, wherein $R_1$ is an amine-protecting group.

9. The method of claim 1, wherein $R_1$ is OH.

10. The method of claim 1, wherein the compound of Formula A is a compound represented by Formula C:

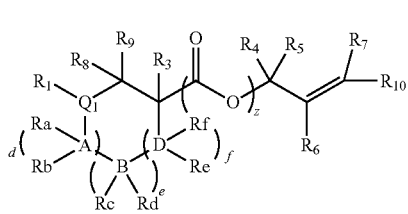

wherein:
z is 1;
each of d, e and f is independently an integer of 0 or greater;
$Q_1$ is N;
each of A, B and D is independently a heteroatom or a carbon atom, and an A atom that is directly adjacent the $Q_1$ atom is not a chiral center; and
each of $R_a$ through $R_f$ is either:
independently hydrogen, a substituted or unsubstituted hydrocarbyl group, a substituted or unsubstituted heteroatom-containing hydrocarbyl group, or a functional group; or
combines with another of $R_a$ through $R_f$ to form a double bond or a carbonyl group.

11. The method of claim 10, wherein $R_8$ and $R_9$ combine to form a carbonyl group such that the compound of Formula C is represented by Formula C(i):

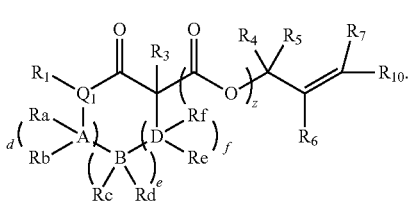

12. The method of claim 10, wherein $R_1$ and one $R_a$ combine to form a double bond, or one $R_b$ and one $R_c$ combine to form a double bond, or one $R_d$ and one $R_e$ combine to form a double bond.

13. The method of claim 10, wherein one $R_a$ and one $R_b$ combine to form a carbonyl group, or one $R_c$ and one $R_d$ combine to form a carbonyl group, or one $R_e$ and one $R_f$ combine to form a carbonyl group.

14. The method of claim 1, wherein the enantioenriched heteroatom-containing compound is selected from:

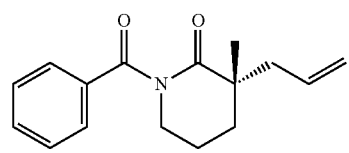

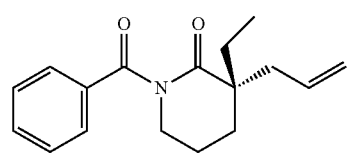

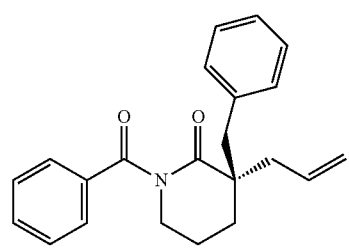

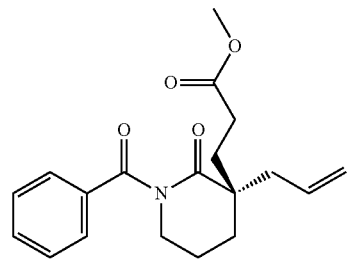

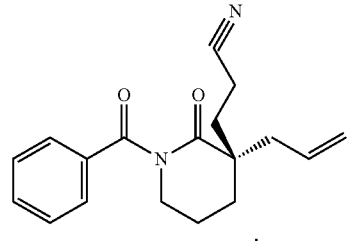

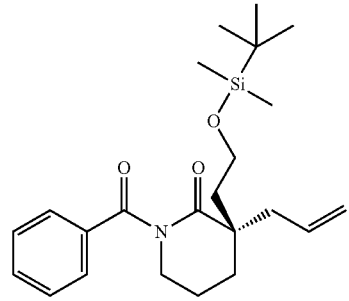

-continued

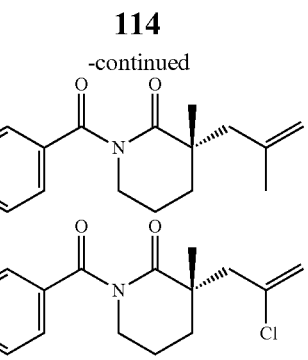

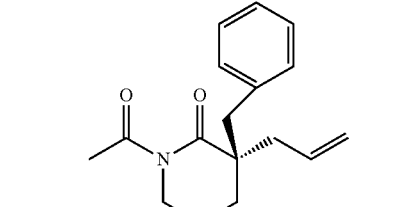

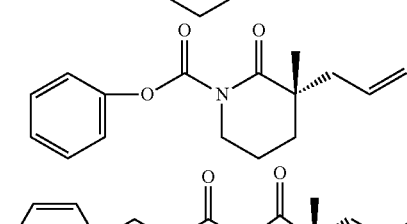

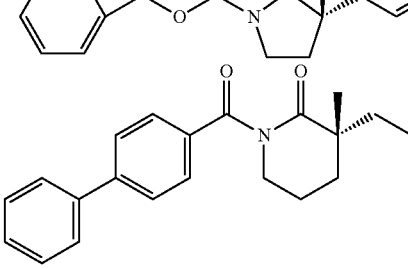

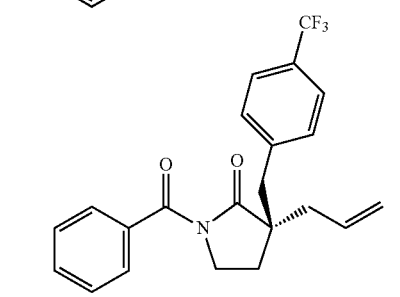

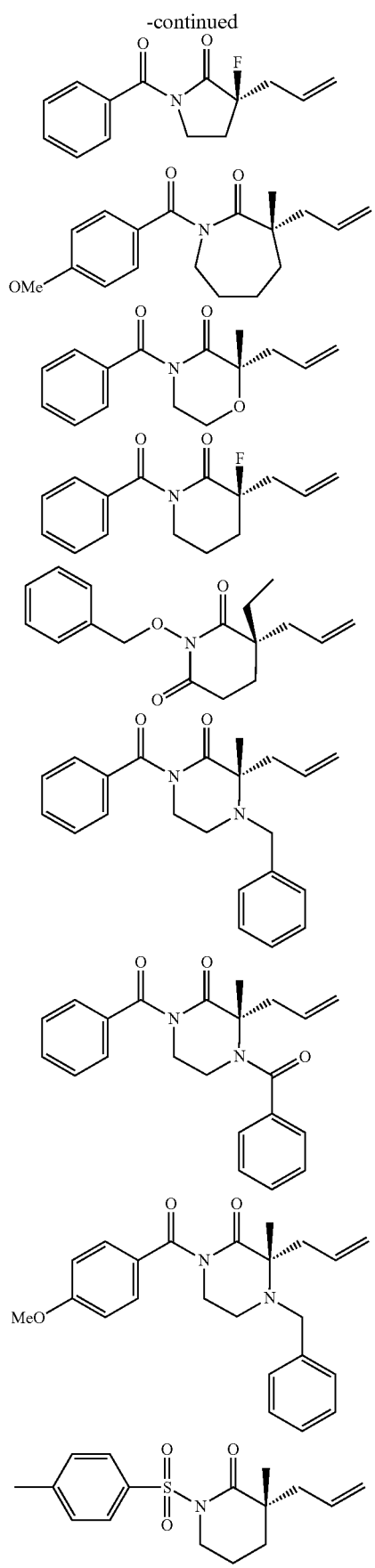
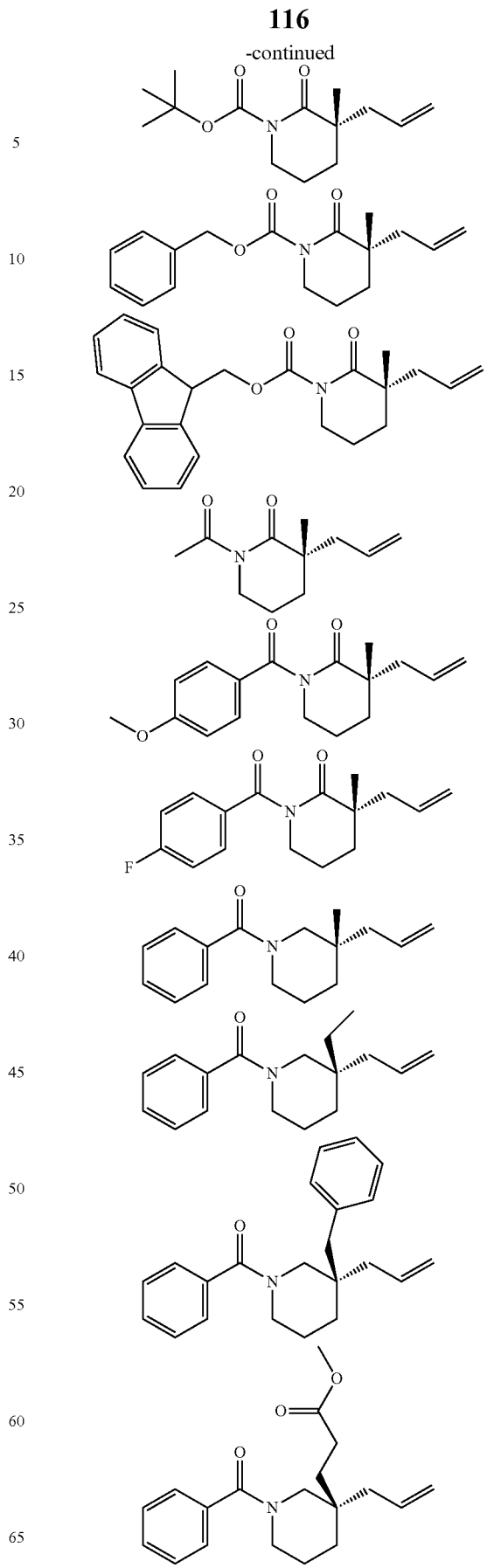

117
-continued
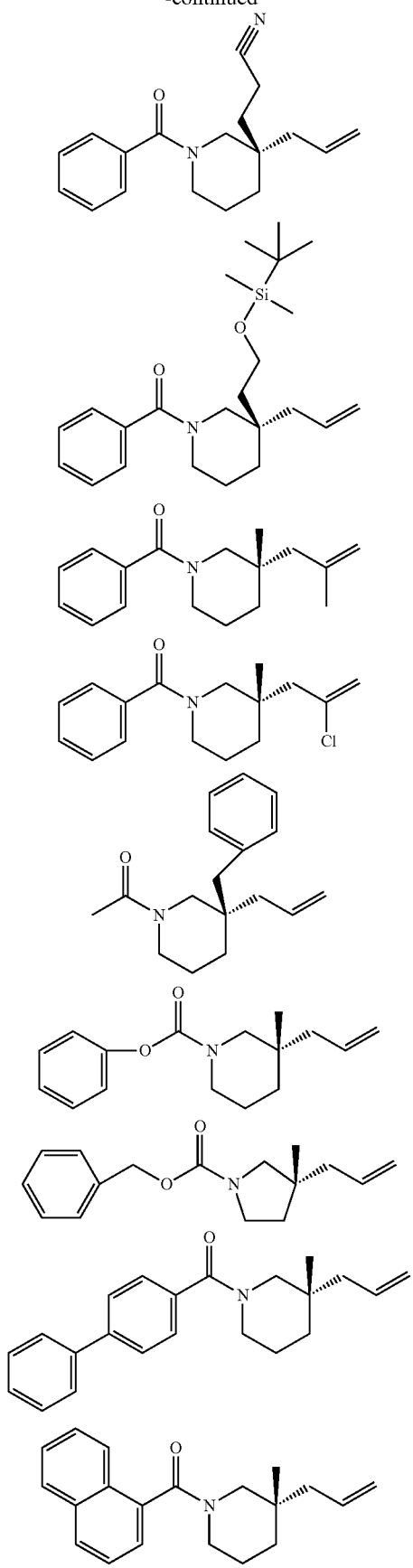
118
-continued
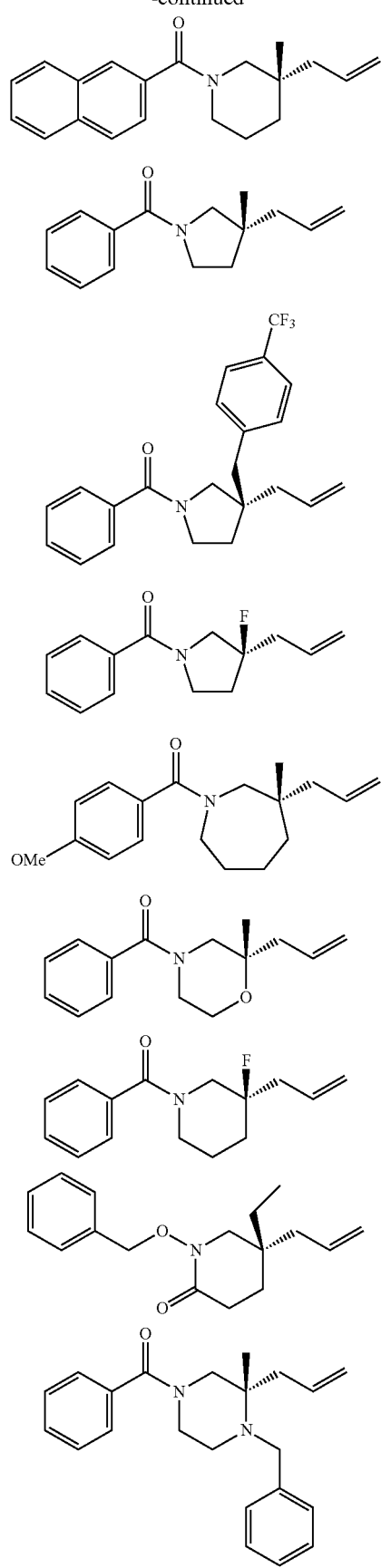

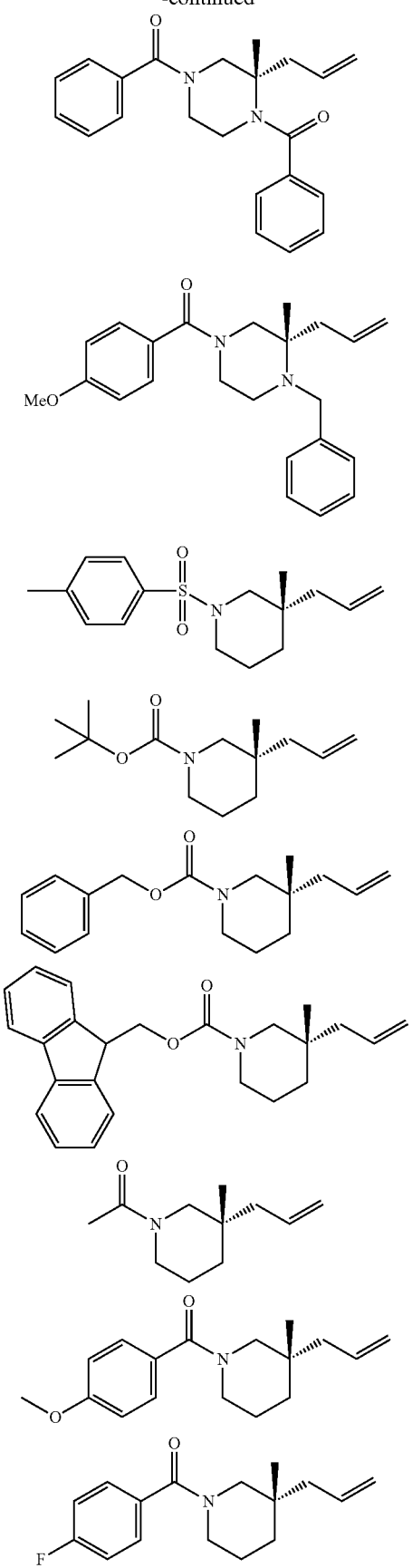
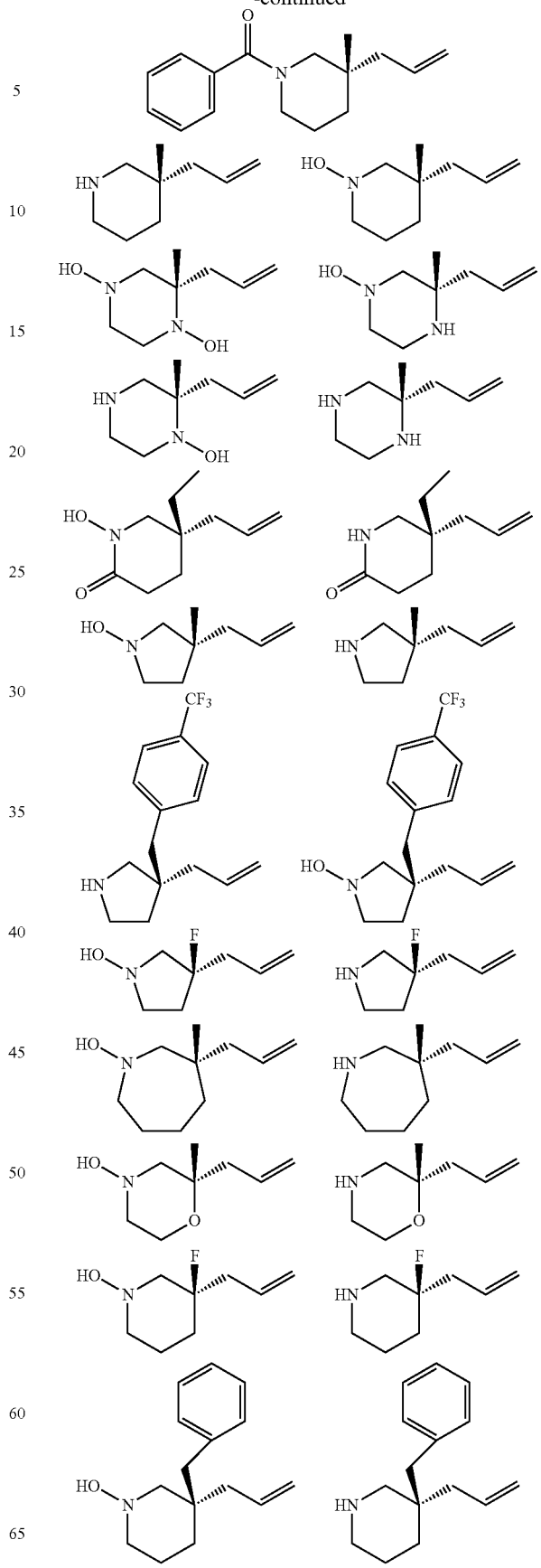

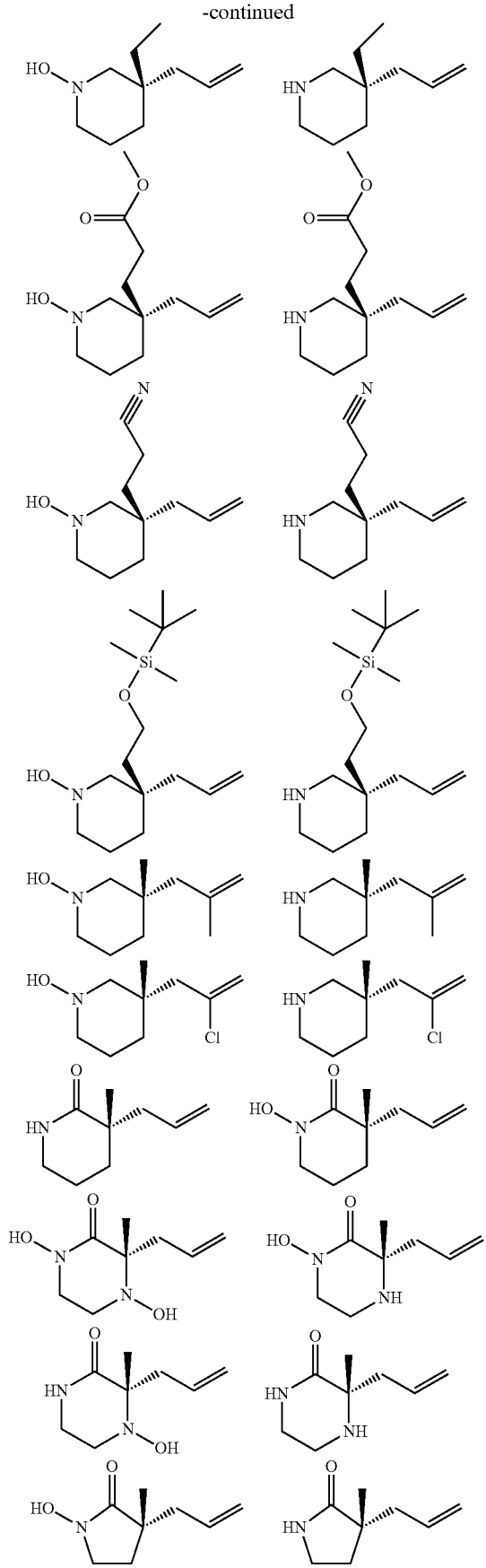
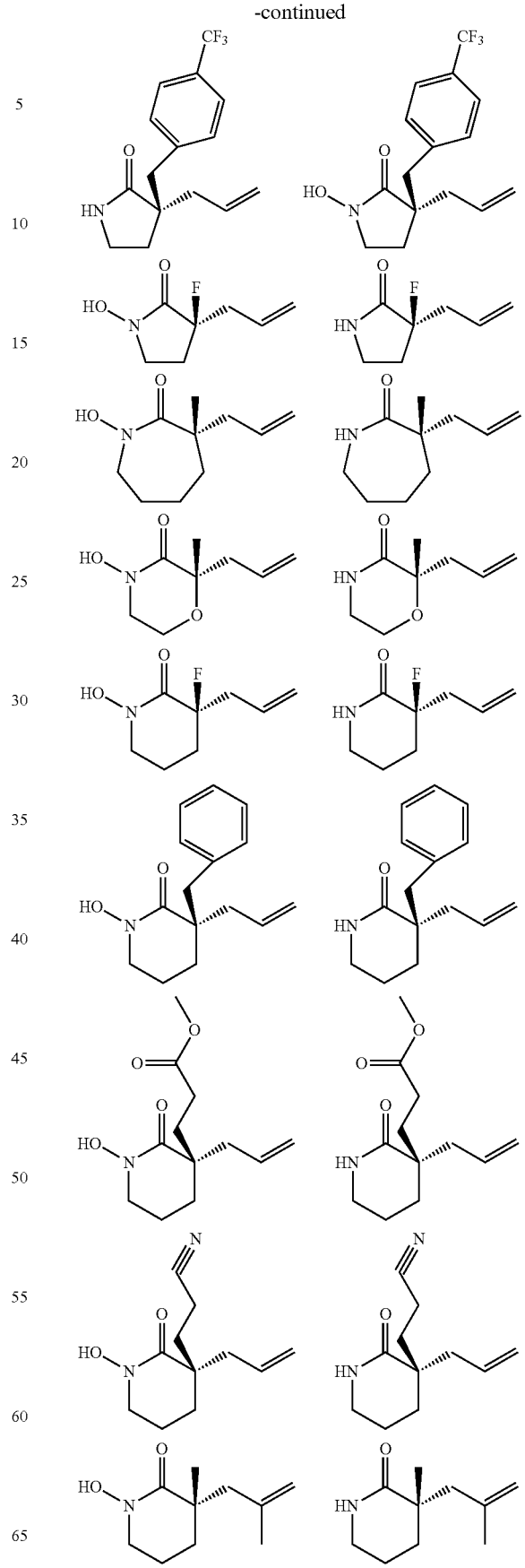

-continued
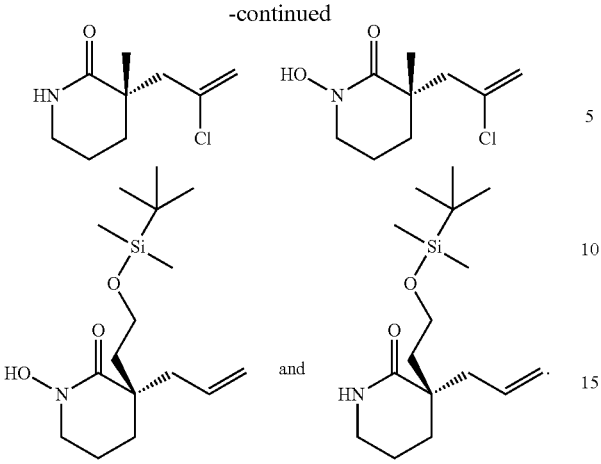
15. The method of claim 1, wherein the enantioenriched heteroatom-containing compound has an enantiomeric excess of greater than 50%.
16. The method of claim 1, wherein the enantioenriched heteroatom-containing compound has an enantiomeric excess of about 70% or greater.
* * * * *